US010028902B2

(12) United States Patent
Grayburn et al.

(10) Patent No.: US 10,028,902 B2
(45) Date of Patent: Jul. 24, 2018

(54) NUCLEAR LOCALIZATION OF GLP-1 STIMULATES MYOCARDIAL REGENERATION AND REVERSES HEART FAILURE

(71) Applicant: BAYLOR RESEARCH INSTITUTE, Dallas, TX (US)

(72) Inventors: Paul A. Grayburn, Plano, TX (US); Shuyuan Chen, Allen, TX (US)

(73) Assignee: Baylor Research Institute, Dallas, TX (US)

( * ) Notice: Subject to any disclaimer, the term of this patent is extended or adjusted under 35 U.S.C. 154(b) by 0 days.

(21) Appl. No.: 15/034,929

(22) PCT Filed: Nov. 7, 2014

(86) PCT No.: PCT/US2014/064606
§ 371 (c)(1),
(2) Date: May 6, 2016

(87) PCT Pub. No.: WO2015/070050
PCT Pub. Date: May 14, 2015

(65) Prior Publication Data
US 2016/0263017 A1  Sep. 15, 2016

Related U.S. Application Data

(60) Provisional application No. 61/901,693, filed on Nov. 8, 2013, provisional application No. 62/052,141, filed on Sep. 18, 2014.

(51) Int. Cl.
A61K 9/00        (2006.01)
A61K 38/26       (2006.01)
A61K 45/06       (2006.01)
A61K 9/127       (2006.01)
A61K 38/22       (2006.01)
A61K 31/616      (2006.01)
A61K 31/7048     (2006.01)
A61K 48/00       (2006.01)
C12N 15/87       (2006.01)

(52) U.S. Cl.
CPC ............ A61K 9/0009 (2013.01); A61K 9/127 (2013.01); A61K 31/616 (2013.01); A61K 31/7048 (2013.01); A61K 38/2292 (2013.01); A61K 38/26 (2013.01); A61K 45/06 (2013.01); A61K 48/0016 (2013.01); A61K 48/0075 (2013.01); C12N 15/87 (2013.01)

(58) Field of Classification Search
None
See application file for complete search history.

(56) References Cited

U.S. PATENT DOCUMENTS

| 5,545,618 A | 8/1996 | Buckley et al. | 514/5.9 |
| 6,191,102 B1 | 2/2001 | MiMarchi et al. | 514/4.8 |
| 6,268,343 B1 | 7/2001 | Knudsen et al. | 514/4.8 |
| 6,358,924 B1 | 3/2002 | Hoffmann | 514/6.9 |
| 6,458,924 B2 | 10/2002 | Knudsen et al. | 530/324 |
| 6,747,006 B2 | 6/2004 | Efendic | 514/6.8 |
| 7,576,050 B2 | 8/2009 | Greig et al. | 514/1.1 |
| 7,998,927 B2 | 8/2011 | Maggio | 514/7.2 |
| 2007/0207194 A1 | 9/2007 | Grayburn et al. | 424/450 |
| 2008/0300645 A1 | 12/2008 | Cholette | 607/40 |
| 2010/0143241 A1 | 6/2010 | Johnson et al. | 424/1.11 |
| 2011/0182979 A1 | 7/2011 | Shimoda et al. | 424/450 |
| 2011/0236431 A1 | 9/2011 | Wallrapp et al. | 424/400 |
| 2011/0245173 A1 | 10/2011 | Bachovchin et al. | 514/11.7 |
| 2011/0287086 A1 | 11/2011 | Grayburn et al. | 424/450 |

FOREIGN PATENT DOCUMENTS

EP   0 964 692   4/2008

OTHER PUBLICATIONS

Zhang, et al. (2012) "In Vivo Gene Delivery by Nonviral Vectors: Overcoming Hurdles?", Molecular Therapy, 20(7): 1298-1304.*
Hernot, et al. (2008) "Microbubbles in ultrasound-triggerred drug and gene delivery", Advanced Drug Delivery Reviews, 60: 1153-66.*
Chen, et al. (2013) "Stimulation of adult resident cardiac progenitor cells by durable myocardial expression of thymosin beta 4 with ultrasound-targeted microbubble delivery", Gene Therapy, 20: 225-33.*
Authors Unknown, https://en.wikipedia.org/wiki/Glucagon-like_peptide-1, downloaded Sep. 23, 2017, by the Wikimedia foundation, San Francisco, CA, 6 pages.*
Jin (2008) "Mechanisms underlying proglucagon gene expression", Journal of Endocrinology, 198: 17-28.*
Bekeredjian, et al., "Ultrasound-targeted microbubble destruction can repeatedly direct highly specific plasmid expression to the heart", Circulation. 2003; 108(8): 1022-26.
Berardi et al.,"State of the art for cardiotoxicity due to chemotherapy and to targeted therapies: A literature review", *Critical Reviews in Oncology/Hematology*, 88: 75-86, 2013.
Bertilsson et al., "Peptide Hormone Exendin-4 Stimulates Subventricular Zone Neurogenesis in the Adult Rodent Brain and Induces Recovery in an Animal Model of Parkinson's Disease", *Journal of Neuroscience Research*, 86: 326-338, 2008.
Biswas et al., "Glucagon-like Peptide-1 (GLP-1) Diminishes Neuronal Degeneration and Death Caused by NGF Deprivation by Suppressing Bim Induction", *Neurochem Res*, 33: 1845-1851, 2008.
Cadiñanos, et al., "Generation of an inducible and optimized piggyBac transposon system", Nucleic Acids Res. 2007; 35:e87.

(Continued)

Primary Examiner — Robert M Kelly
(74) Attorney, Agent, or Firm — Norton Rose Fulbright US LLP

(57) ABSTRACT

Embodiments of the disclosure provide methods and/or compositions useful for an individual in need of treatment of a cardiac-related medical condition. In particular cases, GLP-1 is employed in a ultrasound targeted microbubble destruction (UTMD) system for delivery to cardiac tissue, thereby stimulating myocardial regeneration and, in at least some cases, reversal of cardiomyopathy.

27 Claims, 14 Drawing Sheets

(56) References Cited

OTHER PUBLICATIONS

Cary, et al., "Transposon mutagenesis of baculoviruses: analysis of Trichoplusia ni transposon IFP2 insertions within the FP-locus of nuclear polyhedrosis viruses", Virology 1989; 172:156-69.

Castle et al., "Ultrasound-mediated targeted drug delivery: recent success and remaining challenges", *Am J Physiol Heart Circ Physiol*, 304: H350-H357, 2013.

Chen, et al., "Optimization of ultrasound parameters for cardiac gene delivery of adenoviral or plasmid deoxyribonucleic acid by ultrasound-targeted microbubble destruction", J Am Coll Cardiol. 2003; 42: 301-8.

Chen, et al., "Stimulation of adult resident cardiac progenitor cells by durable myocardial expression of thymosin beta 4 with ultrasound-targeted microbubble delivery", Gene Ther. 2013; 20:225-33.

Chen, et al., "Transient overexpression of cyclin D2/CDK4/GLP1 genes induces proliferation and differentiation of adult pancreatic progenitors and mediates islet regeneration", Cell Cycle. 2012; 11:695-705.

Fraser, et al., "Assay for movement of Lepidopteran transposon IFP2 in insect cells using a baculovirus genome as a target DNA", Virology 1995; 211: 397-407.

Fujii et al., "Repeated and targeted transfer of angiogenic plasmids into the infarcted rat heart via ultrasound targeted microbubble destruction enhances cardiac repair", *Eur Heart J.*, 32(16): 2075-84, 2010.

Halbirk, et al., "Cardiovascular and metabolic effects of 48-h glucagon-like peptide-1 infusion in compensated chronic patients with heart failure", *Am J Physiol Heart Circ Physiol.* 2010; 298:H1096-102.

Holscher, "The Role of GLP-1 in Neuronal Activity and Neurodegeneration", *Vitamins and Hormones*, vol. 84, Chapter 13, 2010.

International Search Report and Written Opinion issued in PCT/US2014/064606, dated Feb. 23, 2015.

Jiji et al., "Non-Invasive imaging and monitoring cardiotoxicity of cancer therapeutic drugs", *J Nucl Cardiol.*, 19(2): 377-88, 2012.

Kim et al., "GLP-1 receptor activation and Epac2 link atrial natriuretic peptide secretion to control of blood pressure", *Nature Medicine*, 19(5): 567-75., doi: 10.1038/nm.3128. Epub 2013.

Korpanty, et al., "Targeting of VEGF-mediated angiogenesis to rat myocardium using ultrasonic destruction of microbubbles", Gene Therapy. 2005; 12: 1305-12.

McGovern et al., "Effects of the glucagon-like polypeptide-1 analogue (Val$^8$)GLP-1 on learning, progenitor cell proliferation and neurogenesis in the C57B/16 mouse brain", *Brain Research*, 1473: 204-213, 2012.

Nikolaidis et al., "Effects of glucagon-like peptide-1 in patients with acute myocardial infarction and left ventricular dysfunction after successful reperfusion", *Circulation*, 109(8): 962-965, 2004.

Roger et al., "Heart Disease and Stroke Statistics—2012 Update: A Report From the American Heart Association", *Circulation*, DOI: 10.1161/CIR.0b013e31823ac046, e1-e1002, 2011.

Saridey, et al., "PiggyBac transposon-based inducible gene expression in vivo after somatic cell gene transfer", Mol Ther. 2009; 17: 2115-20.

Timmers, et al., "Exenatide reduces infarct size and improves cardiac function in a porcine model of ischemia and reperfusion injury", J Am Coll Cardiol. 2009; 53:501-10.

Ussher, et al., "Cardiovascular biology of the incretin system", Endocr Rev. 2012; 33:187-215.

Grayburn, "Myocardial Regeneration in Adriamycin-Induced Cardiomyopathy by UTMD", Power Point Presentation, Sep. 19, 2014.

Supplementary Partial European Search Report issued in European Application No. 14859741.2 dated Jul. 10, 2017.

Drucker, Daniel J., Minireview: The Glucagon-Like Peptides; Endrocrinology—The Endrocrinology Society; vol. 142, No. 2; Sep. 6, 2000.

Yusta, Bernado, et al; Glp-1 Receptor Activation Improves ß Cell Function and Survival Following Induction of Endoplasmic Reticulum Stress; Cell Metabolism 4, 391-406; Nov. 2006.

Campbell, Johnathan E., et al; Pharmacology, Physiology, and Mechanisms of Incretin Hermone Action; Cell Metabolism 17, Jun. 4, 2013.

Ussher, John R., et al; Cardiovascular Biology of the Incretin System; PubMed Central Canda; Endocr Rev., Apr. 1, 2012; 33(2): 187-215.

\* cited by examiner

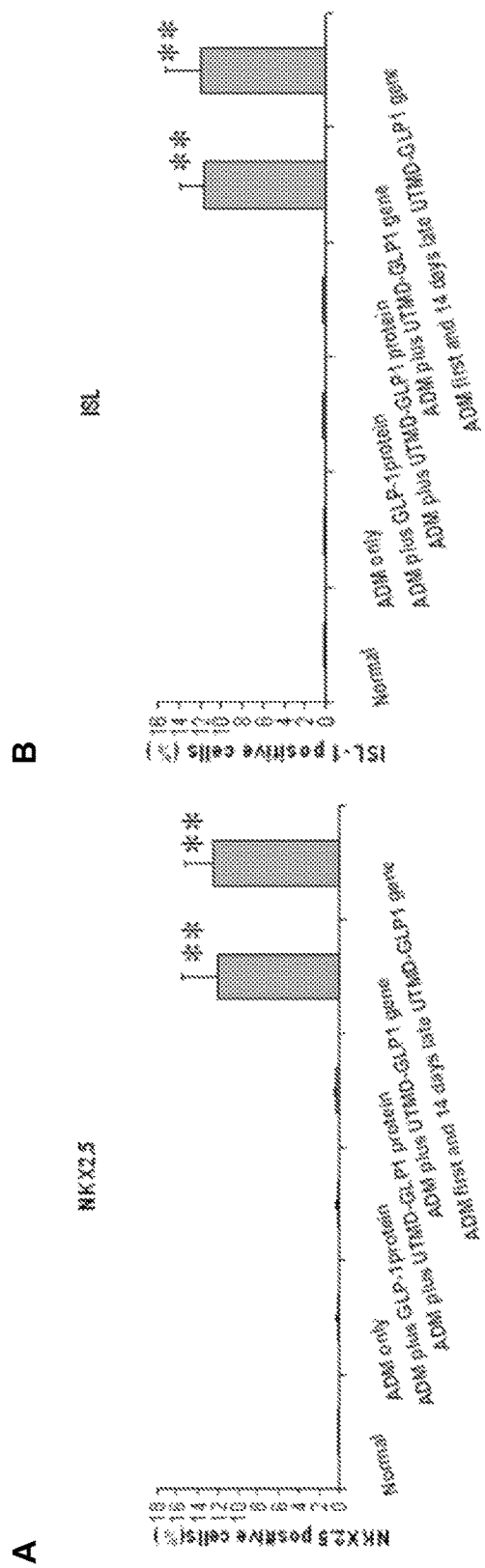
FIG. 9
FIG. 10

NUCLEAR LOCALIZATION OF GLP-1 STIMULATES MYOCARDIAL REGENERATION AND REVERSES HEART FAILURE

This application is a national phase application under 35 U.S.C. § 371 of International Application No. PCT/US2014/064606, filed Nov. 7, 2014, which claims priority to U.S. Provisional Patent Application Ser. No. 61/901,693, filed Nov. 8, 2013, and claims priority to U.S. Provisional Patent Application Ser. No. 62/052,141, filed Sep. 18, 2014, the entire contents of each of which are incorporated by reference herein in their entirety.

TECHNICAL FIELD

The field for the present disclosure includes at least the fields of cell biology, molecular biology, and medicine, such as cardiac medicine.

BACKGROUND

There are nearly 5 million Americans with congestive heart failure (CHF) and approximately 550,000 new cases are diagnosed in the U.S. each year. Congestive heart failure affects people of all ages, from children and young adults to the middle-aged and the elderly (Roger, et al., 2012). It is very crucial to find new resource of cardiac muscle regeneration for CHF treatments. There are various theories about the origin of regenerating cardiac muscle cells. These include self-replication of pre-existing adult cardiac muscle cells (Senyo, et al., 2012; Eulalio, et al., 2012), differentiation of adult resident cardiac progenitor cells (Smart, et al., 2011; Bolli, et al., 2011), dedifferentiation and proliferation adult cardiac muscle cells (Beltrami, et al., 2003; Jopling, et al., 2010; Porrello, et al., 2011), and transdifferentiation of fibroblast cells into cardiac muscle cells (Song, et al., 2012; Qian, et al., 2012). However, it remains controversial whether or not cardiomyocyte regeneration can be sufficient to reverse established cardiomyopathy.

Glucagon-like peptide-1 (GLP-1) is synthesized in intestinal endocrine cells in 2 principal major molecular forms, GLP-1 (7-36) amide and GLP-1(7-37) amide, which have wide bioactivities on CNS satiety centers, gastrointestinal motility, islet function and β cell growth, and energy homeostasis (Drucker, et al., 2001; Drucker, et al., 2002). Recently GLP-1 was found to have cardioprotective effects independent of those attributable to tight glycemic control (Halbirk, et al., 2010; Timmers, et al., 2009). Intravenous infusions of GLP-1 protein to patients with myocardial infarction or chronic heart failure improved global LV function and the function of ischemic LV segments. So far it has been only known that GLP-1 indirectly acts on GLP-1 receptors distributed on the membrane of cardiomyocytes and GLP-1R signaling to cAMP generation produces distinct downstream signaling events in intracellular calcium or ERK1/2 activation (Ussher, et al., 2012). However, no data have been published regarding the effects of GLP-1 gene delivery to heart.

The present disclosure satisfies a long-felt need in the art to provide therapy for one or more cardiac-related medical conditions, including to provide therapy for myocardial regeneration and reversal of heart failure, for example.

BRIEF SUMMARY

Embodiments of the present disclosure are directed to methods and/or compositions related to therapy and/or prevention of one or more cardiac-related medical conditions. Embodiments of the present disclosure concern regeneration of tissue, including muscle tissue, such as myocardial tissue. Certain embodiments relate to reversal of a cardiac-related medical condition (or improvement of at least one symptom thereof), including at least cardiac disease, cardiomyopathy, cardiotoxicity, congestive heart failure, ischemic heart disease, acute myocardial infarction, atrial fibrillation, and arrhythmias.

Particular aspects of the disclosure concern delivery of a polynucleotide, protein, peptide, or mixture thereof to a certain tissue for proliferation and/or differentiation of certain cells in the tissue. The tissue may be of any kind, but in specific cases it is muscle tissue, including cardiac tissue. In particular embodiments, methods and compositions of the disclosure allow for self-replication of pre-existing adult cardiac muscle cells, differentiation of adult resident cardiac progenitor cells, dedifferentiation and proliferation adult cardiac muscle cells, and/or transdifferentiation of fibroblast cells into cardiac muscle cells.

In specific embodiments, a polynucleotide, protein, peptide, or mixture thereof is targeted to a particular tissue of interest, including a muscle tissue, such as cardiac tissue, for example. The targeting may include an ultrasound targeted microbubble destruction (UTMD) system for delivery of the polynucleotide or protein or peptide to the tissue of interest, including cardiac tissue, for example. In particular cases, the polynucleotide, protein, peptide, or mixture thereof localizes to the nucleus of cells in the targeted tissue. In certain aspects, the nuclear localization occurs in the absence of receptors for the expression product of the polynucleotide or the protein or peptide on one or more cells in the targeted tissue. In specific embodiments, cardiac tissue cells lack receptors for GLP-1 and a particular liposome composition comprising GLP-1 is provided to the cells and uptaken therein under certain conditions. Particular embodiments include nuclear localization of GLP-1.

Embodiments of the disclosure include GLP-1 polynucleotides utilized for a therapeutic purpose, including for therapy for a cardiac-related medical condition. The polynucleotide may encompass part or all of GLP-1, for example. In certain cases, the polynucleotide is an expression vector that may or may not include a nuclear localization signal (NLS).

Embodiments of the disclosure include delivery of one or more polynucleotides that stimulate regeneration of cells (such as muscle cells, including cardiomyocytes) and/or tissue (including cardiac tissue). Particular aspects for such embodiments result in reversal of one or more cardiac-related medical conditions. Certain aspects for such embodiments result in improvement of at least one symptom of a cardiac-related medical condition. In exemplary embodiments, the cardiac-related medical condition is heart failure. The heart failure may be the result of one or more causes, including heart failure following exposure to one or more drugs, including chemotherapy drugs, such as Adriamycin.

Embodiments of the disclosure include at least one of the following: targeted delivery of GLP-1 gene viral or plasmid vectors to the heart and/or targeted delivery of nuclear localization of therapeutic peptides to heart; for example, one can utilize one or more nuclear location signal peptides with GLP-1 peptides.

Particular but exemplary indications of embodiments of the disclosure include at least applications for 1) congestive heart failure; 2) prevention from ventricular remodeling or aneuysm of myocardial infarction; and/or 3) cardiomyopathy. Other indications may also include coronary artery disease, ischemic heart disease, valvular heart disease, arrhythmias, etc. In specific embodiments, methods and compositions of the disclosure provide cardiomyocyte regeneration that is sufficient to reverse established cardiomyopathy, congestive heart failure, and prevention from ventricular remodeling or aneuysm of myocardial infarction.

Aspects of the disclosure include delivery of GLP-1 gene directly to the heart of a mammal that has or is susceptible to heart function failure, such as that induced by adriamycin. Ultrasound targeted microbubble destruction (UTMD) (Chen, et al., 2003; Bekeredjian, et al., 2003; Korpany, et al., 2005; Chen, et al., 2012; Chen, et al., 2013 in vivo may be employed, in embodiments. In particular aspects, UTMD is used to deliver GLP-1 gene, for example under a piggybac transposon plasmid system (Saridey, et al., 2009; Cary, et al., 1989; Fraser, et al., 1995; Cadinanos, et al., 2007), to mammalian hearts. Provided herein is demonstration that after a single UTMD treatment, transgenic GLP-1 was surprisingly over-expressed in nuclei of rat heart cells with evidence that transfected cardiac cells underwent proliferation and differentiation. However, in specific embodiments multiple deliveries of UTMD/GLP-1 are utilized. GLP-1 delivery to heart stimulates the regeneration of cardiac muscle and reversal of cardiomyopathy, for example induced by adriamycin.

In particular embodiments, an individual that receives methods or compositions of the disclosure is not diabetic, has not been diagnosed as diabetic, has no signs of being diabetic, is not suspected of being diabetic, and/or is not at risk of being diabetic. In some cases, an individual happens to have diabetes but is in need of cardiac therapy that was not previously diagnosed; such methods of the present disclosure may include the step of diagnosing a need for cardiac therapy in an individual with diabetes.

In embodiments of the disclosure, there is a method of localizing GLP-1 and/or TB4 to the nucleus of cells, comprising the steps of providing to the cells an effective amount of GLP-1- (and/or TB4-) comprising lipid-stabilized microbubbles; and exposing the microbubbles to ultrasound conditions sufficient to deliver GLP-1 and/or TB4 into the nuclei of the cells. In particular cases, the cell membrane of the cells lacks GLP-1 receptors, although in some cases the cell membrane of the cells has GLP-1 receptors. The cells may be located in vitro or in vivo. The cells may be muscle cells, neural cells, kidney cells, brain cells, cartilage cells, cardiac cells, cardiac progenitor cells, yellow adipocytes, white adipocytes, or liver cells. Particular muscle cells include cardiomyocytes, skeletal myocytes, or smooth muscle myocytes. In some cases, the neural cell is a central neural cell or a peripheral neural cell.

In particular aspects of the disclosure, a GLP-1 is further defined as a GLP-1 nucleic acid or a GLP-1 protein. A GLP-1 nucleic acid may be comprised in a vector, such as a retroviral vector, lentiviral vector, adenoviral vector, adeno-associated vector, or plasmid, including a piggyback transposon gene delivery plasmid, for example. Expression of a GLP-1 nucleic acid may be regulated by CMV or a tissue-specific promoter. In some cases, a GLP-1 nucleic acid further comprises sequence that encodes a nuclear localization signal. In particular aspects of the disclosure, TB4 is further defined as a TB4 nucleic acid or a TB4 protein. A TB4 nucleic acid may be comprised in a vector, such as a retroviral vector, lentiviral vector, adenoviral vector, adeno-associated vector, or plasmid, including a piggyback transposon gene delivery plasmid, for example. Expression of a TB4 nucleic acid may be regulated by CMV or a tissue-specific promoter. In some cases, a TB4 nucleic acid further comprises sequence that encodes a nuclear localization signal.

Microbubbles employed in particular methods comprise albumin, polymer shell, phospholipid, or a graphite shell, and the microbubbles may further comprise a gas, such as perfluoropropane, air, sulfur hexafluoride, perfluorobutane, perfluoropentane, and nitrogen.

The cells targeted in methods of the disclosure may be in an individual that has a cardiac-related medical condition, such as one selected from the group consisting of cardiac disease, cardiomyopathy, cardiotoxicity, congestive heart failure, myocardial infarction, cardiac ischemia, pericarditis, cardiac systolic dysfunction, and arryhthmia. In cases of cardiomyopathy, the condition may be induced by a drug, such as a chemotherapy drug (like Adriamycin) or a monoclonal antibody. Examples of drugs include those selected from the group consisting of anthracyclines; taxanes; fluoropyrimidine; cyclophosphamide; bevacizumab; trastuzomab; lapatinib; sorafenib; and sunitinib. The cardiomyopathy may be ischemic or non-ischemic cardiomyopathy. The cardiomyopathy may be caused by long-term high blood pressure, heart valve problems, heart tissue damage from a previous heart attack, chronic rapid heart rate, metabolic disorders, nutritional deficiencies, pregnancy, alcohol abuse, drug abuse, chemotherapy drugs, viral infection, hemochromatosis, genetic condition, elevated cholesterol levels, or a combination thereof.

In particular aspects, an individual is provided with an additional cardiac disease therapy, such as an additional cardiomyopathy therapy.

In certain embodiments, there is a method of regenerating cells at a desired location in an individual, comprising the steps of delivering to the location an effective amount of GLP-1- (and/or TB4-) comprising lipid-stabilized microbubbles; and exposing the microbubbles to ultrasound conditions sufficient to deliver GLP-1 and/or TB4 into the nuclei of cells at the location. The cell membrane of the cells may or may not lack GLP-1 receptors. The cells may be muscle cells, neural cells, kidney cells, brain cells, cartilage cells, cardiac cells, cardiac progenitor cells, yellow adipocytes, white adipocytes, liver cells, and bone marrow-derived progenitor cells. In some cases, the location is at a region of the heart. Exemplary muscle cells include cardiomyocytes, skeletal myocytes, or smooth muscle myocytes. In embodiments wherein the location is the brain, the method steps may circumvent the skull of the individual, such as the microbubbles being delivered to the brain through the eye, up through the chin, or in a hole or flap in the skull. In some cases, the location is at a region of the spinal cord or is at a region of the peripheral nervous system. A delivering step may comprise injection, intravenous perfusion, intra-coronary artery myocardium perfusion, intra-artery organ perfusion by catheter, or coronary sinus perfusion catheter, for example. The individual may have a cardiac-related medical condition, such as cardiac disease, cardiomyopathy, cardiotoxicity, congestive heart failure, myocardial infarction, cardiac ischemia, pericarditis, cardiac systolic dysfunction, and arrhythmia.

Embodiments of the disclosure include methods and/or compositions for regeneration of cardiac muscle and reversal of myocardial ischemic injury, for example. In particular embodiments, there are methods for stimulating proliferation of resident adult cardiac progenitor or cardiac muscle cells in mammalian hearts that have had a cardiac-related medical condition, such as acute ischemic injury, for example. In certain embodiments, such methods are achieved with compositions comprising GLP-1 and, in particular embodiments, also thymosin beta 4 (TB4); in specific embodiments, the GLP-1 and/or TB4 includes a nuclear localization signal. In particular embodiments, GLP-1 (with or without a nuclear localization signal (NLS)) and TB4 efficiently stimulate proliferation and differentiation of adult cardiac muscle cells into three intact cardiac cell lineages in mammalian ischemic heart-vascular endothelial cells, coronary artery smooth muscle cells and cardiac muscle cells. The GLP-1 and/or TB4 may be provided to an individual in microbubbles as contemplated herein, although in some embodiments they are provided without microbubbles. The GLP-1 and/or TB4 may be provided in nucleic acid form or in proteinaceous form. In specific embodiments, the GLP-1 and TB4 are provided in nucleic acid form, and they may or may not be on the same nucleic acid molecule. In any event, the expression of GLP-1 and TB4 may or may not be controlled by the same regulatory element(s). GLP-1 and TB4 in microbubbles may be delivered locally to the heart. In specific embodiments, GLP-1 and/or TB4 may be associated with a piggyback transposon plasmid.

Embodiments of the disclosure include myocardial regeneration using methods and/or compositions as contemplated herein. The myocardial regeneration may be following any cardiac-related medical condition. In specific embodiments, myocardial regeneration occurs following cardiomyopathy, for example. In particular embodiments, myocardial regeneration after UTMD GLP-1 myocardial nuclear delivery is mediated by dedifferentiation and proliferation of nuclear FOXO1-positive cardiac muscle cells that, in specific embodiments, express embryonic stem cell markers (such as OCT4, Nanog, SOX2, and/or c-kit) and proliferating markers (such as Ki-67, BrDU, PHH3, and/or Aurora B).

In embodiments of the disclosure, treatment of an individual with UTMD comprising GLP-1 (with or without NLS) and/or TB4 resulted in overexpression of GLP-1 and/or TB4, respectively, in nuclei of heart cells, and the transfected cardiac cells undergo dedifferentiation and proliferation. Such delivery results in myocardial regeneration and reversal of cardiomyopathy.

In some embodiments, there is a kit, housed in a suitable container, comprising: a polynucleotide encoding at least part of GLP-1 and/or primers suitable to amplify at least part of a GLP-1 nucleic acid sequence, and; one or more reagents suitable for generating liposomes. Functional fragments of GLP-1 may be provided in the kit. The GLP-1 may be in nucleic acid form or in protein form. The kit may further comprise an additional therapeutic compound, such as a cardiac disease therapeutic compound. The additional therapeutic compound may be an ACE Inhibitor, aldosterone inhibitor, angiotensin II receptor blocker (ARBs); beta-blocker, calcium channel blocker, cholesterol-lowering drug, digoxin, diuretics, inotropic therapy, potassium, magnesium, vasodilator, anticoagulant medication, aspirin, or a combination thereof. In particular embodiments, the kit comprises a polynucleotide encoding at least part of thymosin beta 4 (TB4) and/or primers suitable to amplify at least part of a TB4 nucleic acid sequence. In some embodiments, the TB4 is in protein form and is provided in the kit. In particular embodiments, the kit comprises a polynucleotide that comprises both GLP-1 and TB4 nucleic acid sequence.

The foregoing has outlined rather broadly the features and technical advantages of the present disclosure in order that the detailed description of the disclosure that follows may be better understood. Additional features and advantages of the disclosure will be described hereinafter which form the subject of the claims of the disclosure. It should be appreciated by those skilled in the art that the conception and specific embodiment disclosed may be readily utilized as a basis for modifying or designing other structures for carrying out the same purposes of the present disclosure. It should also be realized by those skilled in the art that such equivalent constructions do not depart from the spirit and scope of the disclosure as set forth in the appended claims. The novel features which are believed to be characteristic of the disclosure, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present disclosure.

BRIEF DESCRIPTION OF THE DRAWINGS

For a more complete understanding of the present disclosure, reference is now made to the following descriptions taken in conjunction with the accompanying drawing, in which:

FIG. 9. Panel A is a graph showing the percentage of anti-NKX2.5 positive cardiac muscle cells. Panel B is a graph showing the percentage of anti-ISL-1 positive cardiac muscle cells. Values are presented as mean±SEM. n=6 per group; **P<0.001 vs control groups.

FIG. 10. Schematic depiction of GLP1NLS cDNA;

DETAILED DESCRIPTION

I. Exemplary Definitions

Figure 1:
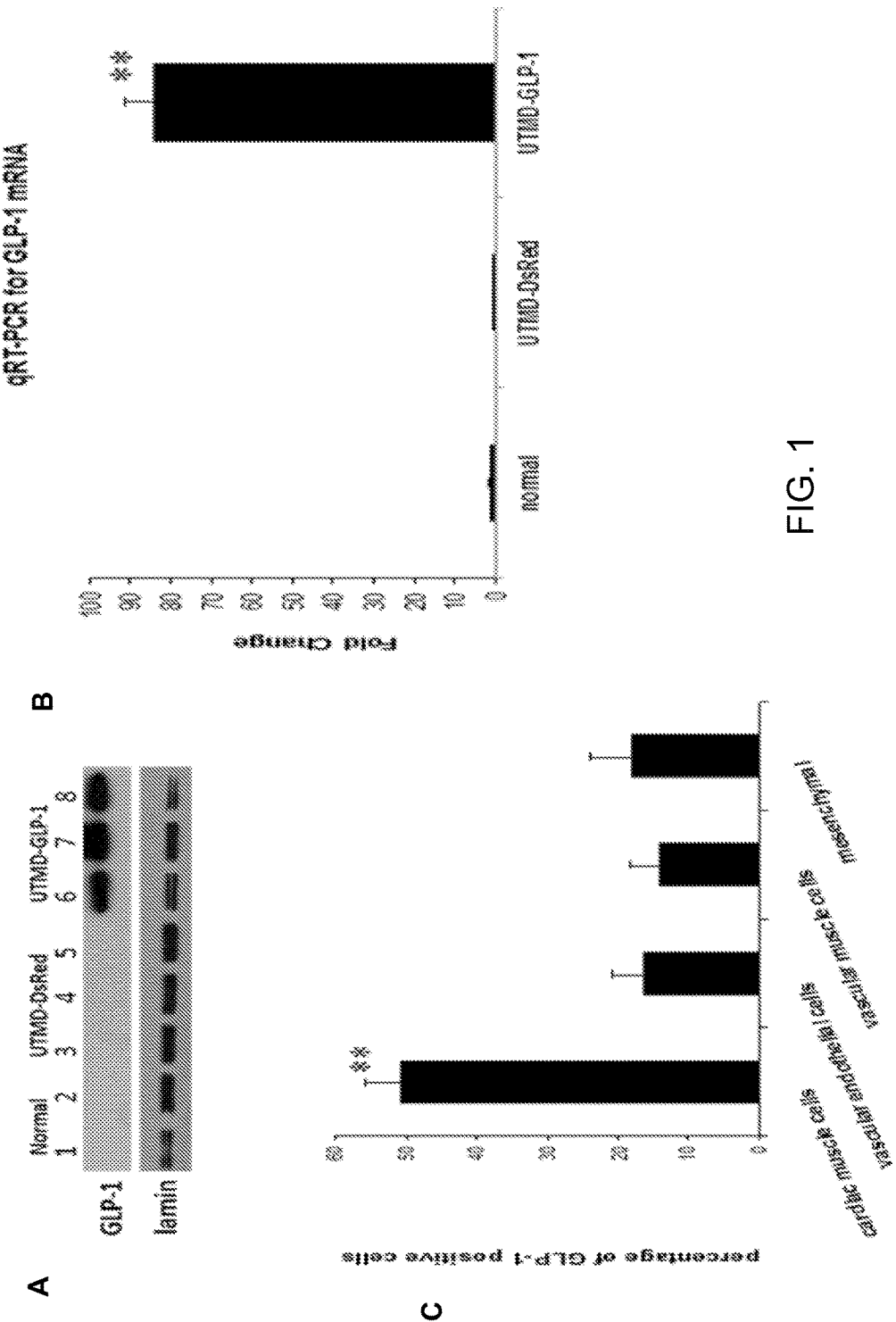
FIG. 1. UTMD GLP-1NLS gene delivery to rat heart showing nuclear localization of GLP-1 signal in cardiac cells. Panel A is western blot to detect GLP-1 from nuclear protein extract of heart tissue, lamin is a marker of nuclear protein. Panel B is qRT-PCR for GLP1 cDNA. Panel C is percentage of cell type in GLP-1 positive cells. Values are presented as mean±SEM. n=6 per group; **P<0.001 vs control groups.

As used herein, the use of the word "a" or "an" when used in conjunction with the term "comprising" in the claims and/or the specification may mean "one," but it is also consistent with the meaning of "one or more," "at least one," and "one or more than one." Some embodiments of the disclosure may consist of or consist essentially of one or more elements, method steps, and/or methods of the disclosure. It is contemplated that any method or composition described herein can be implemented with respect to any other method or composition described herein.

The term "cardiac-related medical condition" as used herein refers to any medical condition that affects heart tissue, including that affects heart function.

II. General Aspects of the Disclosure

The present disclosure provides methods and/or compositions for treatment and/or prevention of at least one cardiac-related medical condition. Such methods and compositions employ at least part of GLP-1 and a UTMD system. In particular aspects, UTMD directly delivers a GLP-1 polynucleotide into the nuclei of cardiomyocytes (that lack GLP-1 cell surface receptors). Upon translation of the polynucleotide inside the cell, this GLP-1 gene product concentrates in the nuclei of cardiomyocytes and does not excrete out into circulation. This nuclear GLP-1 stimulates myocardial regeneration via proliferation or self-replication of existing cardiomyocytes, in specific embodiments. Embodiments provide a new molecular mechanism of nuclear GLP-1 action different from routine GLP-1 peptide in cardioprotecting effects.

In at least some cases, particular GLP-1 polynucleotides are employed, including those that encode partial but functional GLP-1 gene products. In particular embodiments, TB4 polynucleotides are used in conjunction with GLP-1 polynucleotides, such as on the same or different polynucleotide in a UTMD system. Certain expression vectors may be useful for harboring the GLP-1 (and/or TB4) polynucleotide(s). Particular UTMD components may be utilized for delivery of the GLP-1 and/or TB4 polynucleotide(s).

III. Cardiac-Related Medical Conditions and Treatment and/or Prevention Thereof In specific embodiments, the cardiac-related medical condition is selected from the group consisting of cardiac disease, cardiovascular disease, heart disease, cardiomyopathy, cardiotoxicity, myocardial infarction, cardiac ischemic disease, arrhythmias, coronary artery disease, and a combination thereof.

Particular types of cardiovascular disease may be treated or prevented, such as coronary artery disease (also known as coronary heart disease and ischaemic heart disease); cardiomyopathy (diseases of cardiac muscle); hypertensive heart disease; heart failure; cor pulmonale; cardiac dysrhythmias; inflammatory heart disease; endocarditis; inflammatory cardiomegaly; myocarditis; valvular heart disease; cerebrovascular disease; peripheral arterial disease; congenital heart disease; and rheumatic heart disease.

In particular aspects of the disclosure, cardiomyopathy is the cardiac-related medical condition. The cardiac-related medical condition (including, for example, cardiomyopathy) may be caused by one or more of a variety of characteristics, including, for example, long-term high blood pressure; heart valve problems; heart tissue damage (such as from a previous heart attack); chronic rapid heart rate; metabolic disorders, such as thyroid disease or diabetes; nutritional deficiencies of essential vitamins or minerals, such as thiamin (vitamin B-1), selenium, calcium and/or magnesium; pregnancy; alcohol abuse; drug abuse, including of narcotics or prescription drugs, such as cocaine or antidepressant medications, such as tricyclic antidepressants; use of some chemotherapy drugs to treat cancer (including Adriamycin); certain viral infections; hemochromatosis and/or an unknown cause or undetected cause. The cardiac-related medical condition may be directly or indirectly caused by cancer therapeutics, both small molecule drugs and biologics, that are associated with cardiotoxicity, for example. Examples include anthracyclines; taxanes; fluoropyrimidine; cyclophosphamide; bevacizumab; trastuzomab; lapatinib; sorafenib; and sunitinib. The drug may be an immunogenic composition, such as a monoclonal antibody, such as Herceptin, for example.

In some cases, methods and compositions of the present disclosure are employed for prevention of one or more cardiac-related medical conditions or delay of onset of one or more cardiac-related medical conditions or reduction of extent of one or more symptoms of one or more cardiac-related medical conditions. In particular cases, such prevention, delay or onset, or reduction of extent of one or more symptoms, occurs in an individual that is at risk for a cardiac-related medical condition. Exemplary risk factors include one or more of the following: age, gender (male, although it occurs in females), high blood pressure, high serum cholesterol levels, tobacco smoking, excessive alcohol consumption, sugar consumption, family history, obesity, lack of physical activity, psychosocial factors, diabetes mellitus, overweight, genetic predisposition, and/or exposure to air pollution.

IV. GLP-1 and TB4 Compositions

Certain embodiments of the present disclosure concern a GLP-1 and/or TB4 nucleic acid, which also may be referred to as a GLP-1 polynucleotide and/or TB4 polynucleotide, respectively. In certain aspects, a GLP-1 and/or TB4 nucleic acid comprises a wild-type or a mutant GLP-1 and/or TB4 nucleic acid. In particular aspects, a GLP-1 and/or TB4 nucleic acid encodes for or comprises a transcribed nucleic acid. In other aspects, a GLP-1 and/or TB4 nucleic acid comprises a nucleic acid segment of GLP-1 and/or TB4, respectively, or a biologically functional equivalent thereof. In particular aspects, a GLP-1 and/or TB4 nucleic acid encodes a protein, polypeptide, or peptide. An exemplary human GLP-1 nucleic acid is at the GenBank® database of National Center for Biotechnology Information, Accession No. J04040.1 (SEQ ID NO:1), which is incorporated by reference herein in its entirety. An exemplary GLP-1 polypeptide is at GenBank® Accession Number AAA52567.1 (SEQ ID NO:2), which is incorporated by reference herein in its entirety. The skilled artisan recognizes that the entire GLP1 gene sequence is from 311 to 421 of proglucagon mRNA and that proglucagon mRNA includes glucagon, GLP-1 and GLP-2. SEQ ID NO:5 is an exemplary proglucagon nucleic acid sequence, and SEQ ID NO:6 is an exemplary proglucagon protein sequence.

In specific embodiments, GLP-1 (7-36) amide or GLP-1 (7-37) amide are utilized in the methods. In certain embodiments, nucleic acid encoding GLP-1 (7-36) amide and GLP-1(7-37) amide is utilized in the methods.

An exemplary human thymosin beta 4 (TB4) polynucleotide is at GenBank® Accession Number BC139925; SEQ ID NO:9), which is incorporated by reference herein in its entirety. An exemplary human thymosin beta 4 polypeptide is at GenBank® Accession Number AAI39926; SEQ ID NO:10), which is incorporated by reference herein in its entirety.

In specific embodiments, a functional fragment of GLP-1 is utilized instead of the entire GLP-1 polynucleotide or entire GLP-1 peptide. A functional fragment of GLP-1 is one that is sufficient to allow regeneration of cells upon exposure to the fragment and upon its uptake into the nucleus of the cells, either alone or in conjunction with TB4. In specific embodiments, the functional fragment of GLP-1 nucleic acid encodes (or the peptide comprises) at least 27, 26, 25, 24, 23, 22, 21, 20, 19, 18, 17, 16, 15, 14, 13, 12, 11, or 10 amino acids of SEQ ID NO:2. In specific embodiments, the functional fragment of GLP-1 nucleic acid encodes (or the peptide comprises) no more than 27, 26, 25, 24, 23, 22, 21, 20, 19, 18, 17, 16, 15, 14, 13, 12, 11, or 10 amino acids of SEQ ID NO:2. The functional GLP-1 fragment may be 100%, 99%, 98%, 97%, 96%, 95%, 94%, 93%, 92%, 91%, 90%, 85%, 80%. 75%, or 70% identity to SEQ ID NO:2.

In specific embodiments, a functional fragment of TB4 is utilized instead of the entire TB4 polynucleotide or entire TB4 peptide. A functional fragment of TB4 is one that is sufficient to allow regeneration of cells upon exposure to the fragment and upon its uptake into the nucleus of the cells, either alone or in conjunction with GLP-1. In specific embodiments, the functional fragment of TB4 nucleic acid encodes (or the peptide comprises) at least 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, or 10 amino acids of SEQ ID NO:10. In specific embodiments, the functional fragment of TB4 nucleic acid encodes (or the peptide comprises) no more than 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, or 10 amino acids of SEQ ID NO:10. The functional TB4 fragment may be 100%, 99%, 98%, 97%, 96%, 95%, 94%, 93%, 92%, 91%, 90%, 85%, 80%, 75%, or 70% identity to SEQ ID NO:10.

The term "nucleic acid" is well known in the art. A "nucleic acid" as used herein will generally refer to a molecule (i.e., a strand) of DNA, RNA or a derivative or analog thereof, comprising a nucleobase. A nucleobase includes, for example, a naturally occurring purine or pyrimidine base found in DNA (e.g., an adenine "A," a guanine "G," a thymine "T" or a cytosine "C") or RNA (e.g., an A, a G, an uracil "U" or a C). The term "nucleic acid" encompass the terms "oligonucleotide" and "polynucleotide," each as a subgenus of the term "nucleic acid." The term "oligonucleotide" refers to a molecule of between about 3 and about 100 nucleobases in length. The term "polynucleotide" refers to at least one molecule of greater than about 100 nucleobases in length.

These definitions generally refer to a single-stranded molecule, but in specific embodiments will also encompass an additional strand that is partially, substantially or fully complementary to the single-stranded molecule. Thus, a nucleic acid may encompass a double-stranded molecule or a triple-stranded molecule that comprises one or more complementary strand(s) or "complement(s)" of a particular sequence comprising a molecule. As used herein, a single stranded nucleic acid may be denoted by the prefix "ss," a double stranded nucleic acid by the prefix "ds," and a triple stranded nucleic acid by the prefix "ts."

A. Nucleobases

As used herein a "nucleobase" refers to a heterocyclic base, such as for example a naturally occurring nucleobase (i.e., an A, T, G, C or U) found in at least one naturally occurring nucleic acid (i.e., DNA and RNA), and naturally or non-naturally occurring derivative(s) and analogs of such a nucleobase. A nucleobase generally can form one or more hydrogen bonds ("anneal" or "hybridize") with at least one naturally occurring nucleobase in manner that may substitute for naturally occurring nucleobase pairing (e.g., the hydrogen bonding between A and T, G and C, and A and U).

"Purine" and/or "pyrimidine" nucleobase(s) encompass naturally occurring purine and/or pyrimidine nucleobases and also derivative(s) and analog(s) thereof, including but not limited to, those a purine or pyrimidine substituted by one or more of an alkyl, caboxyalkyl, amino, hydroxyl, halogen (i.e., fluoro, chloro, bromo, or iodo), thiol or alkylthiol moiety. Preferred alkyl (e.g., alkyl, caboxyalkyl, etc.) moeities comprise of from about 1, about 2, about 3, about 4, about 5, to about 6 carbon atoms. Other non-limiting examples of a purine or pyrimidine include a deazapurine, a 2,6-diaminopurine, a 5-fluorouracil, a xanthine, a hypoxanthine, a 8-bromoguanine, a 8-chloroguanine, a bromothymine, a 8-aminoguanine, a 8-hydroxyguanine, a 8-methylguanine, a 8-thioguanine, an azaguanine, a 2-aminopurine, a 5-ethylcytosine, a 5-methylcyosine, a 5-bromouracil, a 5-ethyluracil, a 5-iodouracil, a 5-chlorouracil, a 5-propyluracil, a thiouracil, a 2-methyladenine, a methylthioadenine, a N,N-diemethyladenine, an azaadenines, a 8-bromoadenine, a 8-hydroxyadenine, a 6-hydroxyaminopurine, a 6-thiopurine, a 4-(6-aminohexyl/cytosine), and the like.

A nucleobase may be comprised in a nucleoside or nucleotide, using any chemical or natural synthesis method described herein or known to one of ordinary skill in the art.

B. Nucleosides

As used herein, a "nucleoside" refers to an individual chemical unit comprising a nucleobase covalently attached to a nucleobase linker moiety. A non-limiting example of a "nucleobase linker moiety" is a sugar comprising 5-carbon atoms (i.e., a "5-carbon sugar"), including but not limited to a deoxyribose, a ribose, an arabinose, or a derivative or an analog of a 5-carbon sugar. Non-limiting examples of a derivative or an analog of a 5-carbon sugar include a 2'-fluoro-2'-deoxyribose or a carbocyclic sugar where a carbon is substituted for an oxygen atom in the sugar ring.

Different types of covalent attachment(s) of a nucleobase to a nucleobase linker moiety are known in the art. By way of non-limiting example, a nucleoside comprising a purine (i.e., A or G) or a 7-deazapurine nucleobase typically covalently attaches the 9 position of a purine or a 7-deazapurine to the 1'-position of a 5-carbon sugar. In another non-limiting example, a nucleoside comprising a pyrimidine nucleobase (i.e., C, T or U) typically covalently attaches a 1 position of a pyrimidine to a 1'-position of a 5-carbon sugar (Kornberg and Baker, 1992).

C. Nucleotides

As used herein, a "nucleotide" refers to a nucleoside further comprising a "backbone moiety". A backbone moiety generally covalently attaches a nucleotide to another molecule comprising a nucleotide, or to another nucleotide to form a nucleic acid. The "backbone moiety" in naturally occurring nucleotides typically comprises a phosphorus moiety, which is covalently attached to a 5-carbon sugar. The attachment of the backbone moiety typically occurs at either the 3'- or 5'-position of the 5-carbon sugar. However, other types of attachments are known in the art, particularly when a nucleotide comprises derivatives or analogs of a naturally occurring 5-carbon sugar or phosphorus moiety.

D. Nucleic Acid Analogs

A nucleic acid may comprise, or be composed entirely of, a derivative or analog of a nucleobase, a nucleobase linker moiety and/or backbone moiety that may be present in a naturally occurring nucleic acid. As used herein a "derivative" refers to a chemically modified or altered form of a naturally occurring molecule, while the terms "mimic" or "analog" refer to a molecule that may or may not structurally resemble a naturally occurring molecule or moiety, but possesses similar functions. As used herein, a "moiety" generally refers to a smaller chemical or molecular component of a larger chemical or molecular structure. Nucleobase, nucleoside and nucleotide analogs or derivatives are well known in the art, and have been described (see for example, Scheit, 1980, incorporated herein by reference).

Additional non-limiting examples of nucleosides, nucleotides or nucleic acids comprising 5-carbon sugar and/or backbone moiety derivatives or analogs, include those in U.S. Pat. No. 5,681,947 which describes oligonucleotides comprising purine derivatives that form triple helixes with and/or prevent expression of dsDNA; U.S. Pat. Nos. 5,652, 099 and 5,763,167 which describe nucleic acids incorporating fluorescent analogs of nucleosides found in DNA or RNA, particularly for use as flourescent nucleic acids probes; U.S. Pat. No. 5,614,617 which describes oligonucleotide analogs with substitutions on pyrimidine rings that possess enhanced nuclease stability; U.S. Pat. Nos. 5,670, 663, 5,872,232 and 5,859,221 which describe oligonucleotide analogs with modified 5-carbon sugars (i.e., modified 2'-deoxyfuranosyl moieties) used in nucleic acid detection; U.S. Pat. No. 5,446,137 which describes oligonucleotides comprising at least one 5-carbon sugar moiety substituted at the 4' position with a substituent other than hydrogen that can be used in hybridization assays; U.S. Pat. No. 5,886,165 which describes oligonucleotides with both deoxyribonucleotides with 3'-5' internucleotide linkages and ribonucleotides with 2'-5' internucleotide linkages; U.S. Pat. No. 5,714,606 which describes a modified internucleotide linkage wherein a 3'-position oxygen of the internucleotide linkage is replaced by a carbon to enhance the nuclease resistance of nucleic acids; U.S. Pat. No. 5,672,697 which describes oligonucleotides containing one or more 5' methylene phosphonate internucleotide linkages that enhance nuclease resistance; U.S. Pat. Nos. 5,466,786 and 5,792,847 which describe the linkage of a substituent moiety which may comprise a drug or label to the 2' carbon of an oligonucleotide to provide enhanced nuclease stability and ability to deliver drugs or detection moieties; U.S. Pat. No. 5,223,618 which describes oligonucleotide analogs with a 2 or 3 carbon backbone linkage attaching the 4' position and 3' position of adjacent 5-carbon sugar moiety to enhanced cellular uptake, resistance to nucleases and hybridization to target RNA; U.S. Pat. No. 5,470,967 which describes oligonucleotides comprising at least one sulfamate or sulfamide internucleotide linkage that are useful as nucleic acid hybridization probe; U.S. Pat. Nos. 5,378,825, 5,777,092, 5,623,070, 5,610,289 and 5,602,240 which describe oligonucleotides with three or four atom linker moiety replacing phosphodiester backbone moiety used for improved nuclease resistance, cellular uptake and regulating RNA expression; U.S. Pat. No. 5,858,988 which describes hydrophobic carrier agent attached to the 2'-O position of oligonuceotides to enhanced their membrane permeability and stability; U.S. Pat. No. 5,214,136 which describes olignucleotides conjugated to anthraquinone at the 5' terminus that possess enhanced hybridization to DNA or RNA; enhanced stability to nucleases; U.S. Pat. No. 5,700,922 which describes PNA-DNA-PNA chimeras wherein the DNA comprises 2'-deoxy-erythro-pentofuranosyl nucleotides for enhanced nuclease resistance, binding affinity, and ability to activate RNase H; and U.S. Pat. No. 5,708,154 which describes RNA linked to a DNA to form a DNA-RNA hybrid.

E. Polyether and Peptide Nucleic Acids

In certain embodiments, it is contemplated that a nucleic acid comprising a derivative or analog of a nucleoside or nucleotide may be used in the methods and compositions of the disclosure. A non-limiting example is a "polyether nucleic acid", described in U.S. Pat. No. 5,908,845, incorporated herein by reference. In a polyether nucleic acid, one or more nucleobases are linked to chiral carbon atoms in a polyether backbone.

Another non-limiting example is a "peptide nucleic acid", also known as a "PNA", "peptide-based nucleic acid analog" or "PENAM", described in U.S. Pat. Nos. 5,786,461, 5,891,625, 5,773,571, 5,766,855, 5,736,336, 5,719,262, 5,714,331, 5,539,082, and WO 92/20702, each of which is incorporated herein by reference. Peptide nucleic acids generally have enhanced sequence specificity, binding properties, and resistance to enzymatic degradation in comparison to molecules such as DNA and RNA (Egholm et al., 1993; PCT/EP/01219). A peptide nucleic acid generally comprises one or more nucleotides or nucleosides that comprise a nucleobase moiety, a nucleobase linker moiety that is not a 5-carbon sugar, and/or a backbone moiety that is not a phosphate backbone moiety. Examples of nucleobase linker moieties described for PNAs include aza nitrogen atoms, amido and/or ureido tethers (see for example, U.S. Pat. No. 5,539,082). Examples of backbone moieties described for PNAs include an aminoethylglycine, polyamide, polyethyl, polythioamide, polysulfinamide or polysulfonamide backbone moiety.

In certain embodiments, a nucleic acid analogue such as a peptide nucleic acid may be used to inhibit nucleic acid amplification, such as in PCR, to reduce false positives and discriminate between single base mutants, as described in U.S. Pat. No. 5,891,625. Other modifications and uses of nucleic acid analogs are known in the art, and are encompassed herein. In a non-limiting example, U.S. Pat. No. 5,786,461 describes PNAs with amino acid side chains attached to the PNA backbone to enhance solubility of the molecule. In another example, the cellular uptake property of PNAs is increased by attachment of a lipophilic group. U.S. application Ser. No. 117,363 describes several alkylamino moeities used to enhance cellular uptake of a PNA. Another example is described in U.S. Pat. Nos. 5,766,855, 5,719,262, 5,714,331 and 5,736,336, which describe PNAs comprising naturally and non-naturally occurring nucleobases and alkylamine side chains that provide improvements in sequence specificity, solubility and/or binding affinity relative to a naturally occurring nucleic acid.

F. Preparation of Nucleic Acids

A nucleic acid may be made by any technique known to one of ordinary skill in the art, such as for example, chemical synthesis, enzymatic production or biological production. Non-limiting examples of a synthetic nucleic acid (e.g., a synthetic oligonucleotide), include a nucleic acid made by in vitro chemical synthesis using phosphotriester, phosphite or phosphoramidite chemistry and solid phase techniques such as described in EP 266,032, incorporated herein by reference, or via deoxynucleoside H-phosphonate intermediates as described by Froehler et al., 1986 and U.S. Pat. No. 5,705,629, each incorporated herein by reference. In the methods of the present disclosure, one or more oligonucleotide may be used. Various different mechanisms of oligonucleotide synthesis have been disclosed in for example, U.S. Pat. Nos. 4,659,774, 4,816,571, 5,141,813, 5,264,566, 4,959,463, 5,428,148, 5,554,744, 5,574,146, 5,602,244, each of which is incorporated herein by reference.

A non-limiting example of an enzymatically produced nucleic acid include one produced by enzymes in amplification reactions such as PCR™ (see for example, U.S. Pat. No. 4,683,202 and U.S. Pat. No. 4,682,195, each incorporated herein by reference), or the synthesis of an oligonucleotide described in U.S. Pat. No. 5,645,897, incorporated herein by reference. A non-limiting example of a biologically produced nucleic acid includes a recombinant nucleic acid produced (i.e., replicated) in a living cell, such as a recombinant DNA vector replicated in bacteria (see for example, Sambrook et al. 1989, incorporated herein by reference).

G. Purification of Nucleic Acids

A nucleic acid may be purified on polyacrylamide gels, cesium chloride centrifugation gradients, or by any other means known to one of ordinary skill in the art (see for example, Sambrook et al., 1989, incorporated herein by reference).

In certain aspect, the present disclosure concerns a nucleic acid that is an isolated nucleic acid. As used herein, the term "isolated nucleic acid" refers to a nucleic acid molecule (e.g., an RNA or DNA molecule) that has been isolated free of, or is otherwise free of, the bulk of the total genomic and transcribed nucleic acids of one or more cells. In certain embodiments, "isolated nucleic acid" refers to a nucleic acid that has been isolated free of, or is otherwise free of, bulk of cellular components or in vitro reaction components such as for example, macromolecules such as lipids or proteins, small biological molecules, and the like.

H. Nucleic Acid Segments

In certain embodiments, the nucleic acid is a nucleic acid segment. As used herein, the term "nucleic acid segment," are smaller fragments of a nucleic acid, such as for non-limiting example, those that encode only part of the GLP-1 peptide or polypeptide sequence. Thus, a "nucleic acid segment" may comprise any part of a gene sequence, of from about 2 nucleotides to the full length of the GLP-1 peptide or polypeptide encoding region.

Various nucleic acid segments may be designed based on a particular nucleic acid sequence, and may be of any length. By assigning numeric values to a sequence, for example, the first residue is 1, the second residue is 2, etc., an algorithm defining all nucleic acid segments can be created:

n to n+y where n is an integer from 1 to the last number of the sequence and y is the length of the nucleic acid segment minus one, where n+y does not exceed the last number of the sequence. Thus, for a 10-mer, the nucleic acid segments correspond to bases 1 to 10, 2 to 11, 3 to 12 . . . and so on. For a 15-mer, the nucleic acid segments correspond to bases 1 to 15, 2 to 16, 3 to 17 . . . and so on. For a 20-mer, the nucleic segments correspond to bases 1 to 20, 2 to 21, 3 to 22 . . . and so on. In certain embodiments, the nucleic acid segment may be a probe or primer. As used herein, a "probe" generally refers to a nucleic acid used in a detection method or composition. As used herein, a "primer" generally refers to a nucleic acid used in an extension or amplification method or composition.

I. Nucleic Acid Complements

The present disclosure also encompasses a nucleic acid that is complementary to a GLP-1 nucleic acid. In particular embodiments the disclosure encompasses a nucleic acid or a nucleic acid segment complementary to the GLP-1 encoding sequence. A nucleic acid "complement(s)" or is "complementary" to another nucleic acid when it is capable of base-pairing with another nucleic acid according to the standard Watson-Crick, Hoogsteen or reverse Hoogsteen binding complementarity rules. As used herein "another nucleic acid" may refer to a separate molecule or a spatial separated sequence of the same molecule.

As used herein, the term "complementary" or "complement(s)" also refers to a nucleic acid comprising a sequence of consecutive nucleobases or semiconsecutive nucleobases (e.g., one or more nucleobase moieties are not present in the molecule) capable of hybridizing to another nucleic acid strand or duplex even if less than all the nucleobases do not base pair with a counterpart nucleobase. In certain embodiments, a "complementary" nucleic acid comprises a sequence in which about 70%, about 71%, about 72%, about 73%, about 74%, about 75%, about 76%, about 77%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, to about 100%, and any range derivable therein, of the nucleobase sequence is capable of base-pairing with a single or double stranded nucleic acid molecule during hybridization. In certain embodiments, the term "complementary" refers to a nucleic acid that may hybridize to another nucleic acid strand or duplex in stringent conditions, as would be understood by one of ordinary skill in the art.

In certain embodiments, a "partly complementary" nucleic acid comprises a sequence that may hybridize in low stringency conditions to a single or double stranded nucleic acid, or contains a sequence in which less than about 70% of the nucleobase sequence is capable of base-pairing with a single or double stranded nucleic acid molecule during hybridization.

J. Hybridization

As used herein, "hybridization", "hybridizes" or "capable of hybridizing" is understood to mean the forming of a double or triple stranded molecule or a molecule with partial double or triple stranded nature. The term "anneal" as used herein is synonymous with "hybridize." The term "hybridization", "hybridize(s)" or "capable of hybridizing" encompasses the terms "stringent condition(s)" or "high stringency" and the terms "low stringency" or "low stringency condition(s)."

As used herein "stringent condition(s)" or "high stringency" are those conditions that allow hybridization between or within one or more nucleic acid strand(s) containing complementary sequence(s), but precludes hybridization of random sequences. Stringent conditions tolerate little, if any, mismatch between a nucleic acid and a target strand. Such conditions are well known to those of ordinary skill in the art, and are preferred for applications requiring high selectivity. Non-limiting applications include isolating a nucleic acid, such as a gene or a nucleic acid segment thereof or detecting at least one specific mRNA transcript or a nucleic acid segment thereof, and the like.

Stringent conditions may comprise low salt and/or high temperature conditions, such as provided by about 0.02 M to about 0.15 M NaCl at temperatures of about 50° C. to about 70° C. It is understood that the temperature and ionic strength of a desired stringency are determined in part by the length of the particular nucleic acid(s), the length and nucleobase content of the target sequence(s), the charge composition of the nucleic acid(s), and to the presence or concentration of formamide, tetramethylammonium chloride or other solvent(s) in a hybridization mixture.

It is also understood that these ranges, compositions and conditions for hybridization are mentioned by way of non-limiting examples only, and that the desired stringency for a particular hybridization reaction is often determined empirically by comparison to one or more positive or negative controls. Depending on the application envisioned it is preferred to employ varying conditions of hybridization to achieve varying degrees of selectivity of a nucleic acid towards a target sequence. In a non-limiting example, identification or isolation of a related target nucleic acid that does not hybridize to a nucleic acid under stringent conditions may be achieved by hybridization at low temperature and/or high ionic strength. Such conditions are termed "low stringency" or "low stringency conditions", and non-limiting examples of low stringency include hybridization performed at about 0.15 M to about 0.9 M NaCl at a temperature range of about 20° C. to about 50° C. Of course, it is within the skill of one in the art to further modify the low or high stringency conditions to suite a particular application.

As used herein "wild-type" refers to the naturally occurring sequence of a nucleic acid at a genetic locus in the genome of an organism, or a sequence transcribed or translated from such a nucleic acid. Thus, the term "wild-type" also may refer to an amino acid sequence encoded by a nucleic acid. As a genetic locus may have more than one sequence or alleles in a population of individuals, the term "wild-type" encompasses all such naturally occurring allele(s). As used herein the term "polymorphic" means that variation exists (i.e., two or more alleles exist) at a genetic locus in the individuals of a population. As used herein "mutant" refers to a change in the sequence of a nucleic acid or its encoded protein, polypeptide or peptide that is the result of the hand of man.

The present disclosure also concerns the isolation or creation of a recombinant construct or a recombinant host cell through the application of recombinant nucleic acid technology known to those of skill in the art or as described herein. A recombinant construct or host cell may comprise a GLP-1 nucleic acid, and may express a GLP-1 protein, peptide or peptide, or at least one biologically functional equivalent thereof.

Herein, in certain embodiments, a "gene" refers to a nucleic acid that is transcribed. In certain aspects, the gene includes regulatory sequences involved in transcription, or message production or composition. In particular embodiments, the gene comprises transcribed sequences that encode for a protein, polypeptide or peptide. As will be understood by those in the art, this function term "gene" includes both genomic sequences, RNA or cDNA sequences or smaller engineered nucleic acid segments, including nucleic acid segments of a non-transcribed part of a gene, including but not limited to the non-transcribed promoter or enhancer regions of a gene. Smaller engineered gene nucleic acid segments may express, or may be adapted to express using nucleic acid manipulation technology, proteins, polypeptides, domains, peptides, fusion proteins, mutants and/or such like.

"Isolated substantially away from other coding sequences" means that the gene of interest forms the significant part of the coding region of the nucleic acid, or that the nucleic acid does not contain large portions of naturally-occurring coding nucleic acids, such as large chromosomal fragments, other functional genes, RNA or cDNA coding regions. Of course, this refers to the nucleic acid as originally isolated, and does not exclude genes or coding regions later added to the nucleic acid by the hand of man.

The nucleic acid(s) of the present disclosure, regardless of the length of the sequence itself, may be combined with other nucleic acid sequences, including but not limited to, promoters, enhancers, polyadenylation signals, restriction enzyme sites, multiple cloning sites, coding segments, and the like, to create one or more nucleic acid construct(s). As used herein, a "nucleic acid construct" is a nucleic acid engineered or altered by the hand of man, and generally comprises one or more nucleic acid sequences organized by the hand of man.

In a non-limiting example, one or more nucleic acid constructs may be prepared that include a contiguous stretch of nucleotides identical to or complementary (at least in part) to SEQ ID NO:1 or SEQ ID NO:9. A nucleic acid construct may be about 3, about 5, about 8, about 10 to about 14, or about 15, about 20, about 30, about 40, about 50, about 100, about 115, about 200, about 500, about 600, or about 650 nucleotides in length, as well as constructs of greater size, up to and including chromosomal sizes (including all intermediate lengths and intermediate ranges), given the advent of nucleic acids constructs such as a yeast artificial chromosome are known to those of ordinary skill in the art. It will be readily understood that "intermediate lengths" and "intermediate ranges", as used herein, means any length or range including or between the quoted values (i.e., all integers including and between such values). Non-limiting examples of intermediate lengths include about 11, about 12, about 13, about 16, about 17, about 18, about 19, etc.; about 21, about 22, about 23, etc.; about 31, about 32, etc.; about 51, about 52, about 53, etc.; about 101, about 102, about 103, etc.; about 151, about 152, about 153, etc.; about 600, about 601, about 605, about 610, etc. Non-limiting examples of intermediate ranges include about 3 to about 32, about 150 to about 750, etc.

In certain embodiments, the nucleic acid construct is a recombinant vector. In particular embodiments, the disclosure concerns one or more recombinant vector(s) comprising nucleic acid sequences that encode an GLP-1 protein, polypeptide or peptide that includes within its amino acid sequence a contiguous amino acid sequence in accordance with, or essentially as set forth in, SEQ ID NO:2, corresponding to SEQ ID NO:1 nucleic acid. In particular aspects, the recombinant vectors are DNA vectors.

In certain embodiments, the nucleic acid construct is a recombinant vector. In particular embodiments, the disclosure concerns one or more recombinant vector(s) comprising nucleic acid sequences that encode TB4 protein, polypeptide or peptide that includes within its amino acid sequence a contiguous amino acid sequence in accordance with, or essentially as set forth in, SEQ ID NO:10, corresponding to SEQ ID NO:9 nucleic acid. In particular aspects, the recombinant vectors are DNA vectors.

The term "biologically functional equivalent" is well understood in the art and is further defined in detail herein. Accordingly, a sequence that has 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% of amino acids that are identical or functionally equivalent to the amino acids of SEQ ID NO:2 or SEQ ID NO:10, provided the biological activity of the protein, polypeptide or peptide is maintained.

In certain other embodiments, the disclosure concerns at least one recombinant vector that include within its sequence a nucleic acid sequence essentially as set forth in SEQ ID NO:1 or SEQ ID NO:9. In particular embodiments, the recombinant vector comprises DNA sequences that encode protein(s), polypeptide(s) or peptide(s) exhibiting GLP-1 activity.

The term "functionally equivalent codon" is used herein to refer to codons that encode the same amino acid, such as the six codons for arginine and serine, and also refers to codons that encode biologically equivalent amino acids. Codon usage for various organisms and organelles can be found in the literature. Thus, it is contemplated that codon usage may be optimized for other animals, as well as other organisms such as a prokaryote (e.g., an eubacteria, an archaea), an eukaryote (e.g., a protist, a plant, a fungi, an animal), a virus and the like, as well as organelles that contain nucleic acids, such as mitochondria, chloroplasts and the like, based on the preferred codon usage as would be known to those of ordinary skill in the art.

It will also be understood that amino acid sequences or nucleic acid sequences may include additional residues, such as additional N- or C-terminal amino acids or 5' or 3' sequences, or various combinations thereof, and yet still be essentially as set forth in one of the sequences disclosed herein, so long as the sequence meets the criteria set forth above, including the maintenance of biological protein, polypeptide or peptide activity where expression of a proteinaceous composition is concerned. The addition of terminal sequences particularly applies to nucleic acid sequences that may, for example, include various non-coding sequences flanking either of the 5' and/or 3' portions of the coding region or may include various internal sequences, i.e., introns, which are known to occur within genes.

Excepting intronic and flanking regions, and allowing for the degeneracy of the genetic code, nucleic acid sequences that have between about 70% and about 79%; or more preferably, between about 80% and about 89%; or even more particularly, between about 90% and about 99%; of nucleotides that are identical to the nucleotides of SEQ ID NO:1 or SEQ ID NO:9 are encompassed in the disclosure.

Encompassed in the disclosure include sequences that are 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, or less percent identical to SEQ ID NO:1 or SEQ ID NO:2 (or SEQ ID NO:9 or SEQ ID NO:10). The sequences that are not 100 percent identical to SEQ ID NO:1 or SEQ ID NO:2 (or SEQ ID NO:9 or SEQ ID NO:10) may share their identity therewith at any region of the sequence, including the N-terminal or C-terminal ends, or inbetween thereof of SEQ ID NO:2 or the 5' or 3' ends or inbetween there of SEQ ID NO:1 (or SEQ ID NO:9 or SEQ ID NO:10 respectively).

It will also be understood that this disclosure is not limited to the particular nucleic acid or amino acid sequences of SEQ ID NO:1 or SEQ ID NO:2 (or SEQ ID NO:9 or SEQ ID NO:10), respectively. Recombinant vectors and isolated nucleic acid segments may therefore variously include these coding regions themselves, coding regions bearing selected alterations or modifications in the basic coding region, and they may encode larger polypeptides or peptides that nevertheless include such coding regions or may encode biologically functional equivalent proteins, polypeptide or peptides that have variant amino acids sequences.

The nucleic acids of the present disclosure encompass biologically functional equivalent GLP-1 proteins, polypeptides, or peptides. Such sequences may arise as a consequence of codon redundancy or functional equivalency that are known to occur naturally within nucleic acid sequences or the proteins, polypeptides or peptides thus encoded. Alternatively, functionally equivalent proteins, polypeptides or peptides may be created via the application of recombinant DNA technology, in which changes in the protein, polypeptide or peptide structure may be engineered, based on considerations of the properties of the amino acids being exchanged. Changes designed by man may be introduced, for example, through the application of site-directed mutagenesis techniques as discussed herein below, e.g., to introduce improvements or alterations to the antigenicity of the protein, polypeptide or peptide, or to test mutants in order to examine GLP-1 protein, polypeptide or peptide activity at the molecular level.

V. Ultrasound Targeted Microbubble Destruction (UTMD) System

In one aspect, there are methods of delivering a bioactive agent to a target organ or tissue in vivo by using an ultrasound-targeted microbubble destruction (UTMD), using microbubbles loaded with nanosphere cationic liposomes containing the bioactive agent. Exemplary microbubbles comprise but are not limited to neutrally charged lipids, polymers, metals, or acrylic shells suitable for in vivo ultrasound-targeted microbubble destruction. In one embodiment, the bioactive agent is first encapsulated within or attached to tiny cationic liposomes of nanoparticle size (10-60 nm) (hereinafter, nanosphere cationic liposomes either "loaded with" or "including" the bioactive agent refers to any bioactive agent encapsulated within or attached to the liposomes, e.g., cationic liposomes), and the liposomes are then attached to neutrally charged lipid-coated or albumin-coated microbubbles filled with a gas suitable for ultrasound microbubble destruction techniques, for example perfluoropropane. The liposomes may be attached to the outer surface of the microbubble shell, incorporated within the microbubble shell and/or encapsulated within the microbubble shell. In the present disclosure, one or more bioactive agents can be delivered either concomitantly or subsequently by ultrasound-targeted microbubble destruction using the neutrally charged lipid microbubbles loaded with bioactive agent-containing nanosphere cationic liposomes. In another aspect, the present disclosure is a method of treating a mammal in need of such treatment comprising administration of an effective amount of a composition comprising neutrally charged lipid microbubbles loaded with nanosphere cationic liposomes containing a bioactive agent via ultrasound-targeted microbubble destruction.

Examples of bioactive agents suitable for the present disclosure include one or more of polynucleotides (including GLP-1 polynucleotides) pharmaceuticals and drugs, bioactive synthetic organic molecules, proteins, peptides, polypeptides, vitamins, steroids, polyanionic agents, genetic material, and diagnostic agents. Bioactive vitamins, steroids, proteins, peptides and polypeptides can be of natural origin or synthetic. Exemplary polyanionic agents include but are not limited to sulphated polysaccharides, negatively charged serum albumin and milk proteins, synthetic sulphated polymers, polymerized anionic surfactants, and polyphosphates. Suitable diagnostic agents include but are not limited to dyes and contrast agents for use in connection with magnetic resonance imaging, ultrasound or computed tomography of a patient.

Suitable genetic material includes nucleic acids, nucleosides, nucleotides, and polynucleotides that can be either isolated genomic, synthetic or recombinant material; either single or double stranded; and either in the sense or antisense direction, with or without modifications to bases, carbohydrate residues or phosphodiester linkages. Exemplary sources for the genetic material include but are not limited to deoxyribonucleic acids (DNA), ribonucleic acids (RNA), complementary DNA (cDNA), messenger RNA (mRNA), ribosomal RNA (rRNA), short interfering RNA (siRNA), ribozymes, and mixed duplexes and triplexes of RNA and DNA.

Genetic materials are genes carried on expression vectors including but not limited to helper viruses, plasmids, phagemids, cosmids, and yeast artificial chromosomes. The genetic material suitable for the present disclosure is capable of coding for at least a portion of a therapeutic, regulatory, and/or diagnostic protein. Moreover, genetic materials can preferably code for more than one type of protein. For example, a bioactive agent may comprise plasmid DNA comprising genetic material encoding therapeutic protein and a selectable or diagnostic marker to monitor the delivery of the plasmid DNA, e.g., pDsRed-human insulin promoter. Such proteins include but are not limited to histocompatibility antigens, cell adhesion molecules, growth factors, coagulation factors, hormones, insulin, cytokines, chemokines, antibodies, antibody fragments, cell receptors, intracellular enzymes, transcriptional factors, toxic peptides capable of eliminating diseased or malignant cells. Other genetic materials that could be delivered by this technique included adenovirus, adeno-associated virus, retrovirus, lentivirus, RNA, siRNA, or chemicals that selectively turn on or off specific genes, such as polyamides or peptide fragments. Modifications to wild-type proteins resulting in agonists or antagonists of the wild type variant fall in the scope of this disclosure. The genetic material may also comprise a tissue-specific promoter or expression control sequences such as a transcriptional promoter, an enhancer, a transcriptional terminator, an operator or other control sequences.

Examples of other agents that may be used with the polynucleotides of the present disclosure include one or more of the following therapeutics pre-loaded into a liposome and associated with microbubbles including, but are not limited to, hormone products such as, vasopressin and oxytocin and their derivatives, glucagon and thyroid agents as iodine products and anti-thyroid agents; cardiovascular products as chelating agents and mercurial diuretics and cardiac glycosides; respiratory products as xanthine derivatives (theophylline and aminophylline); anti-infectives as aminoglycosides, antifungals (e.g., amphotericin), penicillin and cephalosporin antibiotics, antiviral agents (e.g., Zidovudine, Ribavirin. Amantadine, Vidarabine and Acyclovir), antihelmintics, antimalarials, and antituberculous drugs; biologicals such as antibodies (e.g., antitoxins and antivenins), vaccine antigens (e.g., bacterial vaccines, viral vaccines, toxoids); antineoplastics (e.g., nitrosoureas, nitrogen mustards, antimetabolites (fluorouracil, hormones, progestins and estrogens agonists and/or antagonists); mitotic inhibitors (e.g., Etoposide and/or *Vinca* alkaloids), radiopharmaceuticals (e.g., radioactive iodine and phosphorus products); and Interferon, hydroxyurea, procarbazine, Dacarbazine, Mitotane, Asparaginase and cyclosporine, including mixtures and combinations thereof. Other suitable therapeutics include, but are not limited to: thrombolytic agents such as urokinase; coagulants such as thrombin; antineoplastic agents, such as platinum compounds (e.g., spiroplatin, cisplatin, and carboplatin), methotrexate, adriamycin, taxol, mitomycin, ansamitocin, bleomycin, cytosine arabinoside, arabinosyl adsnine, mercaptopolylysine, vincristine, busulfan, chlorambucil, melphalan (e.g., PAM, L-PAM or phenylalanine mustard), mercaptopurine, mitotane, procarbazine hydrochloride dactinomycin (actinomycin D), daunorubicinhydrochloride, doxorubicin hydrochloride, mitomycin, plicamycin (mithramycin), aminoglutethimide, estramustine phosphate sodium, flutamide, leuprolide acetate, megestrol acetate, tamoxifen citrate, testolactone, trilostane, amsacrine (m-AMSA), asparaginase (L-asparaginase), Erwinaasparaginase, etoposide (VP-16), interferon alpha-2a, interferon alpha-2b, teniposide (VM-26), vinblastine sulfate (VLB), vincristine sulfate, bleomycin, bleomycin sulfate, methotrexate, adriamycin, and arabinosyl; blood products such as parenteral iron, hemin; biological response modifiers such as muramyldipeptide, muramyltripeptide, microbial cell wall components, lymphokines (e.g., bacterial endotoxin such as lipopolysaccharide, macrophage activation factor), sub-units of bacteria (such as Mycobacteria, Corynebacteria), the synthetic dipeptide N-acetyl-muramyl-L-alanyl-D-isog-lutamine; anti-fungalagents such as ketoconazole, nystatin, griseofulvin, flucytosine (5-fc), miconazole, amphotericin B, ricin, and beta-lactam antibiotics (e.g., penicillin, ampicillin, sulfazecin); hormones such as growth hormone, PDGF, EGF, CSF, GM-CSF, melanocyte stimulating hormone, estradiol, beclomethasone dipropionate, betamethasone, betamethasone acetate and betamethasone sodium phosphate, vetamethasonedisodiumphosphate, vetamethasone sodium phosphate, cortisone acetate, dexamethasone, dexamethasone acetate, dexamethasone sodium phosphate, flunsolide, hydrocortisone, hydrocortisone acetate, hydrocortisone cypionate, hydrocortisone sodium phosphate, hydrocortisone sodium succinate, methylprednisolone, methylprednisolone acetate, methylprednisolone sodium succinate, paramethasone acetate, prednisolone, prednisoloneacetate, prednisolone sodium phosphate, prednisolone rebutate, prednisone, triamcinolone, triamcinolone acetonide, triamcinolone diacetate, triamcinolone hexacetonide and fludrocortisone acetate; vitamins such vitamin C, E, A, K, ascyanocobalamin, neinoic acid, retinoids and derivatives such as retinolpalmitate, and alpha-tocopherol(s); peptides (e.g., T cell epitopes such as MAGE, GAGE, DAGE, etc.); proteins, such as manganese super oxide dimutase, alcohol dehydrogenase, nitric oxide synthase; enzymes such as alkaline phosphatase; anti-allergic agents such as amelexanox; anti-coagulation agents such as phenprocoumon and heparin; circulatory drugs such as propranolol; metabolic potentiators such asglutathione; antituberculars such as para-aminosalicylic acid, isoniazid, capreomycin sulfate cycloserine, ethambutol hydrochloride ethionamide, pyrazinamide, rifampin, and streptomycin sulfate; antivirals such as acyclovir, amantadine azidothymidine (AZT or Zidovudine), Ribavirin andvidarabine monohydrate (adenine arabinoside, ara-A); antianginals such asdiltiazem, nifedipine, verapamil, erythrityl tetranitrate, isosorbidedinitrate, nitroglycerin (glyceryl trinitrate) and pentaerythritoltetranitrate; anticoagulants such as phenprocoumon, heparin; antibiotics such as dapsone, chloramphenicol, neomycin, cefaclor, cefadroxil, cephalexin, cephradine erythromycin, clindamycin, lincomycin, amoxicillin, ampicillin, bacampicillin, carbenicillin, dicloxacillin, cyclacillin, picloxacillin, hetacillin, methicillin, nafcillin, oxacillin, penicillin G, penicillin V, ticarcillin rifampin and tetracycline; antiinflammatories such as difunisal, ibuprofen, indomethacin, meclofenamate, mefenamic acid, naproxen, oxyphenbutazone, phenylbutazone, piroxicam, sulindac, tolmetin, aspirin and salicylates; antiprotozoans such as chloroquine, hydroxychloroquine, metronidazole, quinine and meglumine antimonate; antirheumatics such as penicillamine; narcotics such as paregoric; opiates such as codeine, heroin, methadone, morphine and opium; cardiac glycosides such as deslanoside, digitoxin, digoxin, digitalin and *digitalis*; neuromuscular blockers such as atracurium besylate, gallamine triethiodide, hexafluorenium bromide, metocurine iodide, pancuronium bromide, succinylcholine chloride (suxamethonium chloride), tubocurarine chloride and vecuronium bromide; sedatives (hypnotics) such as amobarbital, amobarbital sodium, aprobarbital, butabarbital sodium, chloral hydrate, ethchlorvynol, ethinamate, flurazepam hydrochloride, glutethimi de, methotrimeprazine hydrochloride, methyprylon, midazolam hydrochloride, paraldehyde, pentobarbital, pentobarbital sodium, phenobarbital sodium, secobarbital sodium, talbutal, temazepam and triazolam; local anesthetics such as bupivacaine hydrochloride, chloroprocaine hydrochloride, etidocainehydrochloride, lidocaine hydrochloride, mepivacaine hydrochloride, procainehydrochloride and tetracaine hydrochloride; general anesthetics such asdroperidol, etomidate, fentanyl citrate with droperidol, ketaminehydrochloride, methohexital sodium and thiopental sodium; and radioactive particles or ions such as strontium, iodide rhenium and yttrium, and combinations and mixtures thereof.

In addition to the polynucleotides of the disclosure, prodrugs may be pre-loaded into the liposomes prior to attachment to the microbubbles. Prodrugs are well known in the art and may include inactive drug precursors that are metabolized to form active drugs. The skilled artisan will recognize suitable prodrugs (and if necessary their salt forms) as described by, e.g., in Sinkula, et al., 1975, the relevant portions of which are incorporated herein by reference. Prodrugs, for example, may include inactive forms of the active drugs wherein a chemical group is present on the prodrug which renders it inactive and/or confers solubility or some other property to the drug. In this form, the prodrugs are generally inactive, but once the chemical group has been cleaved from the prodrug, by heat, cavitation, pressure, and/or by enzymes in the surrounding environment or otherwise, the active drug is generated. Such prodrugs are well described in the art, and comprise a wide variety of drugs bound to chemical groups through bonds such as esters to short, medium or long chain aliphatic carbonates, hemiesters of organic phosphate, pyrophosphate, sulfate, amides, amino acids, azo bonds, carbamate, phosphamide, glucosiduronate, N-acetylglucosamine and beta-glucoside. Examples of drugs with the parent molecule and the reversible modification or linkage are as follows: convallatoxin with ketals, hydantoin with alkyl esters, chlorphenesin with glycine or alanins esters, acetaminophen with caffeine complex, acetylsalicylic acid with THAM salt, acetylsalicylic acid with acetamidophenyl ester, naloxone with sulfateester, 15-methylprostaglandin F sub 2 with methyl ester, procaine with polyethylene glycol, erythromycin with alkyl esters, clindamycin with alkylesters or phosphate esters, tetracycline with betains salts, 7-acylaminocephalosporins with ring-substituted acyloxybenzyl esters, nandrolone with phenylproprionate decanoate esters, estradiol with enolether acetal, methylprednisolone with acetate esters, testosterone with n-acetylglucosaminide glucosiduronate (trimethylsilyl) ether, cortisol or prednisolone or dexamethasone with 21-phosphate esters. Prodrugs may also be designed as reversible drug derivatives and used as modifiers to enhance drug transport to site-specific tissues. Examples of carrier molecules with reversible modifications or linkages to influence transport to a site specific tissue and for enhanced therapeutic effect include isocyanate with haloalkyl nitrosurea, testosterone with propionateester, methotrexate (3-5'-dichloromethotrexat-e) with dialkyl esters, cytosine arabinoside with 5'-acylate, nitrogen mustard (2,2'-dichloro-N-methyldiethylamine), nitrogen mustard with aminomethyltetracycline, nitrogen mustard with cholesterol or estradiol ordehydroepiandrosterone esters and nitrogen mustard with azobenzene.

The skilled artisan will recognize that a particular chemical group may be modified in any given agent may be selected to influence the partitioning of the drug into either the shell or the interior of the microbubbles. The bond selected to link the chemical group to the drug may be selected to have the desired rate of metabolism, e.g., hydrolysis in the case of ester bonds in the presence of serum esterases after release from the microbubbles. Additionally, the particular chemical group may be selected to influence the biodistribution of the drug employed in the microbubbles, e.g., N,N-bis(2-chloroethyl)-phosphorodiamidic acid with cyclic phosphoramide. Additionally, the prodrugs employed within the microbubbles may be designed to contain reversible derivatives that are used as modifiers of duration of activity to provide, prolong or depot action effects.

For example, nicotinic acid may be modified with dextran and carboxymethlydextran esters, streptomycin with alginic acid salt, dihydrostreptomycin with pamoate salt, cytarabine (ara-C) with 5'-adamantoats ester, ara-adenosine (ara-A) with 5-palmirate and 5'-benzoate esters, amphotericin B with methyl esters, testosterone with 17-beta-alkyl esters, estradiol with formate ester, prostaglandin with 2-(4-imidazolyl) ethylamine salt, dopamine with amino acid amides, chloramphenicol with mono- and bis(trimethylsilyl) ethers, and cycloguanil with pamoate salt. In this form, a depot or reservoir of long-acting drug may be released in vivo from the prodrug bearing microbubbles. The particular chemical structure of the therapeutics may be selected or modified to achieve a desired solubility such that the therapeutic is loaded into a liposome prior to attaching or loading in, to, at or about a microbubble. Similarly, other therapeutics may be formulated with a hydrophobic group which is aromatic or sterol in structure to incorporate into the surface of the microbubble.

Cationic liposomes suitable for use in the present disclosure comprise one or more monocationic or polycationic lipids, optionally combined with one or more neutral or helper lipids. The cationic lipids suitable for the present disclosure can be obtained commercially or made by methods known in the art. Cationic lipids suitable for the formation of cationic liposomes are well known in the art and include but are not limited to any phospholipid-related materials, such as lecithin, phosphatidylethanolamine, lysolecithin, lysophosphatidylethanolamine, phosphatidylserine, phosphatidylinositol, sphingomyelin, cephalin, cardiolipin, phosphatidic acid, cerebrosides, dicetylphosphate, dioleoylphosphatidylcholine (DOPC), dipalmitoylphosphatidylcholine (DPPC), dioleoylphosphatidylglycerol (DOPG), dipalmitoylphosphatidylglycerol (DPPG), dipalmitoylphosphatidylethanolamine 5-carboxyspermylamide (DPPES), dioleoylphosphatidylethanolamine (DOPE), palmitoyloleoylphosphatidylcholine (POPC), palmitoyloleoylphosphatidylethanolamine (POPE) and dioleoylphosphatidyl-ethanolamine 4-(N-maleimidomethyl)cyclohexane-1-carboxylate (DOPE-mal). Additional non-phosphorous containing lipids include but are not limited to stearylamine, dodecylamine, hexadecylamine, acetyl palmitate, glycerol ricinoleate, hexadecyl stearate, isopropyl myristate, amphoteric acrylic polymers, triethanolamine-lauryl sulfate, alkylaryl sulfate polyethyloxylated fatty acid amides, dioctadecyldimethyl ammonium bromide and steroids such as cholesterol, ergosterol, ergosterol B1, B2 and B3, androsterone, cholic acid, desoxycholic acid, chenodesoxycholic acid, lithocholic acid, N-[1-(2,3-dioleoyloxy)propyl]-N,N,N-trimethylammonium chloride (DOTMA), 1,2-bis(oleoyloxy)-3-3-(trimethylammonia)propane (DOTAP), and 5-carboxyspermylglycine dioctadecylamide (DOGS). A preferred liposome formulation comprises the polycationic lipid 2,3-dioleyloxy-N-[2-(sperminecarboxaido)ethyl]-N,N-dim-ethyl-1-propanaminu-m trifluoroacetate (DOSPA) and the neutral lipid dioleoyl phosphatidylethanolamine (DOPE) at (3:1, w/w), and mixtures and combinations thereof.

In the method of the present disclosure, the cationic liposomes are loaded with the polynucleotide, at least. In one embodiment, a cationic lipid formulation of one or more lipids dissolved in one or more organic solvents is first dried or lyophilized to remove the organic solvent(s), resulting in a lipid film. Just prior to use, the lipid film is mixed with a polynucleotide suitable for the present disclosure suspended in a suitable aqueous medium for forming liposomes from the dried lipid film. For example, water, an aqueous buffer solution, or a tissue culture media can be used for rehydration of the lipid film. A suitable buffer is phosphate buffered saline, i.e., 10 mM potassium phosphate having a pH of 7.4 in 0.9% NaCl solution. In another embodiment, the dried lipid film is rehydrated with a suitable aqueous medium to form liposomes before the addition of the bioactive agent. This method is preferred when the bioactive agent comprises genetic material. The incorporation of the bioactive agent into the cationic liposomes is often performed at a temperature within the range of about 0 to 30° C., e.g., room temperature, in about 5, 10-20 minutes.

In the methods of the present disclosure, the cationic liposomes with attached bioactive agent(s) (such as a polynucleotide) are then loaded onto neutrally charged microbubbles. In a preferred embodiment, this is accomplished by adding to the cationic liposomes with attached bioactive agent(s) a lipid composition suitable for making the microbubble shell, mixing well, and then adding an appropriate gas for encapsulation by the microbubble shell, followed by vigorous shaking for about 5 to 60 seconds, preferably for about 20 seconds. In a preferred method, the lipid composition is kept at about 0 to 30° C. before the addition of the cationic liposomes with attached bioactive agent(s).

To form the microbubble shell, any biocompatible lipid of natural or synthetic origin known to be useful in ultrasound-targeted microbubble destruction are contemplated as part of the present disclosure. Exemplary lipids can be found in International Application No. WO 2000/45856 and include but are not limited to fatty acids, phosphatides, glycolipids, glycosphingolipids, sphingolipids, aliphatic alcohols, aliphatic waxes, terpenes, sesquiterpenes, and steroids. Examples of lipids are phosphocholines, phosphatidylcholines, phosphatidylethanolamines, phosphatidylserines, phosphatidylglycerols, and phosphatidylinositol. A particular lipid is 1,2-palmitoyl-sn-glycero-3-phosphocholine or 1,2-palmitoyl-sn-glycero-phosphatidylethanolamine. The specific lipid is L-1,2-palmitoyl-sn-glycero-3-phosphocholine and L-1,2-palmitoyl-sn-glycero-phosphatidylethanolamine.

Gases suitable for the present disclosure are generally inert and biocompatible, including but not limited to air; carbon dioxide; nitrogen; oxygen; fluorine; noble gases such as helium, neon, argon, and xenon; sulfur-based gases; fluorinated gases; and mixtures thereof. The gas may be a perfluoropropane, e.g., octafluoropropane.

As is well known to those versed in the art, targeting ligands can also be attached to the microbubbles to confer additional tissue specificity. Such ligands could include monoclonal antibodies, peptides, polypeptides, proteins, glycoproteins, hormones or hormone analogues, monosaccharides, polysaccharides, steroids or steroid analogues, vitamins, cytokines, or nucleotides.

The delivery methods of the present disclosure comprising neutrally charged microbubbles loaded with nanosphere cationic liposomes containing one or more bioactive agents provide all the advantages of an ultrasound-targeted microbubble delivery system combined with all the advantages of a liposome delivery system. The ultrasound-targeted microbubble delivery system allows for delivery of a drug/gene bioactive agent to a specific organ or tissue while minimizing the exposure of other organs or tissues to the bioactive agent. During delivery, the bioactive agent(s) remain within the protective cationic liposome, which shields the bioactive agent(s) from proteases, nucleases, lipases, carbohydrate-cleaving enzymes, free radicals, or other chemical alterations. This method increases the delivery of the bioactive agent and its bioavailability to the target tissue. For example, in the delivery of neutrally charged microbubbles loaded with nanosphere cationic liposomes containing plasmid DNA, the level of gene expression at the target site is increased over the level of expression possible with either a microbubble delivery or a liposome delivery of the same plasmid DNA.

In one aspect, the present disclosure is a method of treating a mammal in need of such treatment comprising administration of an effective amount of a composition comprising neutrally charged lipid microbubbles loaded with nanosphere cationic liposomes containing a bioactive agent (such as a GLP-1 polynucleotide) via ultrasound-targeted microbubble destruction. Administration of the composition comprising neutrally charged lipid microbubbles loaded with nanosphere cationic liposomes containing a bioactive agent and the ultrasound-targeted microbubble destruction of these microbubbles to release the bioactive agent can be accomplished by any means known in the art. Repeat administration of the microbubbles is possible, particularly to prolong the duration of the therapeutic effect. For example, repeated transfection of cardiomyocytes by ultrasound targeted microbubble destruction has been shown to extend the peak duration of luciferase activity in the heart from 4 days to 12 days (Bekeredjian et al, 2003). This potentially allows for the duration of gene or drug delivery to be tailored to the specific biological or medical need.

VI. Nucleic Acid-Based Expression Systems

Glucagon-like peptide (GLP)-1 may be provided as a polynucleotide in the UTMD system to a target tissue, such as the heart. In specific embodiments, the GLP-1 polynucleotide is provided in an expression vector for use in the UTMD system. Also, TB4 may be provided as a polynucleotide in the UTMD system to a target tissue, such as the heart. In specific embodiments, the TB4 polynucleotide is provided in an expression vector for use in the UTMD system. In certain embodiments, the GLP-1 and TB4 polynucleotides are the same molecule, although in some embodiments the GLP-1 and TB4 polynucleotides are different molecules. When GLP-1 and TB4 is expressed from the same polynucleotide, they may have the same or different regulatory regions for their expression.

In particular embodiments, an expression vector for use in the UTMD system may comprise one or more suitable restriction enzyme digestion sequences, start codons, stop codons, nuclear localization signals, protease cutting codons, selectable markers, origins of replication, regulatory regions, multiple cloning sites, and a combination thereof. Such moieties may be positioned in the expression vector in any suitable order.

As an exemplary embodiment, the following pattern of GLP-1 construct may be used in an expression vector:
  Xho1-Start codon-Furin cutting codon-GLP-1(7-37)-NLS-Stop codon-Not1

```
NLS sequence:
                                         (SEQ ID NO: 3)
5'-CCT-AAA-AAA-AAG-CGG-AAG-GTC-3'
```

In one embodiment, the following GLP-1 construct may be employed in an expression vector:
  Xho-Startcodon-Furincuttingcodon-GLP-1(7-37)-NLS-Stopcodon-Not1

```
                                         (SEQ ID NO: 4)
5'-AAA-CTC-GAG-ATG-CGT-CAA-CGT-CGT-CAT-GCT-GAA-

GGG-ACC-TTT-ACC-AGT-GAT-GTG-AGT-TCT-TAC-TTG-GAG-

GGC-CAG-GCA-GCA-AAG-GAA-TTC-ATT-GCT-TGG-CTG-GTG-

AAA-GGC-CGA-GGA-CCT-AAA-AAA-AAG-CGG-AAG-GTC-TAG-

GCG-GCC-GCA-AAA-3'
```

A. Vectors

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques (see, for example, Maniatis et al., 1988 and Ausubel et al., 1994, both incorporated herein by reference).

The term "expression vector" refers to any type of genetic construct comprising a nucleic acid coding for a RNA capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host cell. In addition to control sequences that govern transcription and translation, vectors and expression vectors may contain nucleic acid sequences that serve other functions as well and are described infra.

a. Promoters and Enhancers

A "promoter" is a control sequence that is a region of a nucleic acid sequence at which initiation and rate of transcription are controlled. It may contain genetic elements at which regulatory proteins and molecules may bind, such as RNA polymerase and other transcription factors, to initiate the specific transcription a nucleic acid sequence. The phrases "operatively positioned," "operatively linked," "under control," and "under transcriptional control" mean that a promoter is in a correct functional location and/or orientation in relation to a nucleic acid sequence to control transcriptional initiation and/or expression of that sequence.

In embodiments of the disclosure, a CMV promoter or a tissue-specific promoter may be employed. The tissue-specific promoter may be a cardiac tissue specific promoter. Examples of cardiac tissue specific promoters include ventricle-specific myosin light chain-2 (mlc-2v); alpha-myosin heavy chain (α-MHC). Another example of a promoter that may be employed includes the insulin promoter, including the rat insulin promoter.

A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30-110 bp upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be one naturally associated with a nucleic acid sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression. For example, promoters that are most commonly used in recombinant DNA construction include the β-lactamase (penicillinase), lactose and tryptophan (trp) promoter systems. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202 and 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the organelle, cell type, tissue, organ, or organism chosen for expression. Those of skill in the art of molecular biology generally know the use of promoters, enhancers, and cell type combinations for protein expression, (see, for example Sambrook et al. 1989, incorporated herein by reference). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Additionally any promoter/enhancer combination (as per, for example, the Eukaryotic Promoter Data Base EPDB, http://www.epd.isb-sib.ch/) could also be used to drive expression. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

b. Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the disclosure, the use of internal ribosome entry sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, each herein incorporated by reference).

c. Multiple Cloning Sites

Vectors can include a multiple cloning site (MCS), which is a nucleic acid region that contains multiple restriction enzyme sites, any of which can be used in conjunction with standard recombinant technology to digest the vector (see, for example, Carbonelli et al., 1999, Levenson et al., 1998, and Cocea, 1997, incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

d. Splicing Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression (see, for example, Chandler et al. 1997, herein incorporated by reference.)

e. Termination Signals

The vectors or constructs of the present disclosure will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message. The terminator and/or polyadenylation site elements can serve to enhance message levels and to minimize read through from the cassette into other sequences.

Terminators contemplated for use in the disclosure include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

f. Polyadenylation Signals

In expression, particularly eukaryotic expression, one will typically include a polyadenylation signal to effect proper polyadenylation of the transcript. The nature of the polyadenylation signal is not believed to be crucial to the successful practice of the disclosure, and any such sequence may be employed. Preferred embodiments include the SV40 polyadenylation signal or the bovine growth hormone polyadenylation signal, convenient and known to function well in various target cells. Polyadenylation may increase the stability of the transcript or may facilitate cytoplasmic transport.

g. Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

h. Selectable and Screenable Markers

In certain embodiments of the disclosure, cells containing a nucleic acid construct of the present disclosure may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

i. Plasmid Vectors

In certain embodiments, a plasmid vector is contemplated for use to transform a host cell. In general, plasmid vectors containing replicon and control sequences which are derived from species compatible with the host cell are used in connection with these hosts. The vector ordinarily carries a replication site, as well as marking sequences which are capable of providing phenotypic selection in transformed cells. In a non-limiting example, *E. coli* is often transformed using derivatives of pBR322, a plasmid derived from an *E. coli* species. pBR322 contains genes for ampicillin and tetracycline resistance and thus provides easy means for identifying transformed cells. The pBR plasmid, or other microbial plasmid or phage must also contain, or be modified to contain, for example, promoters which can be used by the microbial organism for expression of its own proteins.

In addition, phage vectors containing replicon and control sequences that are compatible with the host microorganism can be used as transforming vectors in connection with these hosts. For example, the phage lambda GEM™-11 may be utilized in making a recombinant phage vector which can be used to transform host cells, such as, for example, *E. coli* LE392.

Genomic integrated plasmids, such as piggybac or sleeping beauty transposon gene delivery plasmids, may be employed for long term transgenic expression of GLP-1 gene in heart or other organ.

Further useful plasmid vectors include pIN vectors (Inouye et al., 1985); and pGEX vectors, for use in generating glutathione S-transferase (GST) soluble fusion proteins for later purification and separation or cleavage. Other suitable fusion proteins are those with β-galactosidase, ubiquitin, and the like.

Bacterial host cells, for example, *E. coli*, comprising the expression vector, are grown in any of a number of suitable media, for example, LB. The expression of the recombinant protein in certain vectors may be induced, as would be understood by those of skill in the art, by contacting a host cell with an agent specific for certain promoters, e.g., by adding IPTG to the media or by switching incubation to a higher temperature. After culturing the bacteria for a further period, generally of between 2 and 24 h, the cells are collected by centrifugation and washed to remove residual media.

j. Viral Vectors

The ability of certain viruses to infect cells or enter cells via receptor-mediated endocytosis, and to integrate into host cell genome and express viral genes stably and efficiently have made them attractive candidates for the transfer of foreign nucleic acids into cells (e.g., mammalian cells). Non-limiting examples of virus vectors that may be used to deliver a nucleic acid of the present disclosure are described below.

1. Adenoviral Vectors

A particular method for delivery of the nucleic acid involves the use of an adenovirus expression vector. Although adenovirus vectors are known to have a low capacity for integration into genomic DNA, this feature is counterbalanced by the high efficiency of gene transfer afforded by these vectors. "Adenovirus expression vector" is meant to include those constructs containing adenovirus sequences sufficient to (a) support packaging of the construct and (b) to ultimately express a tissue or cell-specific construct that has been cloned therein. Knowledge of the genetic organization or adenovirus, a 36 kb, linear, double-stranded DNA virus, allows substitution of large pieces of adenoviral DNA with foreign sequences up to 7 kb (Grunhaus and Horwitz, 1992).

2. AAV Vectors

The nucleic acid may be introduced into the cell using adenovirus assisted transfection. Increased transfection efficiencies have been reported in cell systems using adenovirus coupled systems (Kelleher and Vos, 1994; Cotten et al., 1992; Curiel, 1994). Adeno-associated virus (AAV) is an attractive vector system for use in embodiments of the present disclosure as it has a high frequency of integration and it can infect nondividing cells, thus making it useful for delivery of genes into mammalian cells, for example, in tissue culture (Muzyczka, 1992) or in vivo. AAV has a broad host range for infectivity (Tratschin et al., 1984; Laughlin et al., 1986; Lebkowski et al., 1988; McLaughlin et al., 1988). Details concerning the generation and use of rAAV vectors are described in U.S. Pat. Nos. 5,139,941 and 4,797,368, each incorporated herein by reference.

3. Retroviral Vectors

Retroviruses have promise as delivery vectors due to their ability to integrate their genes into the host genome, transferring a large amount of foreign genetic material, infecting a broad spectrum of species and cell types and of being packaged in special cell-lines (Miller, 1992).

In order to construct a retroviral vector, a nucleic acid is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into a special cell line (e.g., by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

Lentiviruses are complex retroviruses, which, in addition to the common retroviral genes gag, pol, and env, contain other genes with regulatory or structural function. Lentiviral vectors are well known in the art (see, for example, Naldini et al., 1996; Zufferey et al., 1997; Blomer et al., 1997; U.S. Pat. Nos. 6,013,516 and 5,994,136). Some examples of lentivirus include the Human Immunodeficiency Viruses: HIV-1, HIV-2 and the Simian Immunodeficiency Virus: SIV. Lentiviral vectors have been generated by multiply attenuating the HIV virulence genes, for example, the genes env, vif, vpr, vpu and nef are deleted making the vector biologically safe.

Recombinant lentiviral vectors are capable of infecting non-dividing cells and can be used for both in vivo and ex vivo gene transfer and expression of nucleic acid sequences. For example, recombinant lentivirus capable of infecting a non-dividing cell wherein a suitable host cell is transfected with two or more vectors carrying the packaging functions, namely gag, pol and env, as well as rev and tat is described in U.S. Pat. No. 5,994,136, incorporated herein by reference. One may target the recombinant virus by linkage of the envelope protein with an antibody or a particular ligand for targeting to a receptor of a particular cell-type. By inserting a sequence (including a regulatory region) of interest into the viral vector, along with another gene which encodes the ligand for a receptor on a specific target cell, for example, the vector is now target-specific.

4. Other Viral Vectors

Other viral vectors may be employed as vaccine constructs in the present disclosure. Vectors derived from viruses such as vaccinia virus (Ridgeway. 1988; Baichwal and Sugden, 1986; Coupar et al., 1988), sindbis virus, cytomegalovirus and herpes simplex virus may be employed. They offer several attractive features for various mammalian cells (Friedmann, 1989; Ridgeway, 1988; Baichwal and Sugden, 1986; Coupar et al., 1988; Horwich et al., 1990).

5. Delivery Using Modified Viruses

A nucleic acid to be delivered may be housed within an infective virus that has been engineered to express a specific binding ligand. The virus particle will thus bind specifically to the cognate receptors of the target cell and deliver the contents to the cell. A novel approach designed to allow specific targeting of retrovirus vectors was developed based on the chemical modification of a retrovirus by the chemical addition of lactose residues to the viral envelope. This modification can permit the specific infection of hepatocytes via sialoglycoprotein receptors.

Another approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

B. Vector Delivery and Cell Transformation

Suitable methods for nucleic acid delivery for transformation of an organelle, a cell, a tissue or an organism for use with the current disclosure are believed to include virtually any method by which a nucleic acid (e.g., DNA) can be introduced into an organelle, a cell, a tissue or an organism, as described herein or as would be known to one of ordinary skill in the art. Such methods include, but are not limited to, direct delivery of DNA such as by ex vivo transfection (Wilson et al., 1989, Nabel et al, 1989), by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harlan and Weintraub, 1985; U.S. Pat. No. 5,789, 215, incorporated herein by reference); by electroporation (U.S. Pat. No. 5,384,253, incorporated herein by reference; Tur-Kaspa et al. 1986; Potter et al., 1984); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991) and receptor-mediated transfection (Wu and Wu, 1987; Wu and Wu, 1988); by microprojectile bombardment (PCT Application Nos. WO 94/09699 and 95/06128; U.S. Pat. Nos. 5,610,042; 5,322, 783 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); by Agrobacterium-mediated transformation (U.S. Pat. Nos. 5,591,616 and 5,563,055, each incorporated herein by reference); by PEG-mediated transformation of protoplasts (Omirulleh et al., 1993; U.S. Pat. Nos. 4,684,611 and 4,952,500, each incorporated herein by reference); by desiccation/inhibition-mediated DNA uptake (Potrykus et al., 1985), and any combination of such methods. Through the application of techniques such as these, organelle(s), cell(s), tissue(s) or organism(s) may be stably or transiently transformed.

a. Ex Vivo Transformation

Methods for tranfecting vascular cells and tissues removed from an organism in an ex vivo setting are known to those of skill in the art. For example, cannine endothelial cells have been genetically altered by retroval gene tranfer in vitro and transplanted into a canine (Wilson et al., 1989). In another example, yucatan minipig endothelial cells were tranfected by retrovirus in vitro and transplanted into an artery using a double-ballonw catheter (Nabel et al., 1989). Thus, it is contemplated that cells or tissues may be removed and tranfected ex vivo using the nucleic acids of the present disclosure. In particular aspects, the transplanted cells or tissues may be placed into an organism. In preferred facets, a nucleic acid is expressed in the transplated cells or tissues.

b. Injection

In certain embodiments, a nucleic acid may be delivered to an organelle, a cell, a tissue or an organism via one or more injections (i.e., a needle injection), such as, for example, subcutaneously, intradermally, intramuscularly, intervenously, intraperitoneally, etc. Methods of injection of vaccines are well known to those of ordinary skill in the art (e.g., injection of a composition comprising a saline solution). Further embodiments of the present disclosure include the introduction of a nucleic acid by direct microinjection. Direct microinjection has been used to introduce nucleic acid constructs into Xenopus oocytes (Harland and Weintraub, 1985).

c. Electroporation

In certain embodiments of the present disclosure, a nucleic acid is introduced into an organelle, a cell, a tissue or an organism via electroporation. Electroporation involves the exposure of a suspension of cells and DNA to a high-voltage electric discharge. In some variants of this method, certain cell wall-degrading enzymes, such as pectin-degrading enzymes, are employed to render the target recipient cells more susceptible to transformation by electroporation than untreated cells (U.S. Pat. No. 5,384,253, incorporated herein by reference). Alternatively, recipient cells can be made more susceptible to transformation by mechanical wounding.

Transfection of eukaryotic cells using electroporation has been quite successful. Mouse pre-B lymphocytes have been transfected with human kappa-immunoglobulin genes (Potter et al., 1984), and rat hepatocytes have been transfected with the chloramphenicol acetyltransferase gene (Tur-Kaspa et al., 1986) in this manner.

To effect transformation by electroporation in cells such as, for example, plant cells, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wounding in a controlled manner. Examples of some species which have been transformed by electroporation of intact cells include maize (U.S. Pat. No. 5,384,253; Rhodes et al., 1995; D'Halluin et al., 1992), wheat (Zhou et al., 1993), tomato (Hou and Lin, 1996), soybean (Christou et al., 1987) and tobacco (Lee et al., 1989).

One also may employ protoplasts for electroporation transformation of plant cells (Bates, 1994; Lazzeri, 1995). For example, the generation of transgenic soybean plants by electroporation of cotyledon-derived protoplasts is described by Dhir and Widholm in International Patent Application No. WO 9217598, incorporated herein by reference. Other examples of species for which protoplast transformation has been described include barley (Lazerri, 1995), sorghum (Battraw et al., 1991), maize (Bhattacharjee et al., 1997), wheat (He et al., 1994) and tomato (Tsukada, 1989).

d. Calcium Phosphate

In other embodiments of the present disclosure, a nucleic acid is introduced to the cells using calcium phosphate precipitation. Human KB cells have been transfected with adenovirus 5 DNA (Graham and Van Der Eb, 1973) using this technique. Also in this manner, mouse L(A9), mouse C127, CHO, CV-1, BHK, NIH3T3 and HeLa cells were transfected with a neomycin marker gene (Chen and Okayama, 1987), and rat hepatocytes were transfected with a variety of marker genes (Rippe et al., 1990).

e. DEAE-Dextran

In another embodiment, a nucleic acid is delivered into a cell using DEAE-dextran followed by polyethylene glycol. In this manner, reporter plasmids were introduced into mouse myeloma and erythroleukemia cells (Gopal, 1985).

f. Sonication Loading

Additional embodiments of the present disclosure include the introduction of a nucleic acid by direct sonic loading. LTK$^-$ fibroblasts have been transfected with the thymidine kinase gene by sonication loading (Fechheimer et al., 1987).

g. Liposome-Mediated Transfection

In a further embodiment of the disclosure, a nucleic acid may be entrapped in a lipid complex such as, for example, a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated is an nucleic acid complexed with Lipofectamine (Gibco BRL) or Superfect (Qiagen).

Liposome-mediated nucleic acid delivery and expression of foreign DNA in vitro has been very successful (Nicolau and Sene, 1982; Fraley et al., 1979; Nicolau et al., 1987). The feasibility of liposome-mediated delivery and expression of foreign DNA in cultured chick embryo, HeLa and hepatoma cells has also been demonstrated (Wong et al., 1980).

In certain embodiments of the disclosure, a liposome may be complexed with a hemagglutinating virus (HVJ). This has been shown to facilitate fusion with the cell membrane and promote cell entry of liposome-encapsulated DNA (Kaneda et al., 1989). In other embodiments, a liposome may be complexed or employed in conjunction with nuclear non-histone chromosomal proteins (HMG-1) (Kato et al., 1991). In yet further embodiments, a liposome may be complexed or employed in conjunction with both HVJ and HMG-1. In other embodiments, a delivery vehicle may comprise a ligand and a liposome.

h. Receptor Mediated Transfection

Still further, a nucleic acid may be delivered to a target cell via receptor-mediated delivery vehicles. These take advantage of the selective uptake of macromolecules by receptor-mediated endocytosis that will be occurring in a target cell. In view of the cell type-specific distribution of various receptors, this delivery method adds another degree of specificity to the present disclosure.

Certain receptor-mediated gene targeting vehicles comprise a cell receptor-specific ligand and a nucleic acid-binding agent. Others comprise a cell receptor-specific ligand to which the nucleic acid to be delivered has been operatively attached. Several ligands have been used for receptor-mediated gene transfer (Wu and Wu, 1987; Wagner et al., 1990; Perales et al., 1994; Myers, EPO 0273085), which establishes the operability of the technique. Specific delivery in the context of another mammalian cell type has been described (Wu and Wu, 1993; incorporated herein by reference). In certain aspects of the present disclosure, a ligand will be chosen to correspond to a receptor specifically expressed on the target cell population.

In other embodiments, a nucleic acid delivery vehicle component of a cell-specific nucleic acid targeting vehicle may comprise a specific binding ligand in combination with a liposome. The nucleic acid(s) to be delivered are housed within the liposome and the specific binding ligand is functionally incorporated into the liposome membrane. The liposome will thus specifically bind to the receptor(s) of a target cell and deliver the contents to a cell. Such systems have been shown to be functional using systems in which, for example, epidermal growth factor (EGF) is used in the receptor-mediated delivery of a nucleic acid to cells that exhibit upregulation of the EGF receptor.

In still further embodiments, the nucleic acid delivery vehicle component of a targeted delivery vehicle may be a liposome itself, which will preferably comprise one or more lipids or glycoproteins that direct cell-specific binding. For example, lactosyl-ceramide, a galactose-terminal asialganglioside, have been incorporated into liposomes and observed an increase in the uptake of the insulin gene by hepatocytes (Nicolau et al., 1987). It is contemplated that the tissue-specific transforming constructs of the present disclosure can be specifically delivered into a target cell in a similar manner.

i. Microprojectile Bombardment

Microprojectile bombardment techniques can be used to introduce a nucleic acid into at least one, organelle, cell, tissue or organism (U.S. Pat. No. 5,550,318; U.S. Pat. No. 5,538,880; U.S. Pat. No. 5,610,042; and PCT Application WO 94/09699; each of which is incorporated herein by reference). This method depends on the ability to accelerate DNA-coated microprojectiles to a high velocity allowing them to pierce cell membranes and enter cells without killing them (Klein et al., 1987). There are a wide variety of microprojectile bombardment techniques known in the art, many of which are applicable to the disclosure.

Microprojectile bombardment may be used to transform various cell(s), tissue(s) or organism(s), such as for example any plant species. Examples of species which have been transformed by microprojectile bombardment include monocot species such as maize (PCT Application WO 95/06128), barley (Ritala et al., 1994; Hensgens et al., 1993), wheat (U.S. Pat. No. 5,563,055, incorporated herein by reference), rice (Hensgens et al., 1993), oat (Torbet et al., 1995; Torbet et al., 1998), rye (Hensgens et al., 1993), sugarcane (Bower et al., 1992), and sorghum (Casas et al., 1993; Hagio et al., 1991); as well as a number of dicots including tobacco (Tomes et al., 1990; Buising and Benbow, 1994), soybean (U.S. Pat. No. 5,322,783, incorporated herein by reference), sunflower (Knittel et al. 1994), peanut (Singsit et al., 1997), cotton (McCabe and Martinell, 1993), tomato (VanEck et al. 1995), and legumes in general (U.S. Pat. No. 5,563,055, incorporated herein by reference).

In this microprojectile bombardment, one or more particles may be coated with at least one nucleic acid and delivered into cells by a propelling force. Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold particles or beads. Exemplary particles include those comprised of tungsten, platinum, and preferably, gold. It is contemplated that in some instances DNA precipitation onto metal particles would not be necessary for DNA delivery to a recipient cell using microprojectile bombardment. However, it is contemplated that particles may contain DNA rather than be coated with DNA. DNA-coated particles may increase the level of DNA delivery via particle bombardment but are not, in and of themselves, necessary.

For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into a cell (e.g., a plant cell) by acceleration is the Biolistics Particle Delivery System, which can be used to propel particles coated with DNA or cells through a screen, such as a stainless steel or Nytex screen, onto a filter surface covered with cells, such as for example, a monocot plant cells cultured in suspension. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large.

C. Host Cells

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organism that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny. As used herein, the terms "engineered" and "recombinant" cells or host cells are intended to refer to a cell into which an exogenous nucleic acid sequence, such as, for example, a vector, has been introduced. Therefore, recombinant cells are distinguishable from naturally occurring cells which do not contain a recombinantly introduced nucleic acid.

In certain embodiments, it is contemplated that RNAs or proteinaceous sequences may be co-expressed with other selected RNAs or proteinaceous sequences in the same host cell. Co-expression may be achieved by co-transfecting the host cell with two or more distinct recombinant vectors. Alternatively, a single recombinant vector may be constructed to include multiple distinct coding regions for RNAs, which could then be expressed in host cells transfected with the single vector.

A tissue may comprise a host cell or cells to be transformed with a polynucleotide encoding part or all of GLP-1. The tissue may be part or separated from an organism. In certain embodiments, a tissue may comprise, but is not limited to, myocytes, adipocytes, alveolar, ameloblasts, axon, basal cells, blood (e.g., lymphocytes), blood vessel, bone, bone marrow, brain, breast, cartilage, cervix, colon, cornea, embryonic, endometrium, endothelial, epithelial, esophagus, facia, fibroblast, follicular, ganglion cells, glial cells, goblet cells, kidney, liver, lung, lymph node, muscle, neuron, ovaries, pancreas, peripheral blood, prostate, skin, skin, small intestine, spleen, stem cells, stomach, testes, anthers, ascite tissue, cobs, ears, flowers, husks, kernels, leaves, meristematic cells, pollen, root tips, roots, silk, stalks, and all cancers thereof.

In certain embodiments, the host cell or tissue may be comprised in at least one organism. In certain embodiments, the organism may be, but is not limited to, a prokayote (e.g., a eubacteria, an archaea) or an eukaryote, as would be understood by one of ordinary skill in the art (see, for example, webpage http://phylogeny.arizona.edu/tree/phylogeny.html).

Numerous cell lines and cultures are available for use as a host cell, and they can be obtained through the American Type Culture Collection (ATCC), which is an organization that serves as an archive for living cultures and genetic materials (www.atcc.org). An appropriate host can be determined by one of skill in the art based on the vector backbone and the desired result. A plasmid or cosmid, for example, can be introduced into a prokaryote host cell for replication of many vectors. Cell types available for vector replication and/or expression include, but are not limited to, bacteria, such as *E. coli* (e.g., *E. coli* strain RR1, *E. coli* LE392, *E. coli* B, *E. coli* X 1776 (ATCC No. 31537) as well as *E. coli* W3110 (F–, lambda–, prototrophic, ATCC No. 273325), DH5α, JM109, and KC8, bacilli such as *Bacillus subtilis*; and other enterobacteriaceae such as *Salmonella typhimurium, Serratia marcescens*, various *Pseudomonas* specie, as well as a number of commercially available bacterial hosts such as SURE® Competent Cells and SOLOPACK™ Gold Cells (STRATAGENE®, La Jolla). In certain embodiments, bacterial cells such as *E. coli* LE392 are particularly contemplated as host cells for phage viruses.

Examples of eukaryotic host cells for replication and/or expression of a vector include, but are not limited to, HeLa, NIH3T3, Jurkat, 293, Cos, CHO, Saos, and PC12. Many host cells from various cell types and organisms are available and would be known to one of skill in the art. Similarly, a viral vector may be used in conjunction with either a eukaryotic or prokaryotic host cell, particularly one that is permissive for replication or expression of the vector.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

D. Expression Systems

Numerous expression systems exist that comprise at least a part or all of the compositions discussed above. Prokaryote- and/or eukaryote-based systems can be employed for use with the present disclosure to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MAXBAC® 2.0 from INVITROGEN® and BACPACK™ BACULOVIRUS EXPRESSION SYSTEM FROM CLONTECH®.

Other examples of expression systems include STRATAGENE®, COMPLETE CONTROL™ Inducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

It is contemplated that the proteins, polypeptides or peptides produced by the methods of the disclosure may be "overexpressed", i.e., expressed in increased levels relative to its natural expression in cells. Such overexpression may be assessed by a variety of methods, including radio-labeling and/or protein purification. However, simple and direct methods are preferred, for example, those involving SDS/PAGE and protein staining or western blotting, followed by quantitative analyses, such as densitometric scanning of the resultant gel or blot. A specific increase in the level of the recombinant protein, polypeptide or peptide in comparison to the level in natural cells is indicative of overexpression, as is a relative abundance of the specific protein, polypeptides or peptides in relation to the other proteins produced by the host cell and, e.g., visible on a gel.

In some embodiments, the expressed proteinaceous sequence forms an inclusion body in the host cell, the host cells are lysed, for example, by disruption in a cell homogenizer, washed and/or centrifuged to separate the dense inclusion bodies and cell membranes from the soluble cell components. This centrifugation can be performed under conditions whereby the dense inclusion bodies are selectively enriched by incorporation of sugars, such as sucrose, into the buffer and centrifugation at a selective speed. Inclusion bodies may be solubilized in solutions containing high concentrations of urea (e.g. 8M) or chaotropic agents such as guanidine hydrochloride in the presence of reducing agents, such as β-mercaptoethanol or DTT (dithiothreitol), and refolded into a more desirable conformation, as would be known to one of ordinary skill in the art.

E. Proteins, Polypeptides, and Peptides

In some cases, embodiments may utilize purified GLP-1 proteins, polypeptides, or peptides. The term "purified proteins, polypeptides, or peptides" as used herein, is intended to refer to an proteinaceous composition, isolatable from mammalian cells or recombinant host cells, wherein the at least one protein, polypeptide, or peptide is purified to any degree relative to its naturally-obtainable state, i.e., relative to its purity within a cellular extract. A purified protein, polypeptide, or peptide therefore also refers to a wild-type or mutant protein, polypeptide, or peptide free from the environment in which it naturally occurs.

The nucleotide and protein, polypeptide and peptide sequences for various genes have been previously disclosed, and may be found at computerized databases known to those of ordinary skill in the art. One such database is the National Center for Biotechnology Information's GenBank® and GenPept® databases. The coding regions for these known genes may be amplified and/or expressed using the techniques disclosed herein or by any technique that would be known to those of ordinary skill in the art. Additionally, peptide sequences may be sythesized by methods known to those of ordinary skill in the art, such as peptide synthesis using automated peptide synthesis machines, such as those available from Applied Biosystems (Foster City, Calif.).

Generally, "purified" will refer to a specific protein, polypeptide, or peptide composition that has been subjected to fractionation to remove various other proteins, polypeptides, or peptides, and which composition substantially retains its activity, as may be assessed, for example, by the protein assays, as described herein below, or as would be known to one of ordinary skill in the art for the desired protein, polypeptide or peptide.

Where the term "substantially purified" is used, this will refer to a composition in which the specific protein, polypeptide, or peptide forms the major component of the composition, such as constituting about 50% of the proteins in the composition or more. In preferred embodiments, a substantially purified protein will constitute more than 60%, 70%, 80%, 90%, 95%, 99% or even more of the proteins in the composition.

A peptide, polypeptide or protein that is "purified to homogeneity," as applied to the present disclosure, means that the peptide, polypeptide or protein has a level of purity where the peptide, polypeptide or protein is substantially free from other proteins and biological components. For example, a purified peptide, polypeptide or protein will often be sufficiently free of other protein components so that degradative sequencing may be performed successfully.

Various methods for quantifying the degree of purification of proteins, polypeptides, or peptides will be known to those of skill in the art in light of the present disclosure. These include, for example, determining the specific protein activity of a fraction, or assessing the number of polypeptides within a fraction by gel electrophoresis.

To purify a desired protein, polypeptide, or peptide a natural or recombinant composition comprising at least some specific proteins, polypeptides, or peptides will be subjected to fractionation to remove various other components from the composition. In addition to those techniques described in detail herein below, various other techniques suitable for use in protein purification will be well known to those of skill in the art. These include, for example, precipitation with ammonium sulfate, PEG, antibodies and the like or by heat denaturation, followed by centrifugation; chromatography steps such as ion exchange, gel filtration, reverse phase, hydroxylapatite, lectin affinity and other affinity chromatography steps; isoelectric focusing; gel electrophoresis; and combinations of such and other techniques.

Another example is the purification of a specific fusion protein using a specific binding partner. Such purification methods are routine in the art. As the present disclosure provides DNA sequences for the specific proteins, any fusion protein purification method can now be practiced. This is exemplified by the generation of an specific protein-glutathione S-transferase fusion protein, expression in *E.*

*coli*, and isolation to homogeneity using affinity chromatography on glutathione-agarose or the generation of a polyhistidine tag on the N- or C-terminus of the protein, and subsequent purification using Ni-affinity chromatography. However, given many DNA and proteins are known, or may be identified and amplified using the methods described herein, any purification method can now be employed.

Although preferred for use in certain embodiments, there is no general requirement that the protein, polypeptide, or peptide always be provided in their most purified state. Indeed, it is contemplated that less substantially purified protein, polypeptide or peptide, which are nonetheless enriched in the desired protein compositions, relative to the natural state, will have utility in certain embodiments.

Methods exhibiting a lower degree of relative purification may have advantages in total recovery of protein product, or in maintaining the activity of an expressed protein. Inactive products also have utility in certain embodiments, such as, e.g., in determining antigenicity via antibody generation.

VII. Combination Therapy

In certain cases, the GLP-1/UTMD therapy of the present disclosure (which may also include TB4) is utilized in conjunction with one or more other therapies for a cardiac-related medical condition. GLP-1/UTMD may also be used in combination with other genes or gene products, including TB4 (in peptide, protein, or nucleic acid form). The one or more other therapies may be directly or indirectly related to the cardiac-related medical condition (examples of indirectly related therapies include those for pain or infection).

The GLP-1/UTMD therapy may precede or follow the other agent treatment by intervals ranging from minutes to hours to days to weeks or months. In embodiments where the other agent and the GLP-1/UTMD therapy are applied separately to the individual, one would generally ensure that a significant period of time did not expire between the time of each delivery, such that the agent and GLP-1/UTMD therapy would still be able to exert an advantageously combined effect on the cell. In such instances, it is contemplated that one may contact the individual with both modalities simultaneously or within minutes of each other or within about 1-12, 6-12, or 12-24 h of each other. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

Yet further, GLP-1/UTMD may also include other nucleic acids or peptides, for example, but not limited to TB4. In such instances, GLP-1/TB4 UTMD therapy may also be used in combination may precede or follow the other agent treatment by intervals ranging from minutes to weeks or months. In embodiments where the other agent and the GLP-1/TB4/UTMD therapy are applied separately to the individual, one would generally ensure that a significant period of time did not expire between the time of each delivery, such that the agent and GLP-1/TB4/UTMD therapy would still be able to exert an advantageously combined effect on the cell. In such instances, it is contemplated that one may contact the individual with both modalities simultaneously or within minutes of each other or within about 1-12, 6-12, or 12-24 h of each other. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

In specific embodiments, GLP-1/UTMD therapy and TB4/UTMD therapy are provided at the same time or at different times. The GLP-1 and TB4 entities may be within the same plurality of microbubbles or they may be comprised in separate pluralities of microbubbles. In cases wherein the GLP-1/UTMD therapy and TB4/UTMD therapy are provided at different times, they may be separated by any suitable range in times, such as minutes, hours, days, or weeks. In embodiments wherein they are provided separately, the order of delivery of GLP-1/UTMD therapy and TB4/UTMD therapy may be of any suitable order, including delivery of GLP-1/UTMD prior to or subsequent to TB4/UTMD therapy. In cases wherein GLP-1/UTMD therapy and TB4/UTMD therapy are provided to an individual in need thereof, they may be provided with yet another therapy for a cardiac-related medical condition.

Examples of other treatments to be employed with the GLP-1/UTMD and/or GLP-1/TB4/UTMD therapy of the disclosure includes one or more of the following: ACE Inhibitors, Aldosterone Inhibitor, Angiotensin II Receptor Blocker (ARBs); Beta-Blockers, Calcium Channel Blockers, Cholesterol-Lowering Drugs, Digoxin, Diuretics, Inotropic Therapy, Potassium or Magnesium, Vasodilators, anti-coagulant medication, aspirin, or a combination thereof.

VIII. Kits of the Disclosure

Any of the compositions described herein may be comprised in a kit. In a non-limiting example, a GLP-1 and/or TB4 polynucleotide or primers for amplification of it may be comprised in a kit. In specific embodiments, the kit comprises GLP-1 and/or TB4 peptides. The kit may alternatively or additionally comprise reagents for generating liposomes and/or microbubbles and optionally may have additional agents for therapy of a cardiac-related medical condition.

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present disclosure also will typically include a means for containing the one or more compositions in close confinement for commercial sale. Such containers may include injection or blow-molded plastic containers into which the desired vials are retained.

The composition may be formulated into a syringeable composition. In which case, the container means may itself be a syringe, pipette, and/or other such like apparatus, from which the formulation may be applied to an infected area of the body, injected into an animal, and/or even applied to and/or mixed with the other components of the kit. However, the components of the kit may be provided as dried powder(s). When reagents and/or components are provided as a dry powder, the powder can be reconstituted by the addition of a suitable solvent. It is envisioned that the solvent may also be provided in another container means.

The kits of the present disclosure will also typically include a means for containing the vials in close confinement for commercial sale, such as, e.g., injection and/or blow-molded plastic containers into which the desired vials are retained.

In particular embodiments, the kit comprises reagents and/or tools for determining that an individual has a cardiac-related medical condition. In some embodiments, the kit comprises one or more additional therapies for a cardiac-related medical condition, such as one or more of ACE Inhibitor, aldosterone inhibitor, angiotensin II receptor blocker (ARBs); beta-blocker, calcium channel blocker, cholesterol-lowering drug, digoxin, diuretics, inotropic therapy, potassium, magnesium, vasodilator, anticoagulant medication, aspirin, and a combination thereof.

EXAMPLES

The following examples are included to demonstrate preferred embodiments of the disclosure. It should be appreciated by those of skill in the art that the techniques disclosed in the examples which follow present techniques discovered by the inventors to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1

Exemplary Materials and Methods

Animal Protocols and UTMD

All animal studies were performed in accordance with National Institute of Health (NIH) recommendations and the approval of our institutional animal research committee. Male Sprague-Dawley rats (230-270 g) were anesthetized with intraperitoneal ketamine (60 mg/kg) and xylazine (5 mg/kg), and a polyethylene tube (PE 50, Becton Dickinson, Franklin Lakes, Tenn., USA) was inserted into the right internal jugular vein by cut-down.

Animal protocol-1: A total of 18 normal rats received one of 3 treatments: (1) no treatment (normal control rats, n=6); (2) UTMD with pXL-BASII-CI-DsRed/pCI-hyPB (n=6); (3) UTMD with pXL-BASII-CI-GLP-1/pCI-hyPB (n=6), all were killed at 4 weeks after UTMD. The thymidine analog, 5-bromo-2-deoxyuridine (BrdU) (100 mg/kg, Sigma, St Louis, Mo.) intraperitoneal injected 6 hours prior to killing.

Animal protocol-2: A total of 60 rats were divided into: (1) no treatment (normal control rats, n=12); (2) adriamycin (ADM)[38] injection only, at total dose of 15 mg/kg/ip, 2.5 mg/kg/ip 6 times over 2 weeks, n=12. (3) ADM plus GLP-1 peptide injection, at GLP-1 peptide fragment 7-37 human (dose of 50 nmol/kg/ip/time×6, N=12, from Sigma, St Louis, Mo.), (4) ADM injection plus UTMD-GLP1 peptide delivery (same dose of GLP-1 peptide fragment 7-37 human mixed with microbubble for UTMD), n=12; (5) ADM injection plus UTMD with pXL-BASII-CI-GLP-1/pCI-hyPB, n=12. Half rats were killed at 16 hours after last ADM injection; other half rats were killed at 4 weeks after UTMD. The thymidine analog, 5-bromo-2-deoxyuridine (BrdU) (100 mg/kg) was injected intraperitoneally 6 hours prior to euthanasia.

Animal protocol-3: UTMD was performed after established adriamycin cardiomyopathy defined as a fractional shortening <30% by echocardiography. There were 3 groups of rats as follows: (1) normal control rats, n=6; (2) UTMD with pXL-BASII-CI-DsRed/pCI-hyPB (n=6); (3) UTMD with pXL-BASII-CI-GLP-1/pCI-hyPB (n=12). All were killed 4 weeks after UTMD. The thymidine analog, 5-bromo-2-deoxyuridine (BrdU) (100 mg/kg) was injected intraperitoneally 6 hours prior to euthanasia.

Animal protocol-4: Specific FOXO1 inhibitor (AS1842856, a small molecular compound from Millipore) was injected into rats with ADM cardiomyopathy to investigate if FOXO1 mediates ADM cardiomyopathy. There were 3 groups of rats as follows: (1) normal control rats, n=6; (2) ADM injection only group at total dose of 15 mg/kg/ip, 2.5 mg/kg/ip 6 times over 2 weeks, (n=6); (3) ADM at total dose of 15 mg/kg/ip, 2.5 mg/kg/ip 6 times over 2 weeks plus FOXO1 inhibitor injection (at total dose of 24 mg/kg/ip, 4 mg/kg/ip 6 times over 2 weeks (n=6). All rats were killed 4 weeks after ADM injection.

Piggybac transposon donor plasmids and helper plasmids ratio (pXL-BASII-CI-GLP-1/pCI-hyPB) was 5:1. Microbubble or control solutions (0.5 ml diluted with 0.5 ml phosphate-buffered solution (PBS)) were infused over 5 min via pump (Genie, Kent Scientific, Torrington, Conn.). During the infusion, ultrasound was directed to the heart using a commercially available ultrasound transducer (S3, Sonos 5500, Philips Ultrasound, Bothell, Wash.). A 2D echocardiographic view of the left ventricle was obtained in a short-axis view and the probe was clamped in placed. Ultrasound was then applied in ultraharmonic mode (transmit 1.3 MHz/receive 3.6 MHz) at a mechanical index of 1.4. Four bursts of ultrasound were triggered to every fourth end-systole by electrocardiogram using a delay of 45-70 ms after the peak of the R wave. These settings have shown to be optimal for plasmid delivery by UTMD using this instrument. Bubble destruction was visually apparent in all rats. After UTMD, the jugular vein was tied off, the skin closed, and the animals allowed to recover. All of rats were euthanized using an overdose of sodium pentobarbital (120 mg/kg). Hearts were harvested for histology, western blots and qRT-PCR assay.

RNA Isolation and qRT-PCR Analysis

Total RNA was isolated from 100 mg of harvested heart using the Trizol reagent (Invitrogen), according to the manufacturer's instructions and reverse-transcribed using Superscript III RT (Invitrogen). Real-time RT-qPCR analysis was performed on an ABI 7700 Sequence Detector (Applied Biosystems) using SYBR Green (RT2 SYBR Green qPCR Kit, Qiagen). Data were normalized to HKG expression (endogenous control). Changes in gene expression were normalized to control rat heart tissue. Complementary DNA PCR primer sequences information should be requested to the correspondence author.

Immunohistochemistry

Tissue samples were fixed in 10% formalin for 24 hours and transferred into 70% alcohol for paraffin embedding and 4% paraformaldehyde and 20% sucrose overnight at 4° C. for frozen sections. Cryostat sections 5-8 μm in thickness were further fixed with acetone (−20° C.) for 5 min and quenched for 5-20 min with 10 mM glycine in PBS. Sections were then rinsed in PBS 3 times, and permeabilized with 0.5% Triton X-100 in PBS for 15 min. The slides that needed further nuclear protein retrieval were subjected to boiling citrate buffer solution with tween 20 at pH 6.0 for 5 minutes. Sections were blocked with 20% Aquablock solution (EastCoast Bio, North Berwick, Me.) at room temperature for 1 hr and washed with PBS 1 time. The primary antibodies rabbit anti-NKX2.5, 1:500 dilution, and rabbit anti-ISL-1, 1:500 dilution, and mouse anti-cardiac troponin T, 1:250 dilution, rabbit anti-phosopho-histone H3, 1:500 dilution, rabbit anti Ki-67, 1:500 dilution, rabbit anti-BrDu, 1:200 dilution, rabbit anti-Aurora B, 1:200 dilution, mouse anti-GLP-1, 1:250 dilution, rabbit anti-GLP-1, 1:250 dilution, rabbit anti-topoisomerase IIα, 1:50 dilution, rabbit anti-topoisomerase IIβ, 1:200 dilution, rabbit anti-FOXO1, 1:300 dilution, rabbit anti-cyclin D, 1:300 dilution, rabbit anti-c-kit, 1:300 dilution, rabbit anti-OCT4, 1:250 dilution, rabbit anti-Nanog, 1:250 dilution, rabbit anti-SOX2, 1:500 dilution, (Abeam Inc, Cambridge, Mass.), anti-rabbit Smooth muscle actin-alpha, 1:500 dilution (Sigma, St. Louis, Mo.), anti-rabbit von Willebrand Factor, 1:200 dilution (Dako, Carpinteria, Calif.) (Abeam Inc, Cambridge, Mass.), were added and incubated for 2 hrs at RT. After washing with PBS three times for 5 min, the secondary antibody (Sigma, St. Louis, Mo.) anti-mouse lgG conjugated with FITC; anti-rabbit IgG-conjugated with Texas Red, or anti-donkey lgG conjugated with Cy5) (1:250 dilution in block solution) were added and incubated for 1 hr at RT. Sections were rinsed with PBS for 10 min, 3 times, and incubated with Dapi (Invitrogen, Carlsbad, Calif.), 1:5000 dilution for 5 min and washed 3 times with PBST, then mounted. A confocal microscope was used to take pictures. BrdU staining included with incubating in HCl (1N) for 10 minutes on ice to break open the DNA structure of the labeled cells and then followed by HCl (2N) for 10 minutes at room temperature before moving them to an incubator for 20 minutes at 37° C., Immediately after the acid washes, Borate buffer (0.1 M) is added to buffer the cells for 12 minutes.

Culture of HL-1 Cardiac Muscle Cells Line.

The HL-1 cell line was a generous gift from Dr. William C. Claycomb[40] in Louisiana State University Medical Center, New Orleans, La. The cells were maintained in Claycomb basal medium (Sigma) supplemented with 10% fetal bovine serum, 0.1 mM norepinephrine and 2 mM L-glutamine. HL-1 cells were treated with adriamycin at 0 µM, 0.25 µM, 0.50 µM, or 1.00 µM for 48 hrs in complete growth medium, and were subjected to immunofluorescent staining.

Western Blotting

Nuclear proteins extracts from cardiac tissue with a NE-PER Nuclear and Cytoplasmic Extraction Kit (Thermo Scientific, Rockford, Ill. 61105, USA). Protein concentrations were determined using the BCA-200 Protein Assay kit (Pierce); equal amounts of protein were separated by SDS-PAGE. After separation and transfer to nitrocellulose membranes, the membranes were incubated with primary antibodies (Abeam) to GLP-1 (1:1,000 dilution), anti-topoisomerase IIα(1:1,000 dilution), anti-topoisomerase IIβ (1:2,000 dilution), anti-cyclin D1(1:5000 dilution), anti-FoxO1(1:5000 dilution), anti-lamin (1:5,000 dilution; Sigma-Aldrich). Horseradish peroxidase secondary antibodies were used, and chemiluminescence was determined using the Super Signal West Dura detection system (Pierce); nuclear marker (lamin) was used to confirm equal loading. All Western blots were performed in duplicate.

Plasmid Construction

The piggybac transposon plasmids (pXL-BSII donor plasmid) was provided by Dr. Fraser at University of Notre Dame (Notre Dame, Ind.) and mouse piggybac transposase helper plasmid was provided by Dr. Bradley at Wellcome Trust Sanger Institute (Cambridge, England). Human GLP-1 cDNA with a furin cutting site after first ATG were constructed. DsRed cDNA vector was purchased from Clontech (Mountain view, CA), GLP-1 cDNAs were cloned to pCI vector (Promega, Madison, Wis.), hyperative piggybac transposase cDNA with EcoR1/NOT1 cutting was also subcloned into pCI vector and then GLP-1 or DsRed cDNA with CMV promoter and polyA fragment with BgL II/BamH1 cutting was subcloned to pXL-BSII vector. The plasmids digestion, ligation, subcloning, isolation and purification were performed by standard procedures, and once again sequenced to confirm that no artifactual mutations were present. GLP-1 constructs: GLP-1 cDNA(7-37) with a furin cutting site after first ATG were constructed. A nuclear localization signal (NLS) fragment was fused to GLP-1 cDNA (7-37). GLP-1NLS forward primers: 5-AAA-CTC-GAG-ATG-CGT-CAA-CGT-CGT-CAT-GCT-GAA-GGG-ACC-TTT-A-3 (SEQ ID NO. 7); GLP-1NLS reverse primers: 5-AAA-AGC-CGC-TCA-GAC-CTT-CCG-CTT-TTT-TTT-AGG-TCC-TCG-GCC-TTT-CAC-CAG-CCA-3 (SEQ ID NO. 8); This GLP-1NLS is composed of a start codon, furin cut codon, GLP-1 cDNA (7-37) and a stop codon (FIG. 10). DsRed cDNA vector was purchased from Clontech (Mountain View, Calif.), GLP-1NLS cDNAs were cloned to pCI vector (Promega, Madison, Wis.), hyperative piggybac transposase cDNA with EcoR1/NOT1 cutting also subcloned into pCI vector and then GLP-1NLS or DsRed cDNA with CMV promoter and polyA fragment with BgL II/BamH1 cutting subcloned to pXL-BSII vector. The plasmids digestion, ligation, subcloning, isolation and purification were performed by standard procedures, and once again sequenced to confirm that no artifactual mutations were introduced.

Manufacture of Plasmid-Containing Lipid-Stabilized Microbubble

Lipid-stabilized microbubbles were prepared using a solution of DPPC (1,2-dipalmitoyl-sn-glycero-3-phosphatidylcholine, Sigma, St. Louis, Mo.) 2.5 mg/ml; DPPE (1,2-dipalmitoyl-sn-glycero-3-phosphatidylethanolamine, Sigma, St. Louis, Mo.) 0.5 mg/ml; and 10% glycerol was mixed with 2 mg of plasmids (pXL-BSII-CI-TB4 plasmid and pCI-mPB ratio is 5:1) dissolved in 50 ul of lipefectamine 2000 (Invitrogen, Carlsbad, Calif.). Aliquots of 0.5 ml of this phospholipid-plasmid solution were placed in 1.5 ml clear vials; the remaining headspace was filled with the perfluoropropane gas (Air Products, Inc, Allentown, Pa.). Each vial was incubated at 4° C. for 30 min and then mechanically shaken for 30 seconds by a dental amalgamator (Vialmix™, Bristol-Myers Squibb Medical Imaging, N. Billerica, Mass.). The lipid-stabilized microbubbles appear as a milky white suspension floating on the top of a layer of liquid containing unattached plasmid DNA. The mean diameter and concentration of the microbubbles in the upper layer were measured by a particle counter (Beckman Coulter Multisizer III, Miami, Fla.).

Echocardiography

Echocardiographic measurements of LV fractional shortening and LV posterior wall thickness were made from digital images acquired with a 12 MHz broadband transducer (S12 probe, Philips Ultrasound, Bothell, Wash.). Fractional shortening was evaluated from the following formula: FS=(LVIDd−LVIDs)/LVIDd×100.

Data Analysis

Data was analyzed with Statview software (SAS, Cary, N.C., USA). The results are expressed as mean±one standard deviation. Differences were analyzed by repeated measures ANOVA with Fisher's post hoc test and considered significant at $P<0.05$.

Example 2

Myocardial Regeneration in Adriamycin Cardiomyopathy by Nuclear Expression of GLP1 Using Ultrasound Targeted Microbubble Destruction There are nearly 5.7 million Americans with heart failure (HF) and approximately 670,000 new cases are diagnosed in the U.S. each year. HF affects people of all ages, from children and young adults to the middle-aged and the elderly (Roger, et al., 2012). Traditional medical therapy for HF is targeted toward relief of symptoms and blockade of neurohormonal activation that propagates HF. When medical therapy fails, heart transplant or left ventricular assist devices may be appropriate, but are limited by donor supply, immunosuppression, expense and complications. The ideal goal for HF therapy is myocardial regeneration, which has become a major goal of HF therapy since the discovery that cardiomyocytes are not terminally differentiated. There are various theories about the origin of regenerating cardiomyocytes, including self-replication of pre-existing adult cardiac muscle cells (Senyo, et al. 2013; Eulalio, et al. 2012), differentiation of adult resident cardiac progenitor cells (Smart, et al., 2011; Bolli, et al., 2011), dedifferentiation and proliferation of adult cardiac muscle cells (Beltrami, et al. 2003; Jopling, et al. 2010; Porrello, et al., 2011) and transdifferentiation of fibroblast cells into cardiac muscle cells (Song, et al., 2012; Qian, et al., 2012). These findings have led to numerous clinical trials of stem cell therapy. However, a recent meta-analysis of 49 stem cell trials for HF identified several flaws and internal discrepancies and no detectable benefit in left ventricular ejection fraction (Nowbar, et al., 2014). It remains unclear whether myocardial regeneration in heart failure is able to reverse established cardiomyopathy.

This disclosure evaluates the effect of gene therapy with glucagon-like peptide-1 (GLP-1) on adriamycin-induced cardiomyopathy in a rodent model. The adriamycin model was chosen to avoid the potential problems of decreased myocardial blood flow and necrosis/fibrosis associated with ischemic cardiomyopathy. GLP-1 was selected because it has been found to have cardioprotective effects independent of those attributable to tight glycemic control (Ussher, et al., 2012). Intravenous infusions of GLP-1 peptide to patients with myocardial infarction or chronic HF improved global LV function and the function of ischemic LV segments (Timmers, et al., 2009; Halbirk, et al., 2010). However, GLP-1 acts indirectly via GLP-1 receptors distributed on the membrane of cardiomyocytes. GLP-1R acts via cAMP generation to produce distinct downstream signaling events via intracellular calcium or ERK1/2 activation (Ussher, et al., 2012). However, no data have been published regarding the effects of GLP-1 gene delivery to heart. It was considered to deliver GLP-1 gene directly to the hearts of normal rats or rats with HF induced by adriamycin. Ultrasound targeted microbubble destruction (UTMD) (Bekeredjian, et al., 2003; Korpanty, et al., 2005; Chen, et al., 2012; Chen, et al., 2013) was utilized, which has been used to direct gene or protein therapy to specific organs in vivo. Data showed that UTMD directed GLP-1 to both cytoplasm and nuclei of cardiomyocytes in vivo. Because nuclear expression of GLP-1 gene had not been previously reported, a nuclear localizing signal was selected to investigate the effects of GLP-1 gene delivered specifically to the nucleus using a piggybac transposon plasmid system (Saridey, et al., 2009; Cary, et al., 1989; Cadinanos, et al., 2007) to rat hearts. After a single UTMD treatment, transgenic GLP-1 was overexpressed in nuclei of rat heart cells with evidence that transfected cardiac cells underwent dedifferentiation and proliferation. The results show that GLP-1 gene delivery to heart stimulates myocardial regeneration and reversal of adriamycin cardiomyopathy.

Successful Overexpression of GLP-1 in Nuclei of Heart Cells after UTMD-GLP-1 Gene Delivery to Heart of Normal Rats There is the absence of GLP-1 signal in the heart of normal control rats or UTMD-DsRed control rats. However, GLP-1 is seen in the hearts of rats treated with UTMD-GLP1NLS, notably in nuclei of heart cells. GLP-1 was not detected in the bloodstream using GLP-1 ELISA kit. Western blot was employed to detect GLP-1 from cardiac nuclear protein extracts and the results showed that GLP-1 signal existed in cardiac muscle nuclear protein extracts of UTMD-GLP1NLS group (FIG. 1, panel A). GLP1 mRNA level was further evaluated with quantitative RT-PCR. The result (FIG. 1, panel B) shows that the GLP-1 mRNA level in UTMD-GLP1NLS group was 84-fold greater than in normal control or UTMD-DsRed control groups ($P<0.001$). The percentage of GLP-1 positive cells was also counted in heart slides. GLP-1 was present in 50.7% of cardiomyocytes, 16.7% of vascular endothelial cells, 14.3% of vascular muscle cells and 18.3% of vimentin positive cells (FIG. 1, panel C).

Reversal of Adriamycin Cardiomyopathy after UTMD-GLP-1 Gene Therapy

Figure 2:
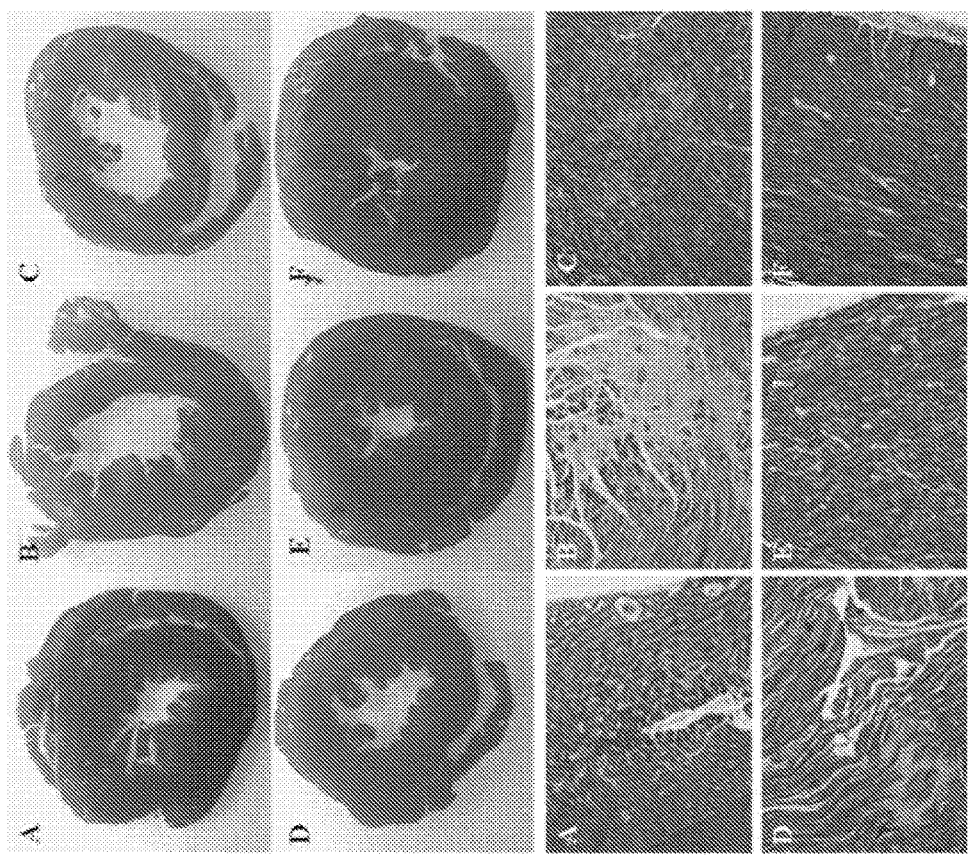
FIG. 2. Masson's trichrome staining and GLP-1 staining. Panel A is normal rat heart. Panel B is ADM only. Panel C is ADM plus GLP peptide treatment. Panel D is ADM plus UTMD-GLP1 peptide delivery. Panel E is ADM plus UTMD-GLP1 gene therapy. Panel F is ADM injection first and 14 day late UTMD-GLP1 gene therapy. The upper panel is Masson's trichrome staining for whole heart crossing section. Lower panel is lower power imaging, scale bar is 200 μm.
Figure 3:
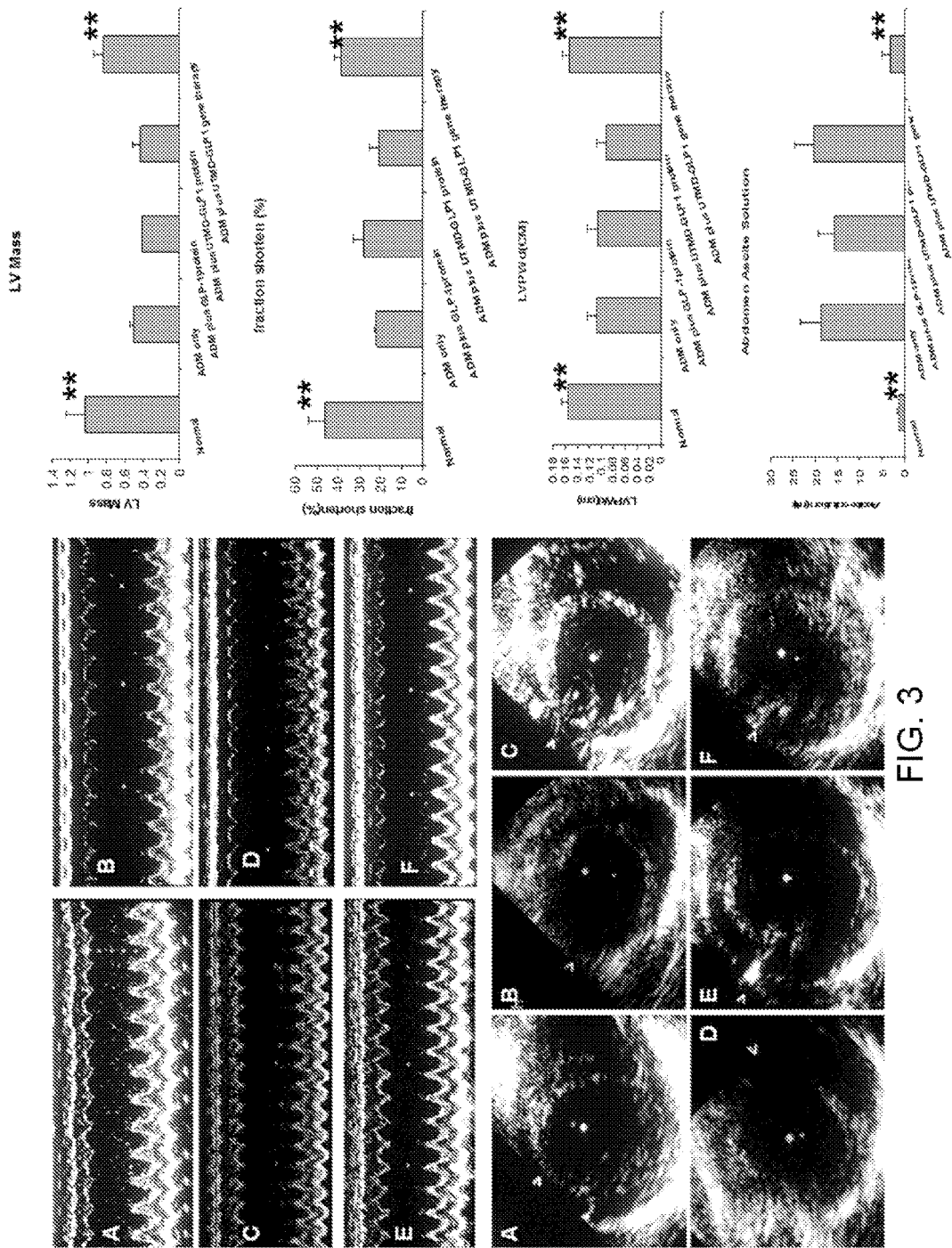
FIG. 3. Echocardiography evaluated heart structure and functioning. A: Normal Rat heart; B: ADM injection only; C: ADM injection plus GLP protein treatment; D: ADM injection plus UTMD-GLP1 protein delivery; E: ADM injection plus UTMD-GLP1 gene therapy; F: ADM injection first and 14 day late UTMD-GLP1 gene therapy the upper of left panel is M-model images; down of left panel is 2 dimensional left ventricle images at short axis view. Right panels are graphics for LV mass, fraction shorten index, LVPWd and abdomen ascite solution. Values are presented as mean±SEM; n=6 per group; **P<0.001 vs control groups.
Figure 4:
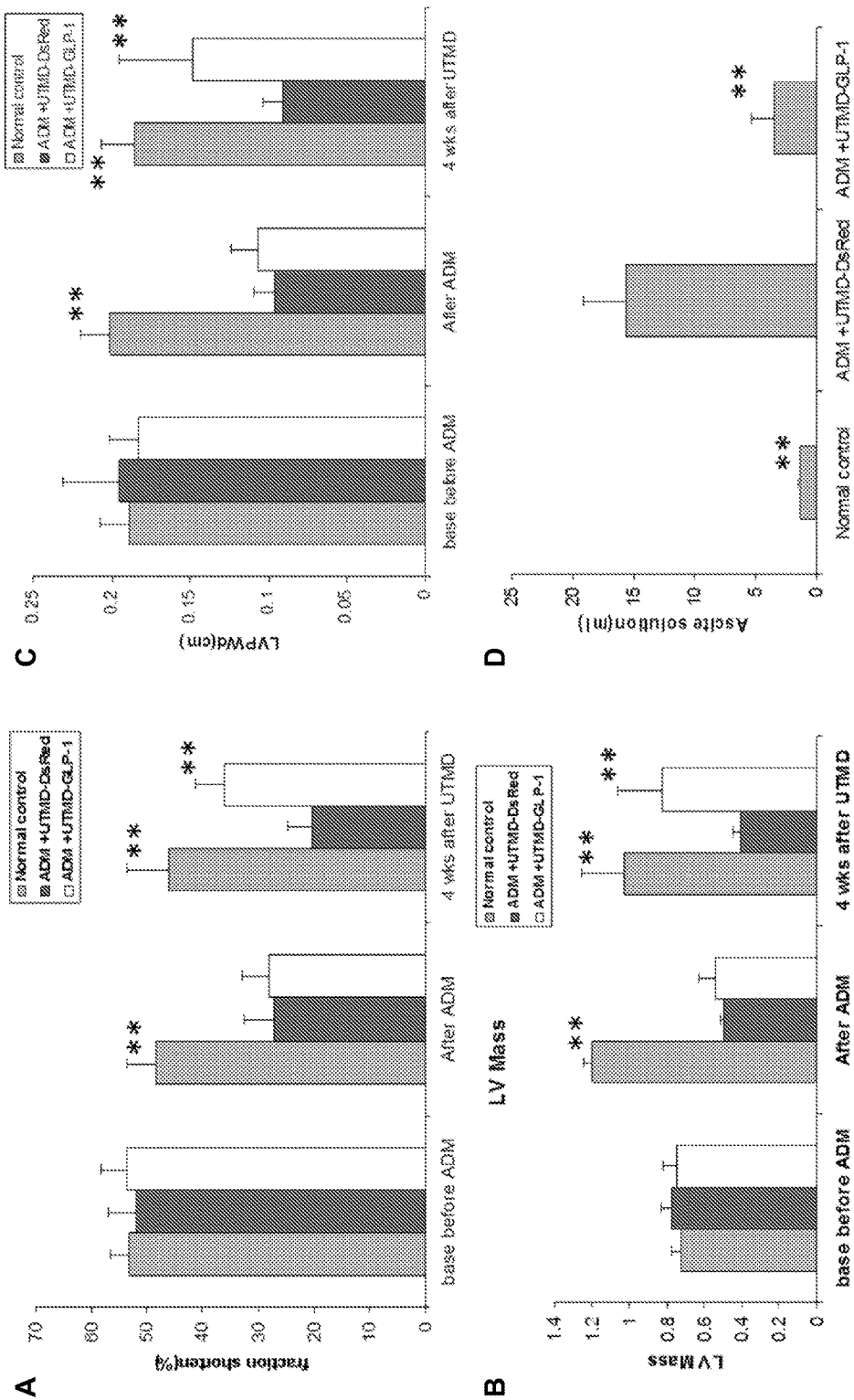
FIG. 4. Therapeutic effects of GLP1 gene heart delivery on established adriamycin cardiomyopathy. Panel A is a graphic for fractional shortening (%). Panel B is a graphics for left ventricular mass. Panel C is a graphics for left ventricular post wall depths (LVPWd). Panel D is a graphics for ascites volume. Values are presented as mean±SEM. n=6 per group; **P<0.001 vs control groups.
Figure 11:
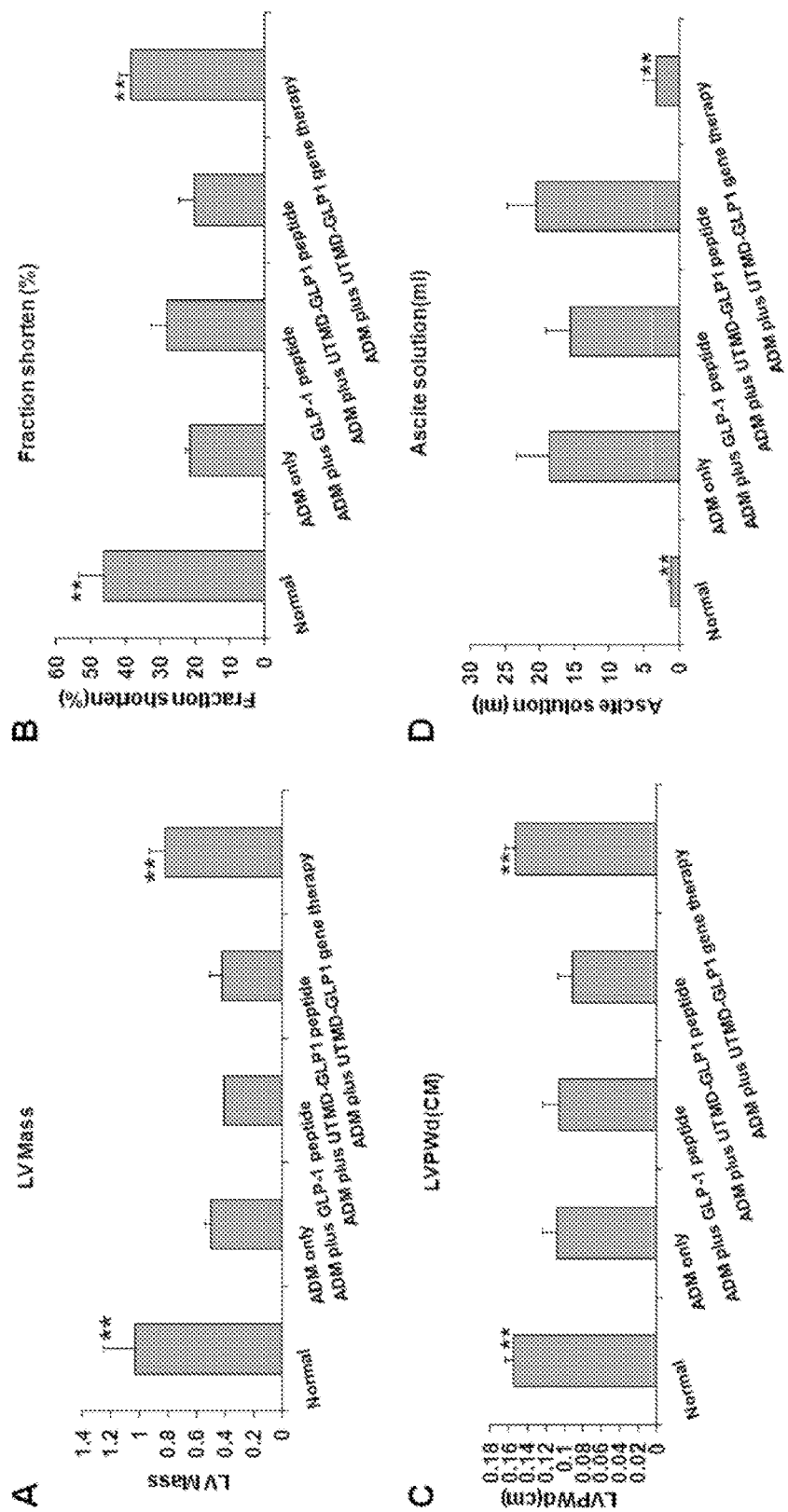
FIG. 11. Echocardiography evaluated heart structure and functioning (2D echo imaging at a short axis view of left ventricle and then measures with M-model). Panel A is graphic for LV mass. Panel B is graphic for fraction shorten index. Panel C is graphic for LVPWd. Panel D is graphic for abdomen ascite solution. Values are presented as mean±SEM. n=6 per group; **P<0.001 vs control groups.

It was considered if there is any possible pharmacological effects of GLP-1NLS gene on rat hearts with established adriamycin cardiomyopathy. FIG. 2 (upper panels) shows the gross pathology of LV walls in the groups of ADM injection only, ADM injection plus GLP1 peptide treatment, and ADM injection plus UTMD-GLP1 peptide delivery (B, C, and D). Rats with adriamycin cardiomyopathy (B, C) had thin LV walls and dilated LV cavities compared to normal controls (A). Adriamycin rats who were treated with UTMD-GLP-1NLS gene therapy early (E) or 14 days later (F) resembled normal controls. The lower panels show the results of Masson's trichrome staining for fibrosis, which was significantly decreased after UTMD-GLP1-NLS treatment (E and F). The nuclear location of GLP-1 in UTMD-GLP1-NLS gene therapy groups was determined. Echocardiography was utilized to evaluate heart structure and function in all groups. FIGS. 4 and 11 demonstrated decreased LV mass and wall thickness in adriamycin cardiomyopathy with restoration to normal values by GLP-1NLS gene therapy but not GLP-1 peptide therapy. Similar findings were seen for LV fractional shortening and volume of abdominal ascites (FIGS. 4 and 11). Of 12 rats with established adriamycin cardiomyopathy, 10 demonstrated complete normalization of LV size and function after UTMD-GLP-1 gene therapy, the other 2 were not improved significantly.

Nuclear GLP-1 Inhibits the Activation of Nuclear FoxO1

Figure 6:
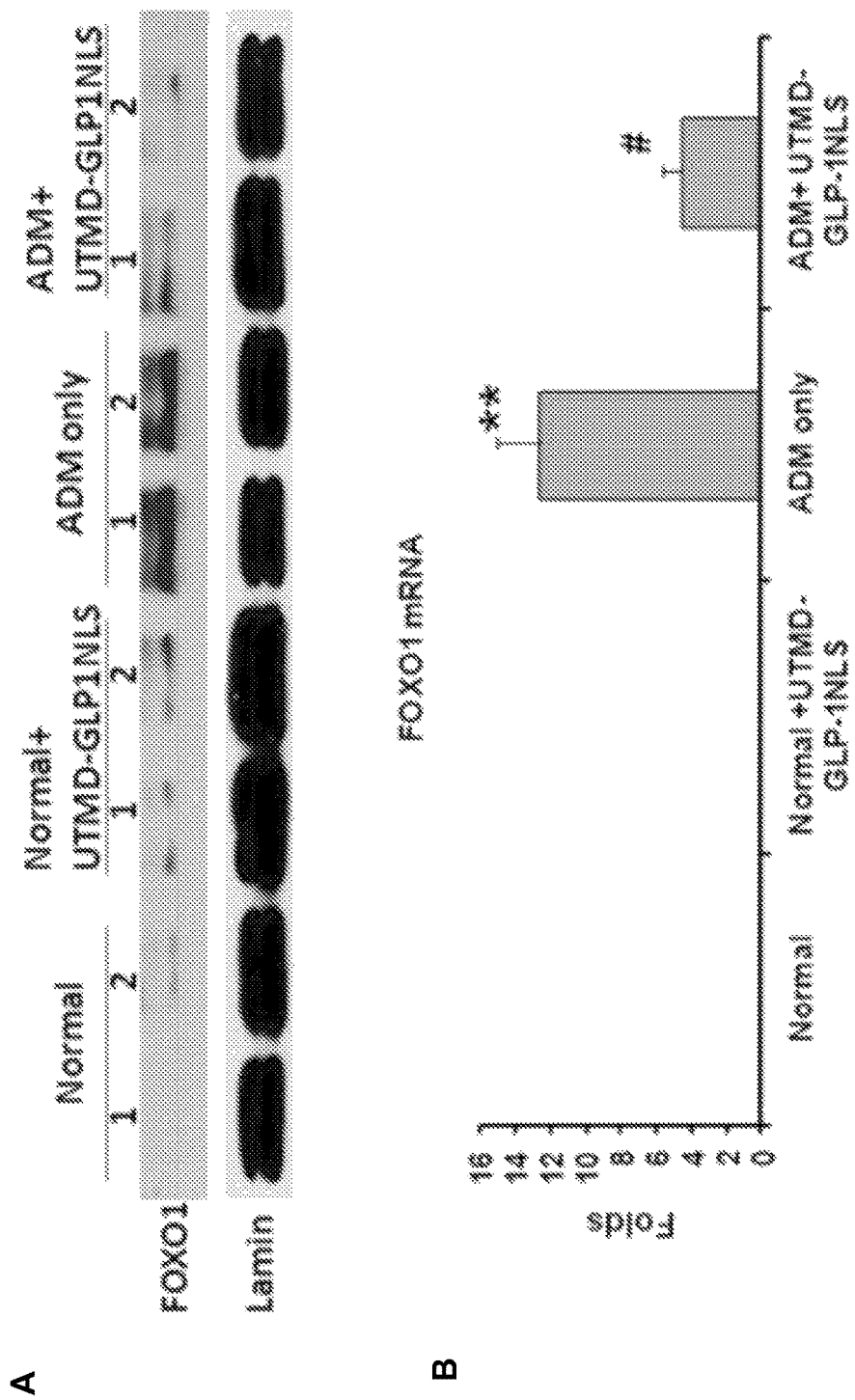
FIG. 6. Myocardial nuclear overexpression of FOXO1 induced by adriamycin. Panel A is western blot for detecting nuclear FOXO1 from nuclear protein extracts of heart tissue, lamin is a marker of nuclear proteins. Panel B is qRT-PCR for FOXO1 mRNA level. Values are presented as mean±SEM, n=6 per group; **P<0.001 vs normal group and normal plus UTMD-GLP-1NLS group, # P<0.001 vs ADM only.
Figure 12:
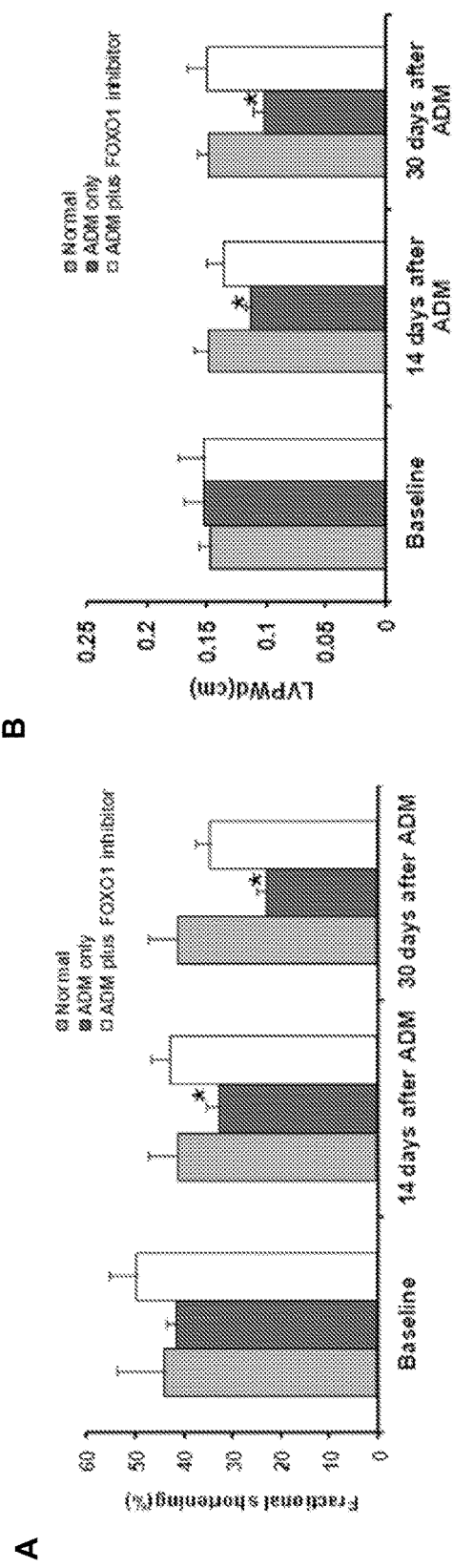
FIG. 12. FOXO1 inhibitor (AS1842856) inhibited the activation of myocardial nuclear FOXO1 in ADM cardiomyopathy are associated with reversal of heart function failure. Panel A is a graphic for fractional shortening (%). Panel B is a graphics for left ventricular post wall depths (LVPWd), Values are presented as mean±SEM. n=6 per group; *P<0.01 vs normal and ADM plus FOXO1 inhibitor groups.

Recently FoxO proteins (forkhead box proteins, O) were considered as key factors during the development of diabetic cardiomyopathy or ischemic cardiomyopathy. This is the first report showing that FoxO1 is involved in adriamycin-induced cardiomyopathy. FoxO1 signal is present in nuclei of cardiac muscle cells with established adriamycin cardiomyopathy. However, in normal rat heart slides FoxO1 signal was not seen in nuclei of cardiac muscle cells, although it was occasionally present in cytoplasm. After UTMD GLP-1-NLS gene delivery, transgenic nuclear overexpression of GLP-1 gene was associated with disappearance of nuclear FoxO1. The results (FIG. 6A) of FoxO1 western blots confirm a significant increase of FoxO1 in cardiac nuclear protein extracts of ADM only group, and FoxO1 decreased to a nearly normal level after UTMD GLP-1NLS gene delivery. The result (FIG. 6B) shows that the FoxO1 mRNA level in ADM only group was 12.6-fold greater than in normal control or normal plus UTMD-GLP-1NLS groups ($P<0.001$). However, FoxO1 mRNA level was decreased to 4.5-fold ($P<0.01$ vs ADM only) after UTMD GLP-1NLS gene delivery. It was considered to confirm this finding in an in vitro cell culture. Adriamycin under 0.25, 0.5, and 1.0 µM concentration significantly activates overexpression of nuclear FoxO1 in HL-1 cardiac muscle cell line. FIG. 12 showed that specific FoxO1 inhibitor (AS1842856, a small molecular compound) is able to block the activation of myocardial nuclear FoxO1 and reverse ADM cardiomyopathy (panel A-B). The data taken together demonstrates that activation of myocardial nuclear FoxO1 mediates ADM cardiomyopathy.

Nuclear GLP-1 Activates Myocardial Topoisomerase IIα to Initiate Overexpression of Cyclin D1 for G1/S Transition of Cell Cycle of Adult Cardiomyocytes.

Figure 7:
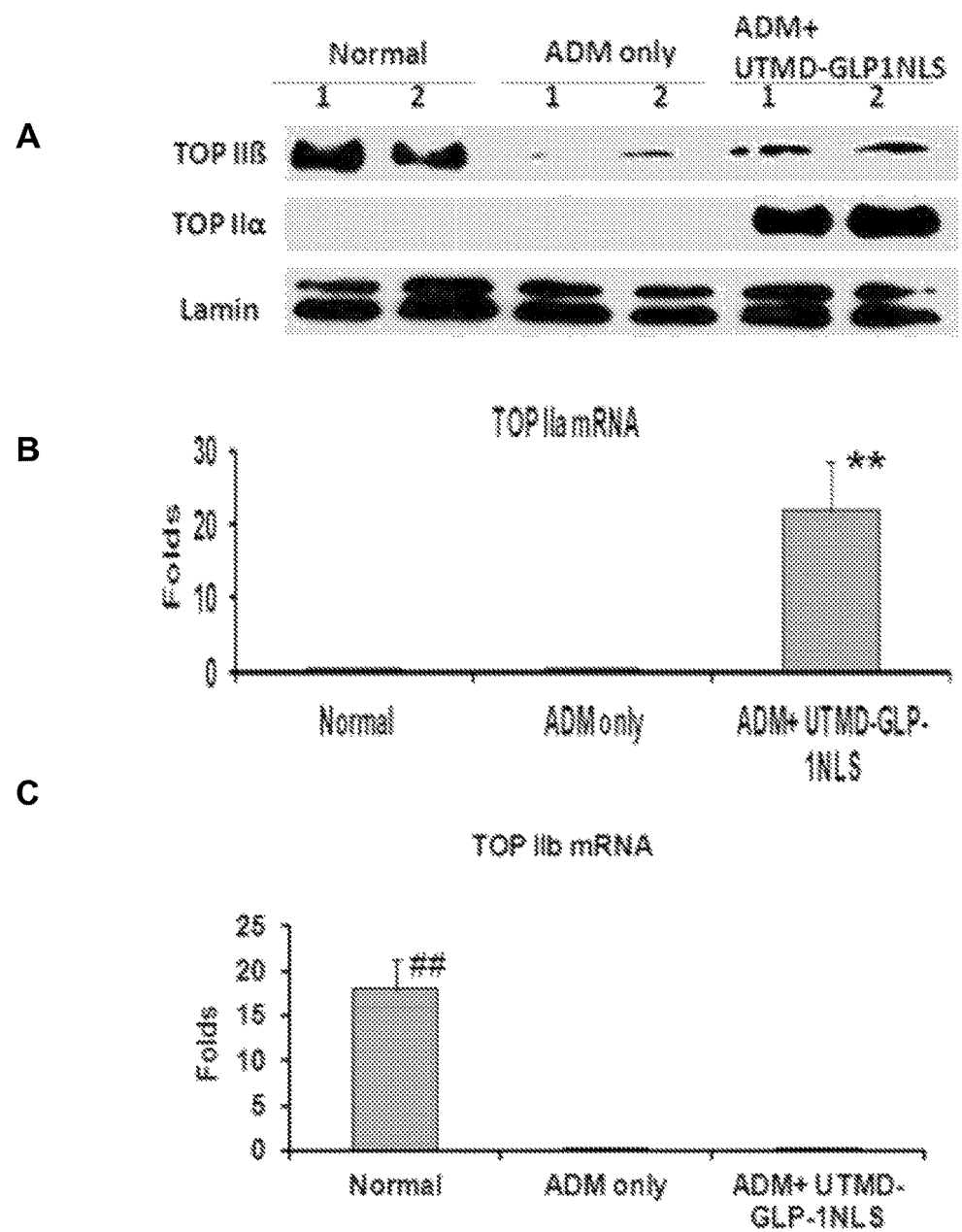
FIG. 7. Expression of myocardial nuclear enzyme Topoisomerase II α and β. Panel A is western blots for detecting nuclear TOP IIα and TOP IIβ from nuclear protein extracts of heart tissue, lamin is a marker of nuclear proteins. Panel B and C are qRT-PCR for TOP IIα and TOP IIβ mRNA level. Values are presented as mean±SEM, n=6 per group; **P<0.001 vs normal group and ADM injection only group; ##P<0.001 vs ADM injection only group and ADM injection plus UTMD-GLP-1NLS group.
Figure 8:
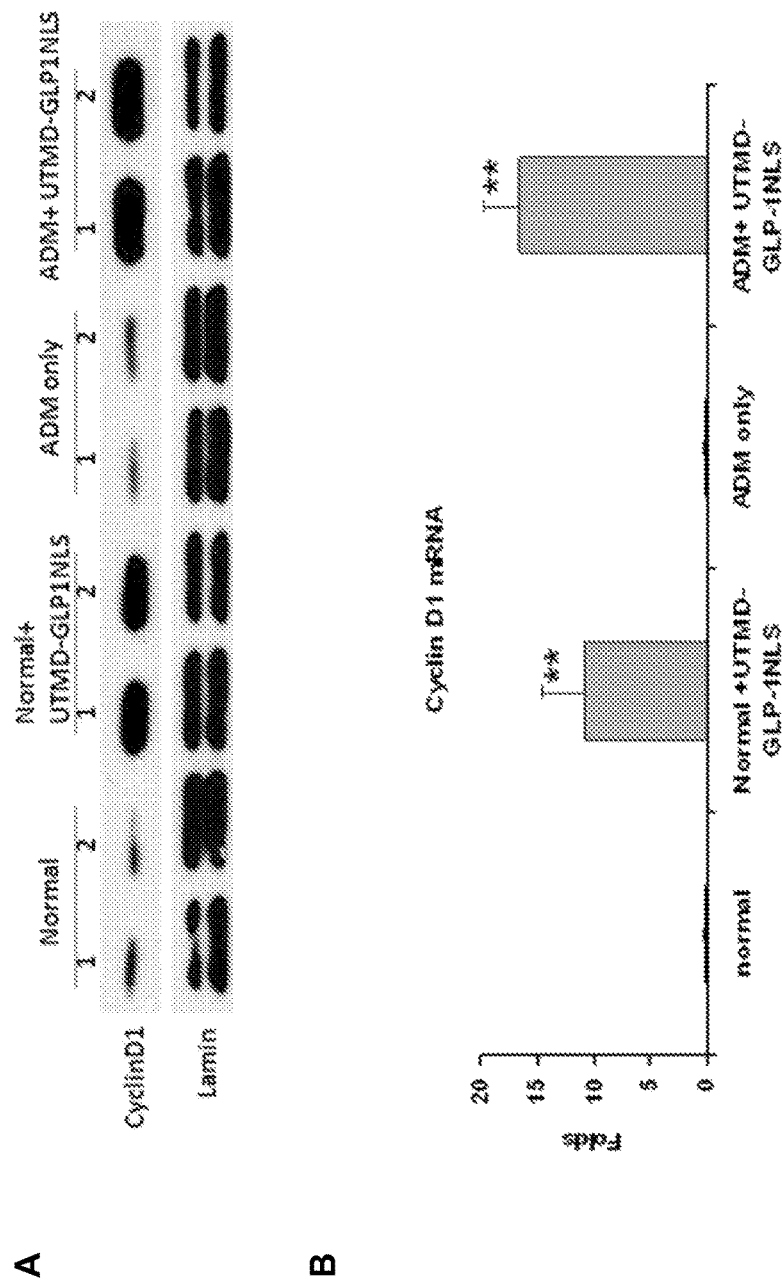
FIG. 8. Overexpression of myocardial nuclear cyclin D1. Panel A is western blots for detecting nuclear cyclin D1 from nuclear protein extracts of heart tissue, lamin is a marker of nuclear proteins. Panel B is qRT-PCR for cyclin D1 mRNA level. Values are presented as mean±SEM. n=6 per group; **P<0.001 vs normal group and ADM injection only group.

Topoisomerase II is a nuclear enzyme that has an important role in topological rearrangement of DNA during replication, transcription and resolution/separation of daughter chromosomes at mitosis. Topo IIα which is considered a specific marker for cell proliferation, does not exist in adult cardiomyocytes, however Topo IIβ is normally present in adult mammalian cardiomyocytes. Topo IIβ exists in nuclei of cardiomyocytes of normal controls, but after ADM injection, is no longer seen and could not be recovered by UTMD-GLP-1 gene delivery. However, Topo IIα was detected in the nuclei of some cardiomyocytes after UTMD-GLP-1 gene delivery, providing further evidence for cardiomyocyte proliferation after GLP-1 myocardial nuclear expression. The result (FIG. 7A) of TOP II western blots also shows TOP IIα expressed in cardiac nuclear protein extracts of ADM plus UTMD-GLP-1 group. Interestingly TOP IIβ bands significantly decreased after adriamycin treatment. The qRT-PCR (FIG. 7B-7C) shows that the TOP IIα mRNA level in ADM plus UTMD-GLP-1NLS group was 21.8-fold greater than in normal control or ADM only groups (P<0.001), however TOP IIβ mRNA level in normal group was 18-fold greater than in ADM only or ADM plus UTMD-GLP-1NLS groups (P<0.001). FIG. 8 addresses overexpression of cyclin D1 in the nucleus of cardiomyocytes after GLP-1NLS gene delivery. The results (FIG. 8A-8B) of western blots and qRT-PCR support the overexpression of cyclin D1 in nuclei of cardiac muscle cells after UTMD-GLP-1NLS.

Regenerating Adult Cardiomyocytes are in Dedifferentiation.

Dedifferentiation and proliferation of mature cardiomyocytes has only been observed in zebrafish, amphibians (Jopling, et al., 2010) or in neonatal mouse heart (Porrello, et al., 2011). Although adult mammalian cardiomyocytes generally lose the capability of dedifferentiation and proliferation they exhibited in the fetus stage, it was considered if this capability can be recovered by genetic manipulation in adriamycin cardiomyopathy. Dedifferentiation of adult pancreatic beta cell (Talchai, et al., 2012) was mediated by the activation of nuclear FoxO1 under diabetic condition. The data (FIG. 6) suggests that ADM induced overexpression of nuclear FoxO1. In addition, nuclear FoxO1-positive myocardium in adriamycin-induced cardiomyopathy does not undergo dedifferentiation but apoptosis. However, after UTMD-GLP-1NLS treatment, embryonic stem cell markers (OCT4, Nanog, and SOX2) were induced in nuclei of adult cardiac muscle cells. Further evidence to support dedifferentiation of adult rodent cardiomyocytes is co-expression of smooth muscle actin alpha (a marker of coronary artery muscle cells) with cardiac troponin T (a marker of mature cardiac muscle cell) in sarcomere disassembly area. von Willebrand factor (vWf), a marker of vascular endothelial cells was not seen to co-localize with cTNT. There are some c-kit positive adult cardiac muscle cells to support dedifferentiation of adult cardiac muscle cells into multipotent cardiac stem-like cells.

There is the presence of NKX2.5-positive adult cardiomyocytes in adriamycin cardiomyopathy rats treated with UTMD-GLP1 gene therapy early and 14 day later but not in the controls. NKX2.5 signal was clearly seen in the nucleus of a small number of cardiac troponin T positive cells. Similar findings were seen with ISL-1. The percentage of NKX2.5 or ISL-1 positive cardiomyocytes was counted in 1000 cTnT positive cardiomyocytes cells in anterior wall and posterior LV walls with serial sections through each rat heart (n=6 each group). The percentage of NKX2.5 positive cardiomyocytes in the gene therapy groups (FIG. 9A) was 8.73±0.83% and 8.5111.45% (p<0.001 vs controls). The percentage of ISL-1 positive cardiomyocytes (FIG. 9B) was 11.5712.31% and 11.97±3.24% in the gene therapy groups. There were GATA4 positive nuclei in these treated groups. NKX2.5, GATA4 and ISL-1 are considered markers of early cardiomyocyte differentiation (Smart, et al., 2011; Boni, et al., 2008). Sarcomere disassembly is considered specific for cardiomyocyte proliferation (Porrello, et al., 2011; Bersell, et al., 2009). There were NKX2.5 and ISL-1 positive nuclei located in sarcomere disassembly structure. Thus, in particular embodiments gene therapy with GLP-1NLS by UTMD leads to dedifferentiation and proliferation of nuclear FoxO1 positive cardiomyocytes in the rat adramycin-induced cardiomyopathy model.

Dedifferentiated Adult Cardiomyocytes are in Proliferation.

Figure 5:
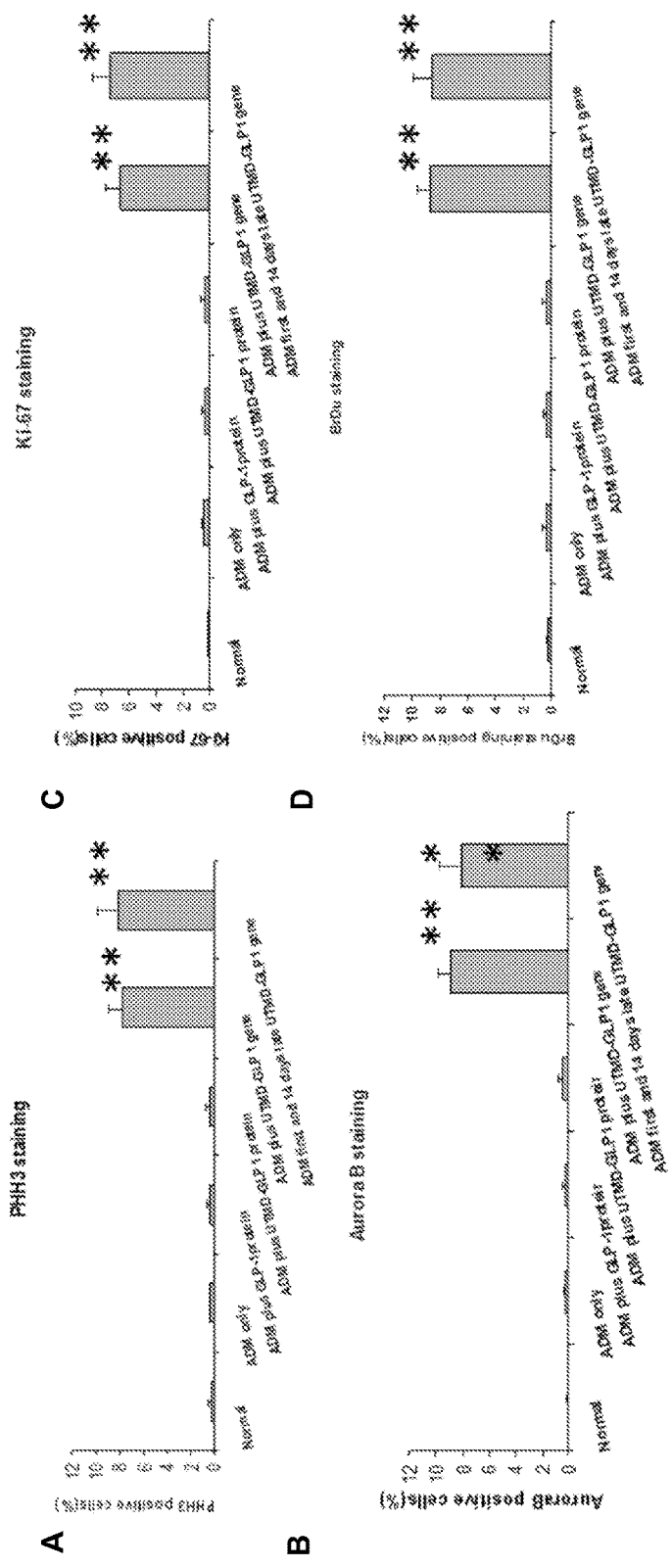
FIG. 5. Dedifferentiated adult cardiac muscle cells are in proliferation. Panels are the graphics for the percentage of anti-PHH3 (A), anti-Aurora B (B), anti-Ki-67 (C), and anti-BrDu (D) positive cardiac muscle cells. Values are presented as mean±SEM. n=6 per group; **P<0.001 vs control groups.

Two proliferation markers (anti-BrDu and anti-Ki-67) and two mitotic markers (anti-phospho-histone H3 (Ser10) (PHH3) and anti-aurora B) were used to demonstrate if dedifferentiated cardiac muscle cells were proliferating. The percentage of BrDu, PHH3 or Ki-67 or aurora B positive cardiomyocytes was calculated by counting stained nuclei from 1000 cTnT positive cardiomyocytes cells in the anterior and posterior LV walls using serial sections through each rat heart (n=6 each group). BrDu signal was observed within the nucleus of cTnT positive cardiomyocytes by confocal microscopy (FIG. 5). The percentage of BrDu positive cardiac muscle cells in the rats treated with UTMD-GLP1NLS gene therapy early and 14 days later was 8.73±0.83% and 8.51±1.45% (p<0.001 vs controls). Similarly, the percentage of Ki-67 positive cardiac muscle cells was 6.57±1.12% and 7.37±1.35% (p<0.001 vs controls) (FIG. 5). Aurora B staining was clearly seen in nuclei of cardiomyocytes treated with GLP-1 gene therapy by UTMD. The percentage of aurora B positive cardiac muscle cells in the two gene therapy groups was 8.93±0.90% and 8.11±1.62% (p<0.001 vs controls). PHH3 signal was observed within the nucleus of cTnT positive cardiomyocytes by confocal microscopy. The percentage of PHH3 positive cardiac muscle cells in the UTMD-GLP1NLS gene therapy groups was 7.73±1.20% and 8.10±1.70% (p<0.001 vs controls) (FIG. 5).

Significance of Certain Embodiments

After systemic administration of GLP-1 peptide, GLP-1 binds with its receptor on the cell membrane and activates adenylate cyclase, leading to increased intracellular cAMP levels. This triggers a wide range of cardioactive effects including increased heart rate and blood pressure, increased p38 MAPK activity, Akt/ERK1/2 phosphorylation, GLUT4, glucose intake, and decreased apoptosis in the heart (Ussher et al., 2012). However, it was recently reported (Kim et al., 2013) that GLP-1r exists only in atrial, but not in ventricular cardiomyocytes, and that excited GLP-1r signal activates atrial ANP and mediates "so called GLP-1 cardioprotection". The data indicate that GLP-1 targeted to the cell nucleus of ventricular cardiomyocytes triggers sufficient myocardial regeneration to reverse established adriamycin cardiomyopathy in rats. This is a novel finding that has important clinical implications for treatment of HF. Established adriamycin cardiomyopathy is a lethal disease. When HF develops, mortality is approximately 50% in a year. Moreover, treatment of established adriamycin cardiomyopathy is directly only to HF symptoms. There is no known therapy for reversing the underlying cardiomyopathy (Chatterjee et al., 2010). Heart transplant is often not an option in these patients for fear that the requisite immunosuppressive therapy could activate whatever malignancy necessitated adriamycin therapy. Zhang et al. (2012) reported that adriamycin-induced cardiomyopathy was mediated by topoisomerase-IIβ. Adriamycin binds with topoisomerase-IIβ and formed a complex, activated topoisomerase-IIβ to cut double strands of DNA and leaded to mitochondia biogenesis, and caused cardiac muscle cell death. Topoisomerase-IIα, which does not exist in adult cardiomyocytes, is a specific marker of cell proliferation. The data shows a novel molecular mechanism of GLP-1 that stimulates cardiomyocyte proliferation associated with activation of topoisomerase-IIα, when GLP-1 is targeted to the cell nucleus by UTMD and a nuclear localizing signal. This was not seen with systemic administration of GLP-1 peptide that is known to bind to the cell membrane. Further studies are needed to decipher how nuclear GLP-1 activates topoisomerase-IIα and cyclinD1 in adult mammalian cardiomyocytes.

Battiprolu et al. (2012) reported that metabolic stress-induced activation of FoxO1 in nuclei of cardiac muscle cells is central to the development of diabetic cardiomyopathy in diabetic mice, and the knockout FoxO1 blocked the formation of diabetic cardiomyopathy induced by high fat diet. The present studies included in vivo and in vitro data shows that adriamycin cardiomyopathy is also associated with, and possibly mediated by, overexpression of FoxO1 in the nuclei of cardiac muscle cells. Interestingly, nuclear localization of GLP-1 in cardiac muscle cells or specific FoxO1 inhibitor (AS1842856) appears to inhibit FoxO1 and restores nearly normal cardiac function and morphology after UTMD GLP-1 gene delivery. Abundant evidence now suggests that 3 members of the FoxO subfamily, FoxO1, FoxO3, and FoxO4, are critical for maintenance of cardiac function and cardiac stress responsiveness (Skurk et al., 2005; Ni et al., 2006; Sengupta et al., 2009; Stahl et al. 2002; Kops et al., 2002; Puigserver et al., 2003; Medema et al., 2000; Schmidt et al., 2002). Taken together, these data indicate that FoxO factors are an important pathway for the development of cardiomyopathy and an important therapeutic target.

As shown herein, nuclear expression of GLP-1 by UTMD promotes adult myocardial regeneration sufficient to reverse adriamycin cardiomyopathy by inhibition of nuclear FoxO1 and by activation of nuclear topoisomerase IIα. This appears to mediate cell cycle re-entry by the activation of cyclin D1 in adult cardiomyocytes. The data indicate that the process of myocardial regeneration is accompanied by dedifferentiation of nuclear FoxO1 positive adult cardiac muscle cells into cardiac progenitor-like cells expressing OCT4, Nanog, SOX2 and c-kit, with subsequent redifferentiation into mature cardiac muscle cells. This phenomenon is not known to occur in adult mammalian cardiac muscle cells under physiological conditions. One can characterize by standard means in the art why nuclear FoxO1 positive adult cardiomyocytes in cardiomyopathy are able to recover the capability of dedifferentiation and proliferation after intranuclear delivery of GLP-1.

Example 3

GLP-1 Plus Thymosin Beta 4 Stimulates Regeneration of Adult Rat Cardiac Muscle and Reversal of Myocardial Ischemic Injury It is estimated that acute myocardial infarction (MI) afflicts 1.3 million Americans every year. Approximately 10% of those patients will die from the MI, typically from ventricular arrhythmias, pump failure, or myocardial rupture. In survivors, infarcted myocardium is replaced by fibrous scar tissue, leading to progressive left ventricular (LV) remodeling and congestive heart failure. Although prompt revascularization of the occluded coronary artery by percutaneous coronary intervention has been shown to reduce mortality, the myocardial microcirculation may not be completely reperfused due to the "no-reflow" phenomenon, and some degree of myocardial necrosis typically remains. Therefore, a major goal of therapy for acute MI has been to develop strategies for regeneration of cardiomyocytes and blood vessels in the damaged area of the heart. Novel strategies for myocardial regeneration include cell therapy with embryonic stem cells, iPS cells and bone marrow stem cells. Recently, resident cardiac progenitor cells were discovered in the adult mammalian heart. Although sparse in number, these cells are self-renewing, clonogenic, and multipotent. In particular embodiments, they can differentiate into all three major cardiac lineages—vascular smooth muscle cells, endothelial cells and cardiac muscle cells. However, it remains controversial whether adult cardiac muscle cells can be formed from these resident progenitor cells in vivo.

As demonstrated herein there is delivery of thymogen beta-4 (TB4)/GLP-1NLS genes directly to the ischemic heart of rats, in order to stimulate resident cardiac progenitor cells.

Objectives:

To determine whether gene therapy with GLP-1NLS/thymosin beta 4 (TB4) stimulates proliferation of resident adult cardiac progenitor or cardiac muscle cells in rat heart with acute ischemic injury.

Background:

It has been proposed that TB4 protein delivery stimulates proliferation and differentiation of resident adult WT1 positive cardiac progenitor cells, but with very low efficiency and GLP-1 has cardioprotective effects.

Methods:

Ultrasound targeted microbubble destruction (UTMD) was used to deliver the GLP-1NLS/TB4 genes under a piggybac transposon plasmid to rat ischemic heart. The rat hearts were assayed by quantitative RT-PCR and immunohistology with a confocal microscope at 2 weeks post UTMD.

Figure 13:
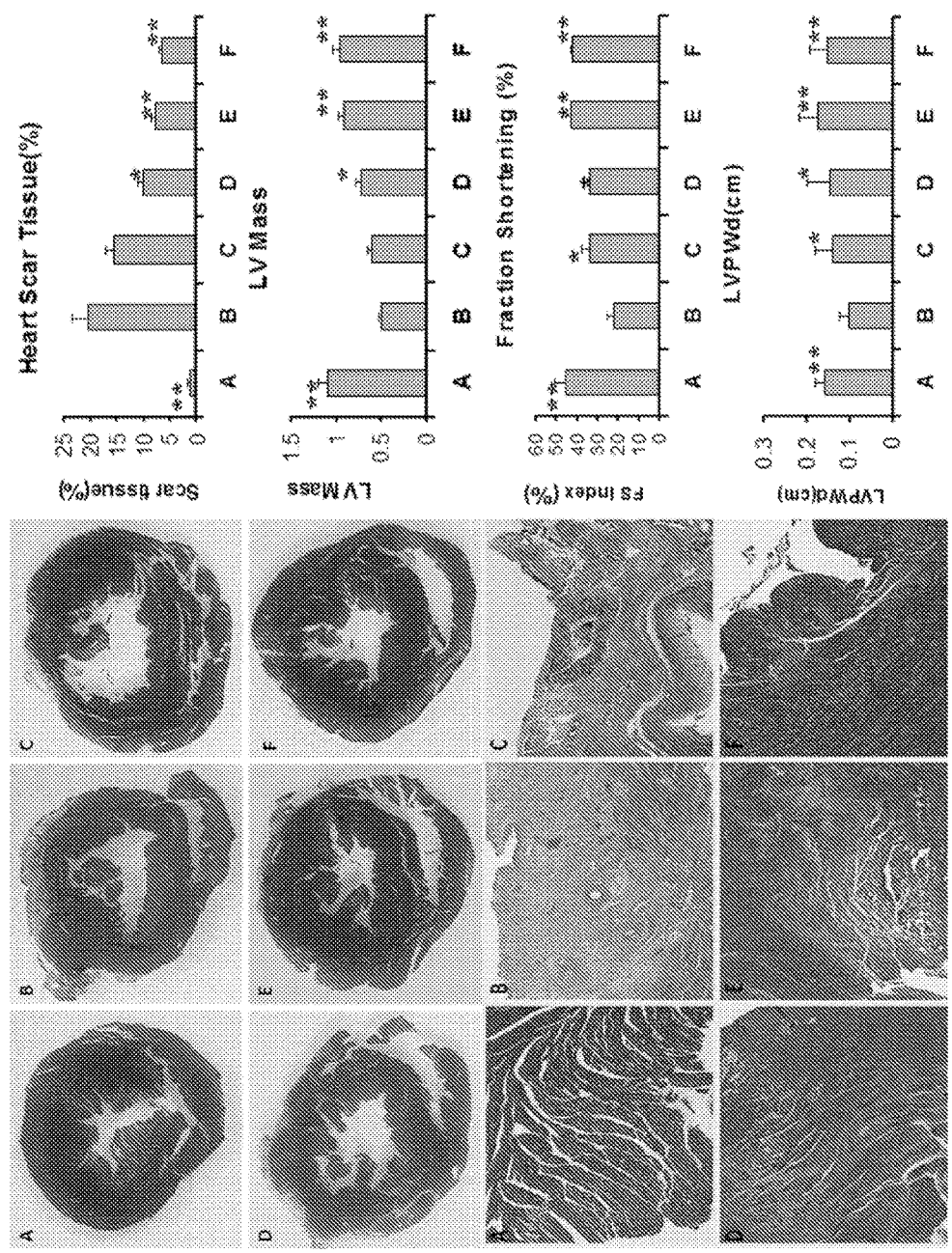
FIG. 13. Masson's trichromone staining images and evaluation of heart function with echocardiography. A: Normal rat heart; B: Ligation of rat coronary artery plus UTMD-DsRed; C: UTMD-GLP-1NLS/TB4 gene therapy one week after ligation of rat coronary artery; D: UTMD-GLP-1NLS/TB4 gene therapy and then quickly ligation of rat coronary artery; E: UTMD-GLP-1NLS/TB4 gene therapy one week and then ligation of rat coronary artery; F: UTMD-GLP-1NLS/TB4 gene therapy two weeks and then ligation of rat coronary artery; The left upper panel is Masson's trichromone staining gross images. The left down panel is Masson's trichromone staining microscope images, Scale bar is 1000 μm. the right panel are graphics of heart scar tissue. LV mass, Fraction shortening and LVPWd. Error bars represent mean±SEM; Number of hearts analyzed for each group: N=6, *P<0.05; **P<0.001 vs control groups.
Figure 14:
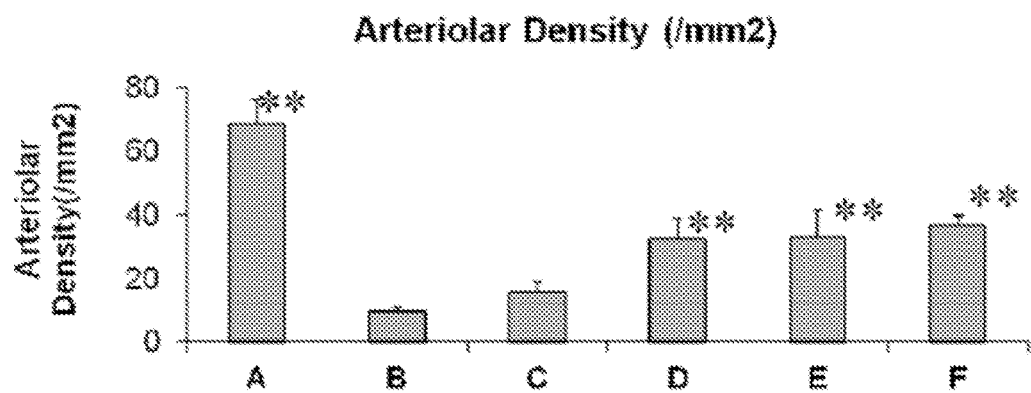
FIG. 14. SMAα staining shows coronary artery distribution in ischemic risk area. Illustrated is the graphic for arteriolar density A: Normal rat heart; B: Ligation of rat coronary artery plus UTMD-DsRed; C: UTMD-GLP-1NLS/TB4 gene therapy one week after ligation of rat coronary artery; D: UTMD-GLP-1NLS/TB4 gene therapy and then quickly ligation of rat coronary artery; E: UTMD-GLP-1NLS/TB4 gene therapy one week and then ligation of rat coronary artery; F: UTMD-GLP-1NLS/TB4 gene therapy two weeks and then ligation of rat coronary artery Error bars represent mean±SEM; Number of hearts analyzed for each group: N=6, *P<0.05; **P<0.001 vs control group (Ligation of rat coronary artery plus UTMD-DsRed).
Figure 15:
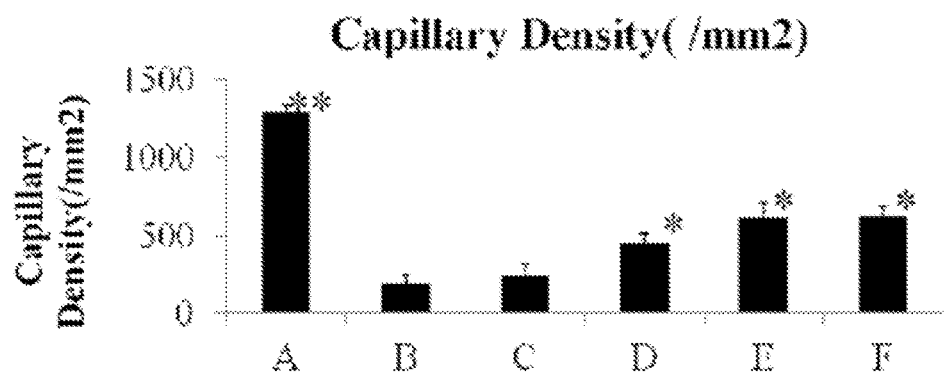
FIG. 15. CD31 staining shows vascular endothelial cells density as shown by the graphic for capillary density. A: Normal rat heart; B: Ligation of rat coronary artery plus UTMD-DsRed; C: UTMD-GLP-1NLS/TB4 gene therapy one week after ligation of rat coronary artery; D: UTMD-GLP-1NLS/TB4 gene therapy and then quickly ligation of rat coronary artery; E: UTMD-GLP-1NLS/TB4 gene therapy one week and then ligation of rat coronary artery; F: UTMD-GLP-1NLS/TB4 gene therapy two weeks and then ligation of rat coronary artery. Error bars represent mean±SEM; Number of hearts analyzed for each group: N=6, *P<0.05; **P<0.001 vs control group (Ligation of rat coronary artery plus UTMD-DsRed).
Figure 16:
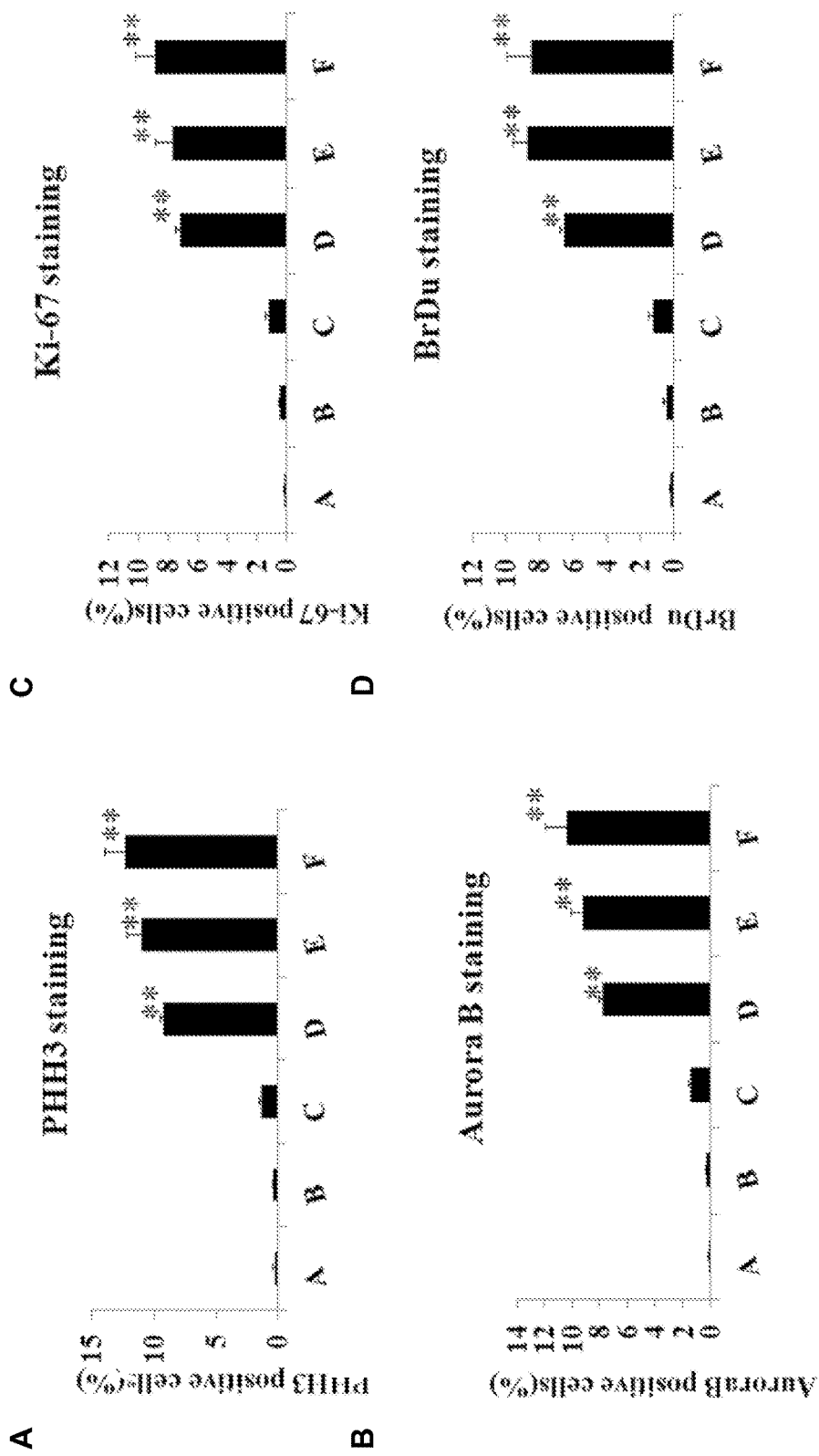
FIG. 16. Proliferation markers staining shown cardiac muscle cells are in proliferation after UTMD-GLP-1NLS/TB4 gene therapy. The graphics are for the percentage of PHH3(A), Aurora B(B), Ki-67(C), BrDu(D) positive cardiac muscle cells. Values are presented as mean±SEM; n=6 per group; **P<0.001 vs control groups. In the graphics, A: Normal rat heart; B: Ligation of rat coronary artery plus UTMD-DsRed; C: UTMD-GLP-1NLS/TB4 gene therapy one week after ligation of rat coronary artery; D: UTMD-GLP-1NLS/TB4 gene therapy and then quickly ligation of rat coronary artery; E: UTMD-GLP-1NLS/TB4 gene therapy one week and then ligation of rat coronary artery; F: UTMD-GLP-1NLS/TB4 gene therapy two weeks and then ligation of rat coronary artery.

Results:

FIG. 13 demonstrates Masson's trichromone staining images and evaluation of heart function with echocardiography. FIG. 14 demonstrates that SMAα staining shows coronary artery distribution in ischemic risk area. FIG. 15 provides CD31 staining that shows vascular endothelial cells density. FIG. 16 demonstrates proliferation marker staining showing that cardiac muscle cells are in proliferation after UTMD-GLP-1NLS/TB4 gene therapy.

Thus, GLP-1NLS/TB4 genes stimulation resulted in the ischemic area reduction in ischemic myocardium. GLP-1NLS/TB4 stimulated angiogenesis and arteriogenesis. One month after GLP-1/TB4 gene therapy by UTMD, the percentage of NKX2.5 positive cardiomyocytes was 5.5±1.0%, and NKX2.5 mRNA was 24-fold higher than in the control groups (p<0.001). Similar results were found for ISL-1, BrDu, Ki-67, PHH3 and aurora B (p<0.001).

Conclusions:

GLP-1NLS/TB4 genes efficiently stimulates proliferation and differentiation of adult cardiac muscle cells into three intact cardiac cell lineages-vascular endothelial cells, coronary artery smooth muscle cells and cardiac muscle cells in rat ischemic heart.

REFERENCES

All patents and publications mentioned in this specification are indicative of the level of those skilled in the art to which the disclosure pertains. All patents and publications herein are incorporated by reference to the same extent as if each individual publication was specifically and individually indicated to be incorporated by reference in their entirety.

Battiprolu, et al., J Clin Invest. 2012; 122:1109-1118.
Bekeredjian, et al., Circulation. 2003; 108(8): 1022-26
Beltrami, et al., Cell. 2003; 114:763-776.
Bersell, et al., Cell. 2009; 138:257-270.
Bolli, et al., Lancet. 2011; 378: 1847-1857.
Boni, et al., Proc Natl Acad Sci USA. 2008; 105:15529-15534.
Cadifianos, et al., Nucleic Acids Res. 2007; 35:e87.
Cary, et al., Virology 1989; 172:156-69.
Chatterjee, et al., Cardiology. 2010; 115:155-162.
Chen, et al., Gene Ther. 2013; 20:225-33.
Chen, et al., Cell Cycle. 2012; 11:695-705.
Chen, et al., J Am Coll Cardiol. 2003; 42: 301-8.
Claycomb, et al., Proc Natl Acad Sci USA. 1998; 95:2979-2984.
Drucker, et al., Gastroenterology. 2002; 122:531-44.
Drucker, et al., Endocrinology. 2001; 142:521-7
Eulalio, et al., Nature. 2012; 492:376-81.
Fraser, et al., Virology 1995; 211: 397-407.
Halbirk, et al., Am J Physiol Heart Circ Physiol. 2010; 298:H1096-102.
Iliskovic, et al., American Journal of Pathology. 1997; 150:727-734.
Jopling, et al., Nature. 2010; 464: 606-609.
Kim, et al., Nat Med. 2013; 19:567-575.
Kops, et al., Nature. 2002; 419:316-321.
Korpanty, et al., Gene Therapy. 2005; 12: 1305-12
Medema, et al., Nature. 2000; 404:782-787.
Ni, et al., Circulation. 2006; 114:1159-1168.
Nowbar, et al., BMJ. 2014; 348:g2688.
Porrello, et al., Science. 2011; 331:1078-1080.
Puigserver, et al., Nature. 2003; 423:550-555.
Qian, et al., Nature. 2012; 485:593-598.
Roger, et al., Circulation. 2012; 125:e2-e220.
Saridey, et al., Mol Ther. 2009; 17: 2115-20.
Schmidt, et al., Mol Cell Biol. 2002; 22:7842-7852.
Sengupta, et al., J Biol Chem. 2009; 284:28319-28331.
Senyo, et al., *Nature* 2012; 493, 433-436.
Sinkula, et al., J Pharm Sci. 64:181-210, 1975.
Skurk, et al., J Biol Chem. 2005; 280:20814-20823.
Smart, et al., Nature. 2011; 474: 640-644.
Song, et al., Nature 2012; 485:599-604.
Stahl, et al., J Immunol. 2002; 168:5024-5031.
Talchai, et al., Cell. 2012; 150:1223-1234.
Timmers, et al., J Am Coll Cardiol. 2009; 53:501-10.
Ussher, et al., Endocr Rev. 2012; 33:187-215.
Yusa, et al., Proc Natl Acad Sci USA. 2011; 108:1531-1536.
Zhang, et al., Nat Med. 2012; 18:1639-1642.

Although the present disclosure and its advantages have been described in detail, it should be understood that various changes, substitutions and alterations can be made herein without departing from the spirit and scope of the disclosure as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

What is claimed is:

1. A method of localizing glucagon-like peptide (GLP)-1 to the nucleus of cells that are cardiomyocytes, skeletal myocytes, or smooth muscle myocytes, comprising the steps of:
providing to the cells an effective amount of lipid-stabilized microbubbles having liposomes attached to the outer surface of a shell of the microbubbles, incorporated within the shell of the microbubbles, and/or encapsulated within the shell of the microbubbles, wherein the liposomes comprise GLP-1 or a nucleic acid that encodes GLP-1 encapsulated within or attached to the liposome; and
exposing the microbubbles to ultrasound conditions sufficient to deliver GLP-1 or the nucleic acid that encodes GLP-1 into the nuclei of the cells, wherein the microbubbles further comprise thymosin beta 4 (TB4).

2. The method of claim 1, wherein the cell membrane of the cells lacks GLP-1 receptors.

3. The method of claim 1, wherein the cell membrane of the cells has GLP-1 receptors.

4. The method of claim 1, wherein the cells are located in vitro.

5. The method of claim 1, wherein the cells are located in vivo.

6. The method of claim 1, wherein the nucleic acid that encodes GLP-1 is delivered into the nuclei of the cells.

7. The method of claim 1, wherein GLP-1 is delivered into the nuclei of the cells.

8. The method of claim 6, wherein the nucleic acid is comprised in a vector.

9. The method of claim 6, wherein the nucleic acid further comprises sequence that encodes a nuclear localization signal.

10. The method of claim 1, wherein the microbubbles further comprise albumin, polymer shell, or a graphite shell.

11. The method of claim 1, wherein the microbubbles further comprise a gas.

12. The method of claim 5, wherein the cells are in an individual that has a cardiac-related medical condition.

13. The method of claim 12, wherein the cardiac-related medical condition is a cardiomyopathy that is induced by a drug.

14. The method of claim 13, wherein the drug is a chemotherapy drug.

15. The method of claim 13, wherein the drug is Adriamycin.

16. A method of localizing glucagon-like peptide (GLP)-1 to the nucleus of cells that are cardiomyocytes, skeletal myocytes, or smooth muscle myocytes, comprising the steps of:
providing to the cells an effective amount of lipid-stabilized microbubbles having liposomes attached to the outer surface of a shell of the microbubbles, incorporated within the shell of the microbubbles, and/or encapsulated within the shell of the microbubbles, wherein the liposomes comprise GLP-1 or a nucleic acid that encodes GLP-1 encapsulated within or attached to the liposome; and
exposing the microbubbles to ultrasound conditions sufficient to deliver GLP-1 or the nucleic acid that encodes GLP-1 into the nuclei of the cells, wherein the cells are in an individual that has a cardiomyopathy that is induced by a drug.

17. The method of claim 16, wherein the drug is Adriamycin.

18. The method of claim 16, wherein the cell membrane of the cells lacks GLP-1 receptors.

19. The method of claim 16, wherein the cell membrane of the cells has GLP-1 receptors.

20. The method of claim 16, wherein the cells are located in vitro.

21. The method of claim 16, wherein the cells are located in vivo.

22. The method of claim 16, wherein nucleic acid that encodes GLP-1 is delivered into the nuclei of the cells.

23. The method of claim 16, wherein GLP-1 is delivered into the nuclei of the cells.

24. The method of claim 22, wherein the nucleic acid is comprised in a vector.

25. The method of claim 22, wherein the GLP-1 nucleic acid further comprises sequence that encodes a nuclear localization signal.

26. The method of claim 16, wherein the microbubbles further comprise albumin, polymer shell, or a graphite shell.

27. The method of claim 16, wherein the microbubbles further comprise a gas.

* * * * *

SEQUENCE LISTING

```
<160> NUMBER OF SEQ ID NOS: 10

<210> SEQ ID NO 1
<211> LENGTH: 111
<212> TYPE: DNA
<213> ORGANISM: Homo sapiens

<400> SEQUENCE: 1
cacgatgaat tgagagaca tgctgaaggg acctttacca gtgatgtaag ttcttatttg    60
gaaggccaag ctgccaagga attcattgct tggctggtga aaggccgagg a           111

<210> SEQ ID NO 2
<211> LENGTH: 28
<212> TYPE: PRT
<213> ORGANISM: Homo sapiens

<400> SEQUENCE: 2
```

```
His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys
            20                  25

<210> SEQ ID NO 3
<211> LENGTH: 21
<212> TYPE: DNA
<213> ORGANISM: Artificial Sequence
<220> FEATURE:
<223> OTHER INFORMATION: Synthetic Primer

<400> SEQUENCE: 3
cctaaaaaaa agcggaaggt c                                              21

<210> SEQ ID NO 4
<211> LENGTH: 153
<212> TYPE: DNA
<213> ORGANISM: Artificial Sequence
<220> FEATURE:
<223> OTHER INFORMATION: Synthetic Primer

<400> SEQUENCE: 4
aaactcgaga tgcgtcaacg tcgtcatgct gaagggacct ttaccagtga tgtgagttct     60
tacttggagg gccaggcagc aaaggaattc attgcttggc tggtgaaagg ccgaggacct    120
aaaaaaaagc ggaaggtcta ggcggccgca aaa                                 153

<210> SEQ ID NO 5
<211> LENGTH: 1062
<212> TYPE: DNA
<213> ORGANISM: Homo sapiens

<400> SEQUENCE: 5
gctctgttct acagcacact accagaagac agcagaaatg aaaagcattt actttgtggc     60
tgggttattt gtaatgctgg tacaaggcag ctggcaacgt tcccttcaag acacagagga    120
gaaatccaga tcattctcag cttcccaggc agacccactc agtgatcctg atcagatgaa    180
cgaggacaag cgccattcac agggcacatt caccagtgac tacagcaagt atctggactc    240
caggcgtgcc caagattttg tgcagtggtt gatgaatacc aagaggaaca ggaataacat    300
tgccaaacgt cacgatgaat tgagagaca tgctgaaggg accttaccca gtgatgtaag    360
ttcttatttg gaaggccaag ctgccaagga attcattgct tggctggtga aggccgagg    420 aaggcgagat ttcccagaag aggtcgccat tgttgaagaa cttggccgca gacatgctga    480
tggttctttc tctgatgaga tgaacaccat tcttgataat cttgccgcca gggactttat    540
aaactggttg attcagacca aaatcactga caggaaataa ctatatcact attcaagatc    600
atcttcacaa catcacctgc tagccacgtg ggatgtttga atgttaagt cctgtaaatt    660 taagaggtgt attctgaggc acattgctt tgcatgccaa taataaatt ttctttagt     720 gttgtgtagc caaaaattac aaatggaata agtttatc aaaatattgc taaaatatca      780
gctttaaaat atgaaagtgc tagattctgt tattttcttc ttattttgga tgaagtaccc    840
caacctgttt acatttagcg ataaaattat ttttctatga tataatttgt aaatgtaaat    900
tattccgatc tgacatatct gcattataat aataggagaa tagaagaact ggtagccaca    960
gtggtgaaat tggaaagaga actttcttcc tgaaaccttt gtcttaaaaa tactcagctt   1020
tcaatgtatc aaagatacaa ttaaataaaa ttttcaagct tc                     1062
```

<210> SEQ ID NO 6
<211> LENGTH: 180
<212> TYPE: PRT
<213> ORGANISM: Homo sapiens

<400> SEQUENCE: 6

Met Lys Ser Ile Tyr Phe Val Ala Gly Leu Phe Val Met Leu Val Gln
1               5                   10                  15

Gly Ser Trp Gln Arg Ser Leu Gln Asp Thr Glu Glu Lys Ser Arg Ser
            20                  25                  30

Phe Ser Ala Ser Gln Ala Asp Pro Leu Ser Asp Pro Asp Gln Met Asn
        35                  40                  45

Glu Asp Lys Arg His Ser Gln Gly Thr Phe Thr Ser Asp Tyr Ser Lys
    50                  55                  60

Tyr Leu Asp Ser Arg Arg Ala Gln Asp Phe Val Gln Trp Leu Met Asn
65                  70                  75                  80

Thr Lys Arg Asn Arg Asn Asn Ile Ala Lys Arg His Asp Glu Phe Glu
                85                  90                  95

Arg His Ala Glu Gly Thr Phe Thr Ser Asp Val Ser Ser Tyr Leu Glu
            100                 105                 110

Gly Gln Ala Ala Lys Glu Phe Ile Ala Trp Leu Val Lys Gly Arg Gly
        115                 120                 125

Arg Arg Asp Phe Pro Glu Glu Val Ala Ile Val Glu Glu Leu Gly Arg
    130                 135                 140

Arg His Ala Asp Gly Ser Phe Ser Asp Glu Met Asn Thr Ile Leu Asp
145                 150                 155                 160

Asn Leu Ala Ala Arg Asp Phe Ile Asn Trp Leu Ile Gln Thr Lys Ile
                165                 170                 175

Thr Asp Arg Lys
            180

<210> SEQ ID NO 7
<211> LENGTH: 43
<212> TYPE: DNA
<213> ORGANISM: Artificial Sequence
<220> FEATURE:
<223> OTHER INFORMATION: Synthetic Primer

<400> SEQUENCE: 7
aaactcgaga tgcgtcaacg tcgtcatgct gaagggacct tta                43

<210> SEQ ID NO 8
<211> LENGTH: 54
<212> TYPE: DNA
<213> ORGANISM: Artificial Sequence
<220> FEATURE:
<223> OTHER INFORMATION: Synthetic Primer

<400> SEQUENCE: 8
aaaagccgct cagaccttcc gcttttttt aggtcctcgg cctttcacca gcca       54

<210> SEQ ID NO 9
<211> LENGTH: 637
<212> TYPE: DNA
<213> ORGANISM: Homo sapiens

<400> SEQUENCE: 9
ggccactgcg cagaccagac ttcgctcgta ctcgtgcgcc tcgcttcgct tttcctccgc    60
aaccatgtct gacaaacccg atatggctga gatcgagaaa ttcgataagt cgaaactgaa   120

-continued

```
gaagacagag acgcaagaga aaaatccact gccttccaaa gaaacgattg aacaggagaa      180
gcaagcaggc gaatcgtaat gaggcgtgcg ccgccaatat gcactgtaca ttccacaagc      240
attgccttct tattttactt cttttagctg tttaactttg taagatgcaa agaggttgga      300
tcaagtttaa atgactgtgc tgccccttc acatcaaaga actactgaca acgaaggccg       360
cgcctgcctt tcccatctgt ctatctatct ggctggcagg gaaggaaaga acttgcatgt      420
tggtgaagga agaagtgggg tggaagaagt ggggtgggac gacagtgaaa tctagagtaa      480
aaccaagctg gcccaaggtg tcctgcaggc tgtaatgcag tttaatcaga gtgccatttt      540 ttttttgtt caaatgattt taattattgg aatgcacaat tttttttaata tgcaaataaa     600 aagtttaaaa acttaaaaaa aaaaaaaaaa aaaaaaa                               637
```

<210> SEQ ID NO 10
<211> LENGTH: 44
<212> TYPE: PRT
<213> ORGANISM: Homo sapiens

<400> SEQUENCE: 10

```
Met Ser Asp Lys Pro Asp Met Ala Glu Ile Glu Lys Phe Asp Lys Ser
1               5                   10                  15

Lys Leu Lys Lys Thr Glu Thr Gln Glu Lys Asn Pro Leu Pro Ser Lys
            20                  25                  30

Glu Thr Ile Glu Gln Glu Lys Gln Ala Gly Glu Ser
        35                  40
```